Figure 1A:
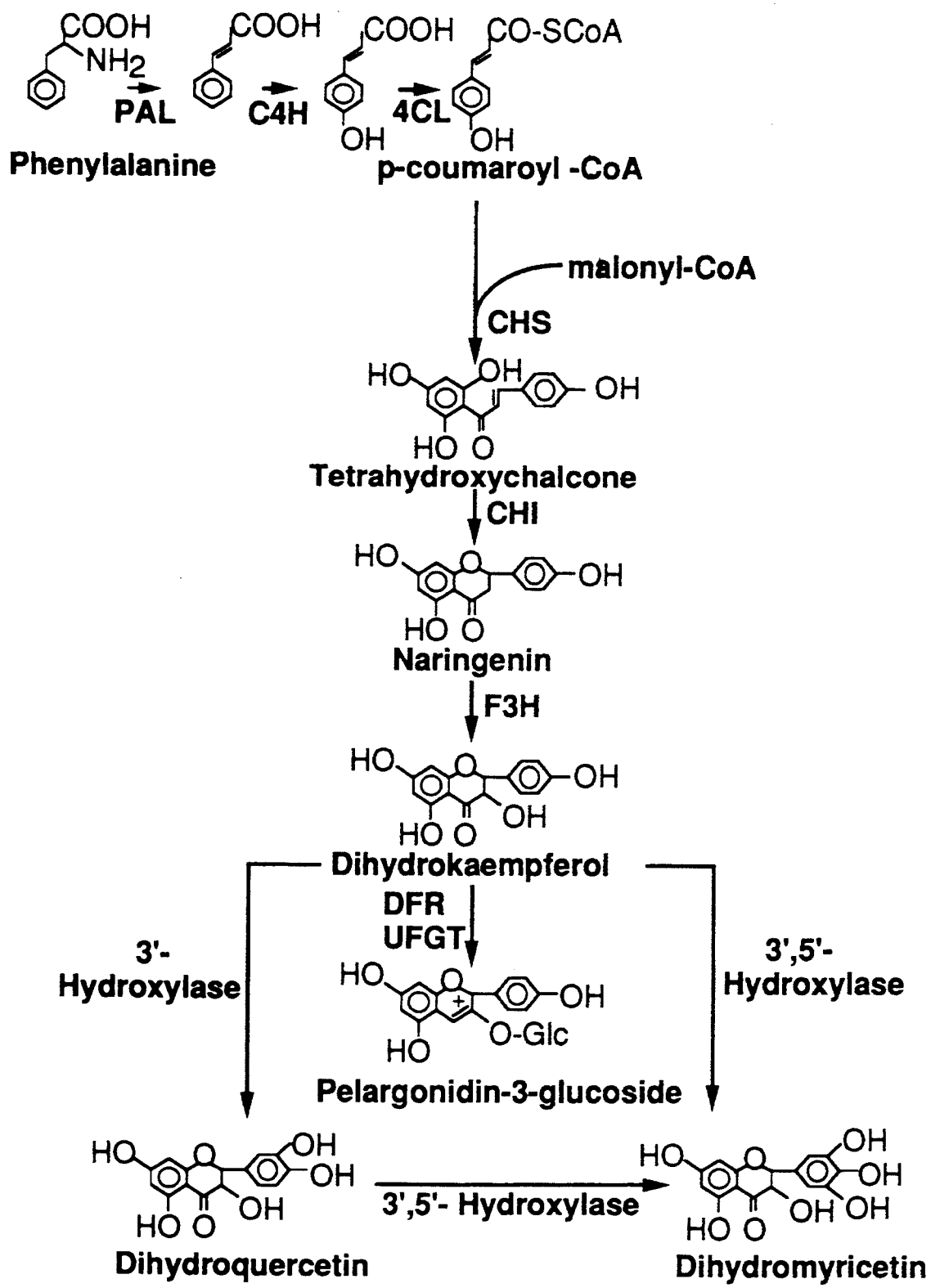

United States Patent [19]
Holton et al.

[11] Patent Number: 5,349,125
[45] Date of Patent: Sep. 20, 1994

[54] GENETIC SEQUENCES ENCODING A 3',5'-HYDROXYLASE AND USES THEREFOR

[75] Inventors: Timothy A. Holton, Northcote; Edwina C. Cornish, Upper Beaconsfield; Filippa Kovacic, Preston; Yoshikazu Tanaka, Rosanna; Diane R. Lester, Triabunna, all of Australia

[73] Assignee: International Flower Developments Pty. Ltd., Australia

[21] Appl. No.: 912,900

[22] Filed: Jul. 13, 1992

[30] Foreign Application Priority Data

Jul. 11, 1991 [AU] Australia .................. PK7173/91
Feb. 17, 1992 [AU] Australia .................. PL0923/92

[51] Int. Cl.⁵ ............... A01H 4/00; C12N 15/29; C12N 15/82
[52] U.S. Cl. ............... 800/205; 800/DIG. 43; 800/DIG. 67; 435/320.1; 435/172.3; 536/23.6
[58] Field of Search ............... 536/23.6; 435/320.1, 435/172.3; 800/205, DIG. 67, 68, DIG. 43; 935/67

[56] References Cited

U.S. PATENT DOCUMENTS

5,034,323  7/1991  Jorgensen et al. ............... 435/172.3

OTHER PUBLICATIONS

Fuqua, et al. (1990) Biotechniques 9(2):206–210.
Boswell, et al. in Computational Molecular Biology. Sources and Methods for sequence analysis (Lesk, ed.) Oxford University Press, Oxford, 1988 pp. 170–171.
van der Krol, et al. (1990) Plant Molecular Biology 14:457, Abstract.
Bozak, et al. (May 1990) Proc. Natl. Acad. Sci, USA 87:3904–3908.

*Primary Examiner*—Che S. Chereskin
*Attorney, Agent, or Firm*—Scully, Scott, Murphy & Presser

[57] ABSTRACT

The present invention relates to a nucleic acid isolate comprising a sequence of nucleotides encoding, or complementary to a sequence encoding, a dihydrokaempferol (DHK) hydroxylating enzyme or derivative or part thereof. The present invention also relates to transgenie plants carrying and expressing the above mentioned nucleic acid material.

16 Claims, 35 Drawing Sheets

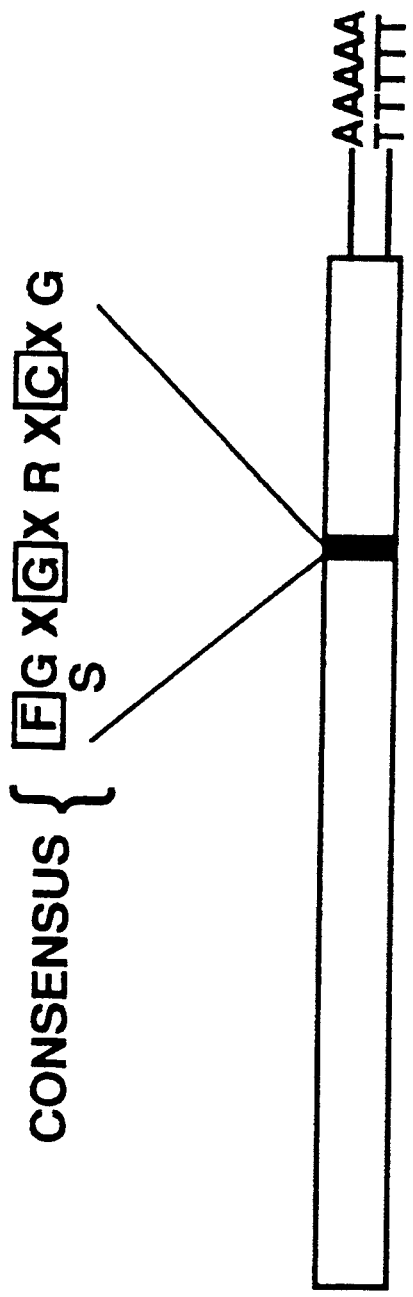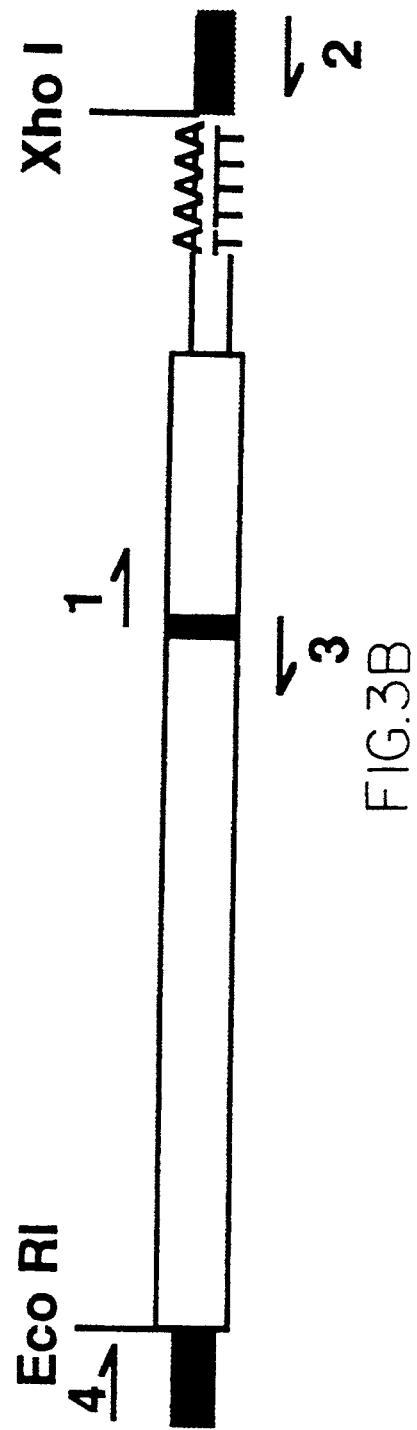
FIG.3A
FIG.3B pCGP 142

```
  F   S   S   I   R   N   D   E   I   S   S   L
TTT AGT TCA ATT CGG AAT GAT GAG ATT TCG AGT CTC
            ───────►
  I   S   S   I   H   S   M   N   G   S   V   V
ATT TCA TCA ATT CAT TCC ATG AAC GGT TCT GTT GTC

N   M   T   Q   K   I   L   C   F   T   N   S
AAC ATG ACA CAA AAG ATT CTT TGT TTT ACA AAC TCT

V   T   C   R   T   A   F   G   K   V   Y   K
GTG ACT TGT AGA ACA GCT TTC GGG AAA GTA TAC AAA

N   Q   N   E   L   I   N   L   M   R   E   V
AAT CAA AAT GAA TTG ATA AAC TTG ATG AGG GAA GTA

L   E   L   V   G   G   F   D   ────────────────
CTG GAA TTA GTA GGA GGA TTT GAT ────────────────

F   E   N   S   P   V   E   F   I   G   N   H
TTT GAA AAT TCT CCG GTT GAG TTT ATT GGA AAT CAC

F   E   L   V   P   F   G   A   G   K   R   I
TTT GAG CTT GTT CCG TTT GGT GCA GGA AAA AGG ATT

C   P   G   M   Q   F   G   L   A   N   I   R
TGT CCA GGA ATG CAA TTT GGT TTA GCT AAT ATT AGA

H   P   L   A   R   F   L   Y   H   F   N   W
CAT CCT TTG GCT CGA TTC CTC TAC CAT TTT AAC TGG

A   L   P   Y   E   T   N   P   E   D   L   D
GCG CTT CCA TAT GAA ACT AAT CCT GAA GAT TTA GAT

S   L   K   N   M   D
AGT CTG AAA AAT ATG GAT TAA GTGCAGCAAAAGAGAAAGA
                                ◄──────
TCTATACTTAATTGCCGTAGATCACAAGAAGGTGATATATAAATTC
TGATGTTCTGCTTTAAATGGTGAAAGTCATACTCTACACAATGCTTC
ATCTCCTTAATTTGAGTTTGGTGTACATTTGTGTCTCCCTTTTAGCT
TTGAATTTCACCTTGAAAAATGATCACATTTTCTTTTTCTGTTACTC
CAATTAAGATATATGTTGTGGTTGGTCAATTATGCCATATTTATCAA
AAGATCAAATCAATTCCCTCGTTGATAAGTATAGATTATAAAACTGA
TTAATGAATCAAAAAAAAAAAAAAAAA
```

FIGURE 4B pCGP147

```
  F   T   S   S   M   I   C   R   S   V   F   G   K   R   I   K
TTCACAAGCTCTATGATTTGTAGATCAGTATTTGGGAAAAGAATAAAG
     538        548        558        568

E   K   D   E   C   I   R   H   V   K   K   M   T   G   L   I
GAGAAAGACGAATGTATACGACATGTGAAAAAAATGACAGGCTTAATA
     586        596        606        616

D   G   F   D   V   A   D   I   F   P   S   L   R   F   L   H
GATGGGTTCGATGTGGCTGACATATTCCCTTCGTTGAGGTTTCTTCAT
     634        644        654        664

V   L   I   G   M   K   G   K   I   M   D   V   H   R   K   V
GTACTAATCGGTATGAAGGGTAAAATTATGGATGTTCATCGTAAGGTA
     682        692        702        712

D   A   I   V   E   E   V   M   N   E   H   K   E   T   L   R
GATGCTATTGTTGAGGAAGTCATGAATGAGCACAAAGAAACTCTTCGA
     730        740        750        760

T   G   K   T   N   G   E   V   G   G   E   D   L   I   D   V
ACTGGCAAGACCAATGGTGAAGTGGGAGGAGAAGATTTAATTGATGTA
     778        788        798        808

L   L   R   L   K   E   E   G   D   L   Q   L   P   I   T   N
TTGCTAAGACTTAAGGAAGAGGGAGACCTTCAACTTCCAATCACAAAT
     826        836        846        856

D   N   I   K   A   I   F   N   D   M   F   A   A   G   T   E
GACAACATCAAAGCCATTTTTAATGACATGTTTGCTGCGGGAACAGAA
     874        884        894        904

T   S   S   T   T   I   N   W   A   M   V   E   L   M   K   N
ACTTCATCAACAACAATTAACTGGGCCATGGTAGAACTGATGAAAAAT
     922        932        942        952

P   S   V   F   A   K   A   Q   A   E   V   R   E   V   F   K
CCAAGTGTATTCGCGAAAGCTCAAGCAGAGGTAAGAGAAGTCTTCAAA
     970        980        990        1000

G   K   E   T   F   D   E   D   D   I   E   E   L   N   Y   L
GGGAAAGAAACTTTCGATGAAGATGATATCGAGGAGCTGAATTACCTT
     1018       1028       1038       1048

K   L   V   I   R   E   T   L   R   L   H   P   P   L   P   L
AAGTTAGTCATTAGAGAAACTTTAAGACTCCACCCTCCACTTCCACTT
     1066       1076       1086       1096
```

FIGURE 4D

```
      L   L   P   R   E   C   R   R   E   T   E   I   N   G   Y   T
    TTGCTTCCAAGAGAATGTCGGAGAGAAACAGAAATAAATGGCTACACT
         1114        1124        1134        1144

I   P   L   N   T   K   V   I   V   N   V   W   A   I   G   R
    ATTCCTTTAAATACCAAAGTCATAGTTAATGTTTGGGCTATTGGAAGA
         1162        1172        1182        1192

D   P   K   Y   W   D   D   A   E   S   F   K   P   E   R   F
    GATCCAAAATATTGGGATGATGCAGAAAGCTTTAAGCCTGAGAGATTT
         1210        1220        1230        1240

E   H   N   S   L   N   F   A   G   N   N   F   E   Y   L   P
    GAACATAACTCTTTGAATTTTGCTGGCAATAATTTTGAATATCTTCCT
         1258        1268        1278        1288

F   G   S   G   R   R   I   C   P   G   I   S   F   G   L   A
    TTTGGTAGTGGAAGGAGGATTTGCCCCGGAATATCATTTGGTTTAGCT
         1306        1316        1326        1336

N   V   Y   H   P   L   A   Q   L   L   Y   H   F   D   W   R
    AATGTTTATCATCCATTGGCTCAATTGTTGTATCATTTCGATTGGAGA
         1354        1364        1374        1384

L   P   T   G   V   D   P   N   D   F   E   L   T   S   *
    CTTCCTACTGGGGTCGACCCAAATGACTTTGAATTGACTAGTTAGCTG
         1402        1412        1422        1432
    ←

GAGTAACTACTGGTAGGAAAAGAGACCTTTACTTGATTTTCACTCCTT
         1450        1460        1470        1480

ATTCACCTTCTCTAAAGTGATTAAATGG-GCAAATTTTAATTTGAAAT
         1498        1508        1518        1528

AATACTTTTTCTTGTTTACATTTCTCTCCCATTGTTGTATTTCATTTA
         1546        1556        1566        1576

CCTATTGTTGTACTTCTTTCTTTTGTTGATGTCTTAGGTTTTACCTAT
         1594        1604        1614        1624

TTCTATGCATTTGTATTTAAAAAAAAAAAAAAAAA
         1642        1652        1662
```

FIGURE 4E pCGP158

```
Gly Met Met Lys Gln Gly Asp Phe Leu Asp Val Leu
GGG ATG ATG AAG CAA GGA GAT TTC TTG GAT GTA CTT
───────────────────►

Leu Asp Gln Cys Asp Glu Glu Gly Ser Gly Phe Asp
CTT GAT CAA TGT GAT GAA GAA GGG TCT GGA TTT GAT

Arg Gln Thr Ile Lys Pro Leu Ile Leu Asp Leu Phe
CGC CAA ACT ATC AAG CCT CTC ATC CTG GAT TTA TTC

Ile Ala Gly Ser Asp Thr Ser Ala Ile Thr Thr Glu
ATT GCT GGA AGT GAT ACA TCT GCC ATA ACA ACA GAA

Trp Ala Met Ala Glu Leu Leu Arg Lys Pro Gln Glu
TGG GCA ATG GCA GAA CTA CTT CGA AAA CCT CAA GAA

----------------------------------------------------
----------------------------------------------------

Phe Val Asn Ala Trp Ala Ile Gly Arg Asp Pro Lys
TTT GTG AAT GCA TGG GCA ATT GGA AGA GAT CCA AAA

Tyr Trp Glu Lys Pro Leu Glu Phe Met Pro Glu Arg
TAC TGG GAA AAA CCA CTG GAG TTT ATG CCT GAA AGA

Phe Leu Lys Cys Ser Leu Asp Tyr Lys Gly Arg ---
TTC TTG AAG TGT AGT TTG GAT TAC AAA GGT AGG G--

Phe Glu Tyr Ile Pro Phe Gly Ala Gly Arg Arg Ile
TTT GAG TAT ATA CCA TTT GGC GCA GGT CGA AGA ATT

Cys Pro Gly Met Pro His Cys Asn Lys Asp Gly Glu
TGT CCT GGA ATG CCA CAT TGC AAT AAG GAT GGT GAA

Phe Asp Ala Gly Phe Asp Tyr Ser Pro Phe Ser Trp
TTT GAT GCT GGC TTC GAT TAT TCA CCA TTT AGT TGG

Glu Leu Pro --- Gly Met Ala Pro Lys --- Leu Asn
GAA TTA CCT -AA GGA ATG GCA CCA AAG -AT TTG AAC

Met Glu Glu Gln Phe Gly Val Thr Leu Arg Lys Ala
ATG GAG GAA CAG TTT GGA GTT ACC TTG AGG AAG GCT

Ile Pro Leu Ile Ala Ile Pro Ser Met Glu Glu Lys
ATT CCC CTT ATT GCC ATT CCC AGT ATG GAA GAA AAG

Val Ile Phe
GTC ATA TTT TAG CCCAAAAGCTATGCATTTTGTGTGTATGTTT
                ◄───────────
```

FIGURE 4F pCGP 160

```
  K   Q   I   N   A   L   L   V   E   I   F   G
 AAA CAG ATC AAT GCA TTG CTT GTG GAA ATA TTT GGA
 ━━━━━━━━━━━━━━━━━━━━━━━━━━▶
  A   G   T   E   S   T   T   A   T   S   Q   W
 GCT GGT ACA GAA TCT ACA ACT GCT ACA AGC CAA TGG

M   L   V   E   L   L   R   N   R   Q   A   L
 ATG CTT GTA GAA CTC CTT AGA AAT CGA CAA GCC TTG

------------- P   K   D   T   Q   V   M   V   N
 -------------CCC AAA GAC ACT CAA GTT ATG GTA AAC

E   W   A   I   A   Y   D   P   K   I   W   G
 GAG TGG GCG ATT GCG TAT GAT CCT AAG ATT TGG GGC

S   F   K   P   Q   R   F   I   D   S   K   I
 AGC TTC AAA CCC GAA AGG TTT ATC GAT TCA AAA ATA

D   P   L   D   H   K   G   Q   N   F   E   Y
 GAT CCT TTG GAC CAC AAA GGG CAA AAT TTT GAA TAT

F   P   F   G   S   G   R   R   I   C   A   G
 TTT CCT TTT GGT TCT GGA AGG AGA ATT TGT GCT GGA

E   P   L   A   S   R   V   I   P   L   A   V
 GAA CCT TTG GCT TCT AGG GTT ATT CCC TTA GCT GTT

A   S   M   I   H   K   F   ---------
 GCT TCT ATG ATC CAT AAG TTT ---------GATATCACTAT
                                    ◀━━━━━━━━━━━
 GTTAGAAGATCCACTCTCATCATTCCTAAGTTGAGAAGAGTGAGGAA

ATTAAAAGAAGCAGAAGATATGTTACTATAAAAACTCGTTATATATA

TATATATTGCTGTATCTATATATGTGTGAATGATCTGCTGCTCATGT

TGTGTTTTGTTGTTTGTGTACTATAGGTCATACCTAAGTTGATGAAA

TGTCTCTGAGAATATATACTCCTTATATAATAGGAGTAATTTACCGA

TAATTAATATTCCTGCGACAAAAAAAAAAAAAAAAA
```

FIGURE 4G pCGP454

```
    -   R   E   S   M   E   D   V   R   L   L   G
    CT CGA GAA TCA ATG GAA GAT GTA AGA TTA CTA GGC
    ────────────────►
    Y   H   I   P   A   K   T   R   L   F   I   N
    TAT CAC ATA CCT GCT AAA ACG AGA CTC TTT ATC AAT

A   W   T   M   G   R   D   P   L   T   W   E
    GCT TGG ACA ATG GGG AGA GAC CCA CTA ACA TGG GAA

N   P   E   E   Y   Q   P   E   R   F   L   N
    AAT CCA GAA GAG TAT CAG CCA GAG AGA TTC TTG AAT

R   D   T   D   V   K   G   V   N   F   E   F
    AGA GAT ACT GAT GTC AAA GGA GTA AAC TTT GAG TTC

I   P   F   G   A   G   R   S
    ATT CCC TTT GGC GCC GGC AGA AGC
                      ◄────────────
```

FIGURE 4H pCGP 602

```
CTTTCTACTAGCTACTTCGTTATATATGTAAAATTGTGACTTT
      10        20        30        40

GAAAATCATTTAAATTATCATAAGGTTCATTTTATCTTGATCAAA
      55        65        75        85

M   M   L
ATATTTACTTCGGCCATATACGTTTTCCTTTAGTCATGATGCTAC
      100       110       120       130

L   T   E   L   G   A   A   T   S   I   F   L   I   A   H
TTACTGAGCTTGGTGCAGCAACTTCAATCTTTCTAATAGCACACA
      145       155       165       175

I   I   I   S   T   L   I   S   K   T   T   G   R   H   L
TAATCATTTCAACTCTTATTTCAAAAACTACCGGCCGGCATCTAC
      190       200       210       220

P   P   G   P   R   G   W   P   V   I   G   A   L   P   L
CGCCGGGGCCAAGAGGGTGGCCGGTGATCGGAGCACTTCCACTTT
      235       245       255       265

L   G   A   M   P   H   V   S   L   A   K   M   A   K   K
TAGGAGCCATGCCACATGTTTCCTTAGCTAAAATGGCAAAAAAAT
      280       290       300       310

Y   G   A   I   M   Y   L   K   V   G   T   C   G   M   A
ATGGAGCAATCATGTATCTCAAAGTTGGAACATGTGGCATGGCAG
      325       335       345       355

V   A   S   T   P   D   A   A   K   A   F   L   K   T   L
TTGCTTCTACCCCTGATGCTGCTAAAGCATTCTTGAAAACACTTG
      370       380       390       400

D   I   N   F   S   N   R   P   P   N   A   G   A   T   H
ATATCAACTTCTCCAATCGTCCACCTAATGCAGGTGCCACTCACT
      415       425       435       445

L   A   Y   N   A   Q   D   M   V   F   A   H   Y   G   P
TAGCTTATAATGCTCAAGACATGGTTTTTGCACATTATGGACCAC
      460       470       480       490

R   W   K   L   L   R   K   L   S   N   L   H   M   L   G
GATGGAAGTTGCTAAGGAAATTAAGCAACTTGCATATGCTAGGGG
      505       515       525       535
```

FIGURE 9A

```
  G   K   A   L   E   N   W   A   N   V   R   A   N   E   L
GAAAAGCCTTAGAGAATTGGGCAAATGTTCGTGCCAATGAGCTAG
      550         560         570         580

G   H   M   L   K   S   M   S   D   M   S   R   E   G   Q
GGCACATGCTAAAATCAATGTCCGATATGAGTCGAGAGGGCCAGA
      595         605         615         625

R   V   V   V   A   E   M   L   T   F   A   M   A   N   M
GGGTTGTGGTGGCGGAGATGTTGACATTTGCCATGGCCAATATGA
      640         650         660         670

I   G   Q   V   M   L   S   K   R   V   F   V   D   K   G
TCGGACAAGTGATGCTAAGCAAAAGAGTATTTGTAGATAAAGGTG
      685         695         705         715

V   E   V   N   E   F   K   D   M   V   V   E   L   M   T
TTGAGGTAAATGAATTTAAGGACATGGTTGTAGAGTTAATGACAA
      730         740         750         760

I   A   G   Y   F   N   I   G   D   F   I   P   C   L   A
TAGCAGGGTATTTCAACATTGGTGATTTTATTCCTTGTTTAGCTT
      775         785         795         805

W   M   D   L   Q   G   I   E   K   R   M   K   R   L   H
GGATGGATTTACAAGGGATAGAAAAACGAATGAAACGTTTACATA
      820         830         840         850

K   K   F   D   A   L   L   T   K   M   F   D   E   H   K
AGAAGTTTGATGCTTTATTGACAAAGATGTTTGATGAACACAAAG
      865         875         885         895

A   T   T   Y   E   R   K   G   K   P   D   F   L   D   V
CAACTACCTATGAACGTAAGGGGAAACCAGATTTTCTTGATGTTG
      910         920         930         940

V   M   E   N   G   D   N   S   E   G   E   R   L   S   T
TTATGGAAAATGGGGACAATTCTGAAGGAGAAAGACTCAGTACAA
      955         965         975         985

T   N   I   K   A   L   L   L   N   L   F   T   A   G   T
CCAACATCAAAGCACTTTTGCTGAATTTGTTCACAGCTGGTACGG
     1000        1010        1020        1030
```

FIGURE 9B

```
       D    T    S    S    S    A    I    E    W    A    L    A    E    M    M
      ACACTTCTTCTAGTGCAATAGAATGGGCACTTGCAGAAATGATGA
            1045      1055      1065      1075

K    N    P    A    I    L    K    K    A    Q    A    E    M    D    Q
      AGAACCCTGCCATTTTGAAAAAAGCACAAGCAGAAATGGATCAAG
            1090      1100      1110      1120

V    I    G    R    N    R    R    L    L    E    S    D    I    P    N
      TCATTGGAAGAAATAGGCGTTTACTCGAATCCGATATCCCAAATC
            1135      1145      1155      1165

L    P    Y    L    R    A    I    C    K    E    T    F    R    K    H
      TCCCTTACCTCCGAGCAATTTGCAAAGAAACATTTCGAAAACACC
            1180      1190      1200      1210

P    S    T    P    L    N    L    P    R    I    S    N    E    P    C
      CTTCTACACCATTAAATCTTCCTAGGATCTCGAACGAACCATGCA
            1225      1235      1245      1255

I    V    D    G    Y    Y    I    P    K    N    T    R    L    S    V
      TAGTCGATGGTTATTACATACCAAAAAACACTAGGCTTAGTGTTA
            1270      1280      1290      1300

N    I    W    A    I    G    R    D    P    Q    V    W    E    N    P
      ACATATGGGCAATTGGAAGAGATCCCCAAGTTTGGGAAAATCCAC
            1315      1325      1335      1345

L    E    F    N    P    E    R    F    L    S    G    R    N    S    K
      TAGAGTTTAATCCCGAAAGATTCTTGAGTGGAAGAAACTCCAAGA
            1360      1370      1380      1390

I    D    P    R    G    N    D    F    E    L    I    P    F    G    A
      TTGATCCTCGAGGGAACGATTTTGAATTGATACCATTTGGTGCTG
            1405      1415      1425      1435

G    R    R    I    C    A    G    T    R    M    G    I    V    M    V
      GACGAAGAATTTGTGCAGGAACAAGAATGGGAATTGTAATGGTGG
            1450      1460      1470      1480

E    Y    I    L    G    T    L    V    H    S    F    D    W    K    L
      AATATATATTAGGAACTTTGGTTCATTCATTTGATTGGAAATTAC
            1495      1505      1515      1525
```

FIGURE 9C

```
  P   S   E   V   I   E   L   N   M   E   E   A   F   G   L
CAAGTGAAGTTATTGAGTTGAATATGGAAGAAGCTTTTGGCTTAG
     1540        1550        1560        1570

A   L   Q   K   A   V   P   L   E   A   M   V   T   P   R
CTTTGCAGAAAGCTGTCCCTCTTGAAGCTATGGTTACTCCAAGGT
     1585        1595        1605        1615

L   Q   L   D   V   Y   V   P   *
TACAATTGGATGTTTATGTACCATAGCTATAGATGTGTATTGTGC
     1630        1640        1650        1660

TATAATTGCGCATGTTGTTGGTTGTAGCATGAGATATTAAAAGGA
     1675        1685        1695        1705

GTACATGAAGCGCATTGCATGAGTTTAACTTGTAGCTCCTTAATA
     1720        1730        1740        1750

TTTTAGGTATTTTTCAATTAATAAGTTCTTGTTGGTTGGGTAAAA
     1765        1775        1785        1795

AAAAAAAAAAA
     1810
```

FIGURE 9D pCGP 175

```
                                        M  V  L  L  S  E
TTGAATCCAGCTCTATCTGGCTTTAGACAATGGTGCTACTTAGTG
     10        20        30        40

L  A  A  A  T  L  I  F  L  T  T  H  I  F  I
AGCTTGCTGCAGCAACCTTAATCTTTCTAACAACACATATCTTCA
     55        65        75        85

S  T  L  L  S  I  T  N  G  R  R  L  P  P  G
TTTCAACTCTTCTTTCTATAACTAACGGCCGGCGTCTCCCGCCAG
     100       110       120       130

P  R  G  W  P  V  I  G  A  L  P  L  L  G  A
GGCCAAGAGGGTGGCCGGTGATCGGAGCACTTCCACTTTTAGGAG
     145       155       165       175

M  P  H  V  S  L  A  K  M  A  K  K  Y  G  A
CCATGCCACATGTTTCCTTAGCTAAAATGGCAAAAAAATATGGAG
     190       200       210       220

I  M  Y  L  K  V  G  T  C  G  M  V  V  A  S
CAATCATGTATCTCAAAGTTGGAACGTGTGGCATGGTAGTTGCTT
     235       245       255       265

T  P  D  A  A  K  A  F  L  K  T  L  D  L  N
CTACCCCTGATGCTGCTAAAGCGTTCTTGAAAACACTTGATCTCA
     280       290       300       310

F  S  N  R  P  P  N  A  G  A  T  H  L  A  Y
ACTTCTCCAATCGTCCACCTAATGCAGGTGCCACCCACTTAGCCT
     325       335       345       355

G  A  Q  D  M  V  F  A  H  Y  G  P  R  W  K
ATGGTGCTCAAGACATGGTTTTTGCACATTATGGACCAAGATGGA
     370       380       390       400

L  L  R  K  L  S  N  L  H  M  L  G  G  K  A
AGTTGCTAAGGAAATTAAGCAACTTACATATGCTAGGGGGGAAAG
     415       425       435       445

L  E  N  W  A  N  V  R  A  N  E  L  G  H  M
CCTTAGAAAATTGGGCAAATGTTCGTGCCAATGAGCTAGGACACA
     460       470       480       490

L  K  S  M  F  D  M  S  R  E  G  E  R  V  V
TGCTAAAATCGATGTTTGATATGAGCAGAGAAGGGGAGAGAGTTG
     505       515       525       535
```

FIGURE 10A

```
     V   A   E   M   L   T   F   A   M   A   N   M   I   G   Q
   TGGTGGCGGAGATGTTGACATTTGCCATGGCGAATATGATCGGAC
       550         560         570         580

V   I   L   S   K   R   V   F   V   N   K   G   V   E   V
   AGGTGATACTTAGCAAAAGAGTATTTGTAAATAAAGGTGTTGAGG
       595         605         615         625

N   E   F   K   D   M   V   V   E   L   M   T   T   A   G
   TAAATGAATTTAAGGACATGGTGGTAGAGTTAATGACAACAGCAG
       640         650         660         670

Y   F   N   I   G   D   F   I   P   C   L   A   W   M   D
   GGTATTTTAACATTGGTGATTTTATTCCTTGTTTAGCTTGGATGG
       685         695         705         715

L   Q   G   I   E   K   G   M   K   R   L   H   K   K   F
   ATTTACAAGGGATAGAAAAAGGAATGAAACGTTTACATAAGAAGT
       730         740         750         760

D   A   L   L   T   K   M   F   D   E   H   K   A   T   S
   TTGATGCTTTATTGACAAAGATGTTTGATGAACACAAAGCAACTA
       775         785         795         805

Y   E   R   K   G   K   P   D   F   L   D   C   V   M   E
   GCTATGAACGTAAGGGGAAACCAGATTTTCTTGATTGTGTTATGG
       820         830         840         850

N   R   D   N   S   E   G   E   R   L   S   T   T   N   I
   AAAATAGGGACAATTCTGAAGGAGAAAGGCTCAGTACAACCAACA
       865         875         885         895

K   A   L   L   L   N   L   F   T   A   G   T   D   T   S
   TCAAAGCACTCTTGCTGAATTTGTTCACAGCTGGTACAGACACTT
       910         920         930         940

S   S   A   I   E   W   A   L   A   E   M   M   K   N   P
   CTTCTAGTGCAATAGAATGGGCACTTGCAGAGATGATGAAGAACC
       955         965         975         985

A   I   L   K   K   A   Q   G   E   M   D   Q   V   I   G
   CTGCCATTTTAAAGAAAGCACAAGGAGAAATGGATCAAGTCATTG
      1000        1010        1020        1030

N   N   R   R   L   L   E   S   D   I   P   N   L   P   Y
   GAAACAATAGGCGTCTGCTCGAATCGGATATCCCAAATCTCCCTT
      1045        1055        1065        1075
```

FIGURE 10B

```
          L   R   A   I   C   K   E   T   F   R   K   H   P   S   T
        ACCTCCGAGCAATTTGCAAAGAAACATTTCGAAAGCACCCTTCTA
            1090        1100        1110        1120

P   L   N   L   P   R   I   S   N   E   P   C   I   V   D
        CACCATTAAATCTCCCTAGGATCTCGAACGAACCATGCATTGTCG
            1135        1145        1155        1165

G   Y   Y   I   P   K   N   T   R   L   S   V   N   I   W
        ATGGTTATTACATACCAAAAAACACTAGGCTTAGTGTTAACATAT
            1180        1190        1200        1210

A   I   G   R   D   P   E   V   W   E   N   P   L   E   F
        GGGCAATTGGAAGAGATCCCGAAGTTTGGGAGAACCCACTAGAGT
            1225        1235        1245        1255

Y   P   E   R   F   L   S   G   R   N   S   K   I   D   P
        TTTATCCTGAAAGGTTCTTGAGTGGAAGAAACTCGAAGATTGATC
            1270        1280        1290        1300

R   G   N   D   F   E   L   I   P   F   G   A   G   R   R
        CTCGAGGGAACGACTTTGAATTGATACCATTTGGTGCTGGACGAA
            1315        1325        1335        1345

I   C   A   G   T   R   M   G   I   V   M   V   E   Y   I
        GAATTTGTGCAGGGACAAGAATGGGAATCGTAATGGTGGAATATA
            1360        1370        1380        1390

L   G   T   L   V   H   S   F   D   W   K   L   P   S   E
        TATTAGGAACTTTGGTCCATTCATTTGATTGGAAATTACCAAGTG
            1405        1415        1425        1435

V   I   E   L   N   M   E   E   A   F   G   L   A   L   Q
        AAGTTATTGAGCTAAATATGGAAGAAGCTTTTGGATTAGCTTTGC
            1450        1460        1470        1480

K   A   V   P   L   E   A   M   V   T   P   R   L   P   I
        AGAAAGCTGTCCCTCTTGAAGCTATGGTTACTCCAAGGCTGCCTA
            1495        1505        1515        1525

D   V   Y   A   P   L   A   *
        TTGATGTTTATGCACCTTTAGCTTGAAACATGCCTTTACGTTGGT
            1540        1550        1560        1570

TTCAGTTTTGGGTAGTATAATGTTGTGGTGTTTGGCTATAGAAAT
        ATTAATAAATGCTAGTATCTTGAAGGCGCGTGCAGGGGGAGGGGG
        TTGTCTTAGATAGTAGTAATATGTTAGCCTTCCTTTTATTTCTTG
        TGATTGTGAGAATCTTGATATGTTTTCTTGAAAAAAAAAAAAAAA
```

FIGURE 10C

GENETIC SEQUENCES ENCODING A 3',5'-HYDROXYLASE AND USES THEREFOR

The present invention relates generally to genetic sequences encoding flavonoid pathway metabolising enzymes and their use such as in the manipulation of pigmentation in plants and other organisms.

The flower industry strives to develop new and different varieties of flowering plants. An effective way to create such novel varieties is through the manipulation of flower colour and classical breeding techniques have been used with some success to produce a wide range of colours for most of the commercial varieties of flowers. This approach has been limited, however, by the constraints of a particular species gene pool and for this reason it is rare for a single species to have a full spectrum of coloured varieties. Indeed, due to the limited availability of blue flowers, less than five percent of cutflowers sold through the auction system in Hollande in 1988 were blue. nongst the twelve top selling flowers, only iris and freesia offer blue coloured varieties and these varieties constitute less than four percent of all flower sales. The development of blue varieties of the major cutflower species, for example, rose, chrysanthemum, carnation and gerbera would offer a significant opportunity in both the cutflower and ornamental markets.

Flower colour is predominantly due to two types of pigment: flavonoids and carotenoids. Flavonoids contribute to a range of colours from yellow to red to blue. Carotenoids impart an orange or yellow tinge and are commonly the only pigment in yellow or orange flowers. The flavonoid molecules which make the major contribution to flower colour are the anthocyanins which are glycosylated derivatives of cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation, methylation and vacuolar pH (Forkmann, 1991).

Figure 1B:
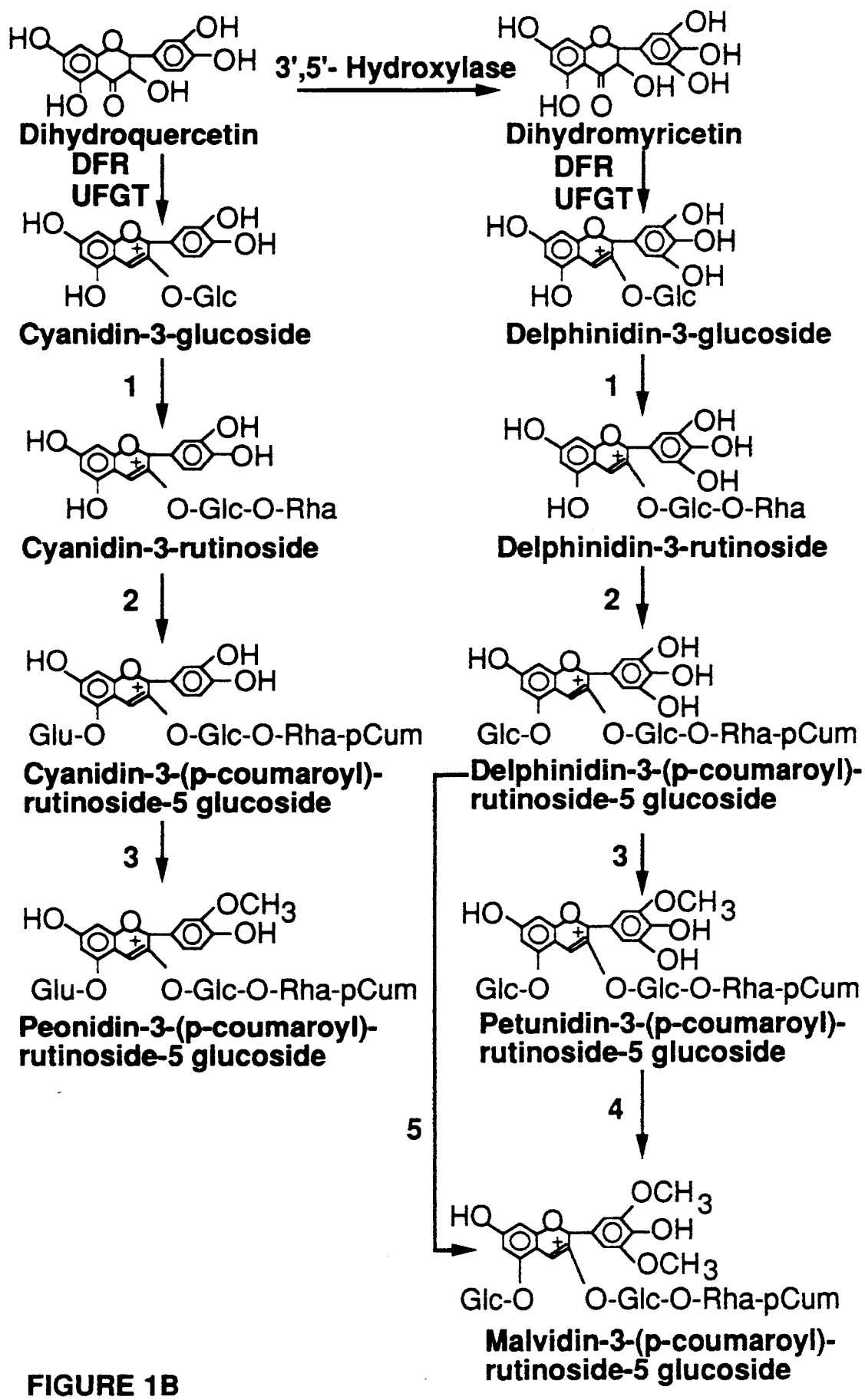

The biosynthetic pathway for the flavonoid pigments (hereinafter referred to as the "flavonoid pathway") is well established and is shown in FIG. 1 (Ebel and Hahlbrock, 1988; Hahlbrock and Grisebach, 1979; Wiering and de Viaming, 1984; Schram et al, 1984; Stafford, 1990). The first committed step in the pathway involves the condensation of three molecules of malonyl-CoA with one molecule of p-coumaroyl-CoA. This reaction is catalysed by the enzyme chalcone synthase (CHS). The product of this reaction, 2',4,4',6'-tetrahydroxychalcone, is normally rapidly isomerized to produce naringenin by the enzyme chalcone tiaranone isomerase (CHI). Naringenin is subsequently hydroxylated at the 3 position of the central ring by flavanone 3-hydroxylase (F3H) to produce dihydrokaempferol (DHK).

The B-ring of dihydrokaempferol can be hydroxylated at either the 3', or both the 3' and 5' positions, to produce dihydroquercetin (DHQ) and dihydromyricetin (DHM), respectively. Two key enzymes involved in this pathway are flavonoid 3'-hydroxylase (hereinafter referred to as 3-hydroxylase) and flavonoid 3',5'-hydroxylase (hereinafter referred to as 3',5'-hydroxylase). The 3'-hydroxylase acts on DHK to produce DHQ and on naringenin to produce eriodictyol. The 3',5'-hydroxylase is a broad spectrum enzyme catalyzing hydroxylation of naringenin and DHK in the 3' and 5' positions and of eriodictyol and DHQ in the 5' position (Stotz and Forkmann, 1982), in both instances producing pentahydroxyflavanone and DHM, respectively. The pattern of hydroxylation of the B-ring plays a key role in determining petal colour.

Flavonoid 3'-hydroxylation in microsomal extracts requires NADPH and $O_2$ as well as the aglycone of either naringenin or DHK. The parsley cell culture enzyme has been well studied (Hagmann et al, 1983). Inhibition by carbon monoxide, cytochrome c and $NADP^+$ indicated that the enzyme is a cytochrome P450-dependent enzyme. A similar enzyme activity has been demonstrated in maize (Larson and Bussard, 1986). The 3',5'-hydroxylase is also of the cytochrome P450 class of enzymes. Cytochrome P450 enzymes are widespread in nature and have been characterised in vertebrates. insects, yeasts, fungi, bacteria and one plant. Sequences of at least 154 cytochrome P450 genes have been determined and the genes grouped into 27 different gene families (Nebert et al, 1991). Within a single family, the P450 protein sequences are generally >40% identical whilst sequences within the same subfamily are >46% identical (Nebert et al, 1991). Information on plant cytochromes P450 is limited.

The ability to control in plants 3' or 3',5'-hydroxylase activity, or other enzymes involved in the flavonoid pathway, would provide a means to manipulate petal colour thereby enabling a single species to express a broader spectrum of flower colours. In accordance with the present invention, the genetic sequences encoding flavonoid pathway enzymes such as 3',5'-hydroxylase have been identified and cloned. These recombinant sequences permit the modulation of DHK metabolism as well as the metabolism of other substrates such as DHQ, naringenin and eriodictyol, thereby determining the hydroxylation pattern of the anthocyanins and providing a means to manipulate petal colour. The present invention, however, extends beyond flowers to fruit and vegetable plants and to leaves of, for example, ornamental plants.

Accordingly, one aspect of the present invention provides a nucleic acid isolate comprising a sequence of nucleotides encoding, or complementary to a sequence encoding, a dihydrokaempferol (DHK) hydroxylating enzyme, or a derivative or part thereof.

For convenience and by way of shorthand notation only, reference herein to "DHK hydroxylating enzyme" includes flavonoid pathway hydroxylating enzymes acting on one or more of the following: DHK, DHQ, naringenin. eriodictyol.

Preferably, the DHK hydroxylating enzyme is 3',5'-hydroxylase. However, the methods employed to clone the genetic sequences encoding this enzyme could be employed to isolate other genetic sequences encoding enzymes such as the 3'-hydroxylase. Accordingly, reference herein to the isolation and cloning of 3',5'-hydroxylase should be taken to include reference to other flavonoid hydroxylating enzymes such as 3'-hydroxylase.

By the term "nucleic acid isolate" is meant a genetic sequence in a non-naturally occurring condition. Generally, this means isolated away from its natural state or formed by procedures not necessarily encountered in its natural environment. More specifically, it includes nucleic acid molecules formed or maintained in vitro, recombinant or synthetic molecules and nucleic acids in combination with heterologous nucleic acids. It also extends to naturally occurring sequences following at least a partial purification relative to other nucleic acid sequences.

By "genetic sequences" as used herein is meant any contiguous series of nucleotide bases specifying directly, or via a complementary series of bases, a sequence of amino acids in a DHK hydroxylating enzyme, for example, 3',5'-hydroxylase. The nucleic acid or its complementary form may encode the full length enzyme or a derivative or part thereof. By "derivative" is meant any single or multiple amino acid substitutions, deletions, and/or additions relative to the naturally occurring enzyme. In this regard, the nucleic acid includes the naturally occurring nucleotide sequence encoding 3',5'-hydroxylase or may contain single or multiple nucleotide substitutions, deletions and/or additions to said naturally occurring sequence. The nucleic acid sequences contemplated herein also encompass oligonucleotides useful as genetic probes or as "antisense" molecules capable of regulating expression of the corresponding gene in a plant. Accordingly, when the nucleic acid or its complementary form encodes a "part" of the 3',5'-hydroxylase, then such a nucleic acid molecule may be useful as an oligonucleotide probe, primer for polymerase chain reactions or in various mutagenic techniques.

Amino acid insertional derivatives of the DHK hydroxylating enzyme and in particular the 3',5'-hydroxylase of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the 3',5'-hydroxylase is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional. insertional or deletional variants are conveniently described, for example, in Sambrook et al., (1989).

Other examples of recombinant or synthetic routants and derivatives of the 3',5'-hydroxylase of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of the 3',5'-hydroxylase and also to any amino acid derivative described above.

The nucleic acids of the present invention may be ribonucleic acids or deoxyribonucleic acids, single or double stranded and linear or covalently closed circular molecules. Preferably, the nucleic acid molecule is cDNA. The present invention also extends to other nucleic acid molecules which hybridise under low, preferably under medium and most preferably under high stringency conditions with the nucleic acid molecules contemplated by the present invention. Expressed in alternative terms, the present invention extends to a nucleic acid molecule having a nucleotide sequence set forth in FIG. 9 or 10 or to a molecule having at least 35%, more preferably at least 45%, even more preferably at least 55%, still more preferably at least 65-70%, and yet even more preferably greater than 85% similarity at the level of nucleotide or amino acid sequence and wherein the nucleic acid encodes or is complementary to a sequence which encodes an enzyme having 3',5'-hydroxylase activity. It should be noted, however, that nucleotide or amino acid sequences may have similarities below the above given percentages and yet still encode DHK hydroxylating enzymes and such molecules may still be considered in the scope of the present invention where they have conserved regions of hornology. The present invention father extends to nucleic acid molecules in the form of oligonucleotide primers capable of hybridising to a portion of the nucleic acid molecules contemplated above under low, preferably under medium and most preferably under high stringency conditions.

The nucleic acid molecules contemplated herein may exist alone or in combination with a vector molecule and preferably an expression-vector. Such vector molecules replicate and/or express in eukaryotic and/or prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may be introduced into the cell by any number of means such as by electroporation or *Agrobacterium* mediated transfer.

The present invention is exemplified using nucleic acid sequences derived from petunia since this represents the most convenient and preferred source of material to date. However, one skilled in the art will immediately appreciate that similar sequences can be isolated from any number of sources such as other plants or certain microorganisms. The genetics of the 3'-hydroxylases is known in flowers of *Antirrhinum*, *Verbena* and *Petunia* and in seedlings and aleurone layers of seeds of maize (Heller and Forkmann, 1988). The gene eos controls 3'-hydroxylase in *Antirrhinum* (Forkmann and Storz, 1981), while the Ht1 and Pr genes control similar enzymes in *Petunia* (Stotz et al, 1985) and in maize aleurone layer, respectively (Larson and Bussard, 1986). Chemogenetic studies of *Verbena hybrida*, for example, have shown that in this plant the hydroxylation of the B-ring of anthocyanins in both the 3' and 5' position is controlled by one gene (Beale, 1940). Enzyme activity for 3',5'-hydroxylation is only present in flower extracts of delphinidin-producing strains (Stotz and Forkmann, 1982). NADPH-dependent microsomal enzyme activity for hydroxylation in the 3' and 5' position was also demonstrated in flower extracts of *Callistephus* and *Lathyrus*(Forkmann, 1991). As in *V. hybrida*, enzyme activity for the 3 ',5'-hydroxylation of tiaranones and dihydroflavonols was only found to be present in flower extracts of those strains which contain 3',4',5'-hydroxylated flavonoid compounds (or methylated derivatives of them) in the flowers. Thus, formation of the 3',4',5'-hydroxylated flavonoids is clearly dependent on flavonoid 3',5'-hydroxylase activity.

The genes encoding 3',5'-hydroxylase have been identified in a number of ornamental plants including *Callistephus* (R), *Petunia* (Hf1, HF2) and *Verbena* (P) by the presence of the respective routants unable to produce delphinidin. Moreover, the respective enzyme activities have been demonstrated (Forkmann, 1991). The 3',5'-hydroxylase was also considered to be a microsomal cytochrome P450 enzyme (Heller and Formann, 1988). However, there are no published reports of the cloning of a 3',5'-hydroxylase gene from these or other plant species.

Other plant species capable of producing 3',4',5'-hydroxylated flavonoids or their derivatives include hydrangea (Takeda et al, 1985), delphinium (Asen et al, 1975), lisianthus (Asen et al, 1986), tomato (yon Wettstein-Knowles, 1968) and potato (Harborne and Simmonds, 1962). These species, or other plants capable of producing 3',4',5'-hydroxylated flavonoids, would also be suitable sources for the isolation of a 3',5'-hydroxylase gene. All such nucleic acid sequences encoding directly or indirectly a flavonoid pathway enzyme (e.g. 3,5'-hydroxylase) are encompassed by the present invention regardless of their source.

Likewise, the gene cloning strategy outlined here may be used to isolate a 3',5'-hydroxylase gene from other plants which produce 3',4',5'-hydroxylated flavonoids. Clones and oligonucleotides herein disclosed may be used to detect, isolate and clone similar genetic sequences using the same technology as herein described, although some minor modification(s) to the experimental procedures may be required. All such minor variations are encompassed by the present invention. Examples of other suitable sources of enzymes such as 3',5'-hydroxylase include, but are not limited to, verbena, delphinium, grape, iris, freesia, hydrangea, cyclamen, potato, pansy and eggplant.

In accordance with the present invention, a nucleic acid sequence encoding a DHK hydroxylating enzyme such as 3',5'-hydroxylase may be introduced into and expressed in a transgenie plant thereby providing a means to convert DHK and/or other suitable substrates, if synthesized in the plant cell, ultimately into anthocyanin derivatives of anthocyanidins such as delphinidin, petunidin or malvidin. The production of these anthocyanins contributes to the production of a variety of shades of blue colour or blue-like colour. Expression of the nucleic acid sequence in the plant may be constitutive, inducible or developmental.

Accordingly, another aspect of the present invention provides a method for producing a transgenie plant capable of expressing a recombinant DHK hydroxylating enzyme or active routants or derivatives thereof, said method comprising introducing into a cell of a suitable plant a nucleic acid molecule which comprises a sequence of nucleotides encoding said DHK hydroxylating enzyme, under conditions permitting the eventual expression of said nucleic acid molecule, regenerating a transgenie plant from the cell and growing said transgenie plant for a time and under conditions sufficient to permit the expression of the nucleic acid.

In a preferred embodiment, the present invention contemplates a method for producing a transgenie flowering plant exhibiting altered inflorescence properties, said method comprising introducing into a cell of a suitable plant the nucleic acid sequence of the present invention under conditions permitting the eventual expression of said nucleic acid sequence, regenerating a transgenic plant from the cell and growing said transgenie plant for a time and under conditions sufficient to permit the expression of the nucleic acid sequence into the DHK hydroxylating enzyme.

Preferably, the DHK hydroxytating enzyme is 3', 5'-hydroxylase, is developmentally regulated and the altered inflorescence includes the production of blue or red flowers or other colour shades depending on the physiological conditions of the recipient plant. By "suitable plant" is meant a plant capable of producing a substrate for the 3',5'-hydroxylase enzyme, and possessing the appropriate physiological properties and genotype required for the development of the colour desired. This may include but is not limited to rose, petunia, carnation, chrysanthemum and gerbera. In certain plant species it may be preferable to select a "high pH line", such being defined as a variety having a higher than average petal vacuolar pH. The origin of the recombinant 3',5'-hydroxylase or its routants and derivatives are as hereinbefore described and include enzymes of petunia, verbena, delphinium, grape, iris, freesia, hydrangea, cyclamen, potato, pansy or eggplant origin.

One skilled in the art will immediately recognise the variations applicable to this method such as increasing or decreasing the expression of the enzyme naturally present in a target plant. This would lead to differing shades of colours such as different shades of blue or red.

In order to decrease activity of a target enzyme, such as 3',5'-hydroxylase, the nucleic acid sequence encoding this enzyme or various parts thereof could be used in the antisense orientation. Although not wishing to limit the present invention to any one theory, it is probable that such an antisense nucleic acid sequence would form a duplex with all or part of the naturally occurring mRNA specified for the enzyme thus preventing translation of the mRNA into active enzyme. Alternatively, ribozymes could be used to inactivate target nucleic acid sequences.

Accordingly, the present invention extends to a method for producing a transgenie plant capable of expressing a recombinant dihydrokaempferol (DHK) hydroxylating enzyme or which directs transcription of a nucleic acid sequence which is substantially complementary to all or a part of a mRNA molecule translatable to DHK hydroxylating enzyme, said method comprising introducing into a cell of a suitable plant the nucleic acid isolate according to claim 1 or 6 under conditions permitting the eventual expression of said nucleic acid isolate, regenerating a transgenie plant from the cell and growing said transgenie plant for a time and under conditions sufficient to permit the expression of the nucleic acid isolate. In this embodiment, suitable recipient plants extend to inter alia, iris, tulip, lily, lisianthus, freesia, delphinium, limonium and pelargonium.

The above methods of producing transgenie plants, therefore, extend to the alternative of introducing a gene or DNA fragment encoding an antisense mRNA or oligonucleotide to all or a portion or region of a sequence of nucleotides encoding, or complementary to a sequence encoding, a 3′,5′-hydroxylase.

Consequently, the present invention extends to all transgenie plants containing all or part of the nucleic acid sequence of the present invention, or antisense forms thereof and/or any homologues or related forms thereof and in particular those transgenie plants which exhibit altered inflorescence properties. The transgenie plants, therefore, contain a stably introduced nucleic acid molecule comprising a nucleotide sequence encoding or complementary to a sequence encoding a DHK hydroxylating enzyme and in particular high pH plant lines carrying such introduced nucleic acid molecules as referred to above. The invention also extends to seeds from such trarmgenic plants. Such seeds, especially if coloured, will be useful as proprietary tags for plants.

A further aspect of the present invention is directed to recombinant forms of the DHK hydroxylating enzymes and in particular recombinant 3′,5′-hydroxylase. The recombinant forms of the enzymes will provide a source of material for research to develop, for example, more active enzymes and may be useful in developing in vitro systems for production of coloured compounds.

Another aspect of the present invention contemplates a method for cloning a nucleic acid molecule comprising a sequence of nucleotides which encode or are complementary to a sequence which encode, a cytochrome P450 molecule or like molecule from a plant, said method comprising amplification of cytochrome P450 nucleotide sequences or complementary sequences from a suitable preparation of nucleic acid molecules from cells of said plant by polymerase chain reactions using one or more oligonucleotide primers, said primers having a nucleotide sequence derived from one or more consensus sequences of known microsomal cytochrome P450 molecules.

In a related embodiment, the method for cloning the cytochrome P450 nucleic acid molecules or their complementary sequences comprises selecting from a suitable eDNA library a clone capable of hybridising to one or more oligonucleotide primers corresponding to one or more consensus sequences or known cytochrome P450 molecules Preferably, one of the consensus sequences is from the haem-binding domain of cytochrome P450 molecules and is more preferably F(G,S) XGXRXCXG (SEQ. ID NO. 1) (wherein X is any arnino acid) or is PGFAGRRICPG (SEQ. ID. No. 1). In a most preferred embodiment, the nucleotide sequences to be cloned encode or are complementary to sequences which encode, a DHK hydroxylating enzyme, and in particular 3′,5′-hydroxylase. Even more preferably, the 3′,5′-hydroxylase is as hereinbefore described and, more particularly, has an amino acid sequence or is encoded for by a sequence of nucleotides substantially as set forth in FIGS. 9 or 10 or has similarity thereto as defined above.

The present invention is further described by reference to the following nonlimiting /Figures and Example.

FIGS. 1(A) and (B) are schematic representations of the biosynthesis pathway for the flavonoid pigments. Enzymes involved in the first part of the pathway have been indicated as follows: PAL=Phenylalanine ammonia-lyase; C4H =Cinnamate 4-hydroxylase; 4CL=4-coumarate: CoA ligase; CHS =Chalcone synthase; CHI =Chalcone flavanone isomerase; F3H =Flavanone 3-hydroxylase; DFR =Dihydroflavonol-4-reductase; UFGT =UDP-glucose: flavonoid-3-O-glucosyltransferase. The later steps correspond to conversions that occur in P. hybrida flowers and include: 1=addition of a rhamnose sugar to the glucosyl residue of cyanidin-3-glucoside and delphinidin-3glucoside; acylation and 5-O-glucosylation; 3=3′methylation; 4=5′ methylation; 5=3′5′methylation.

Figure 2A:
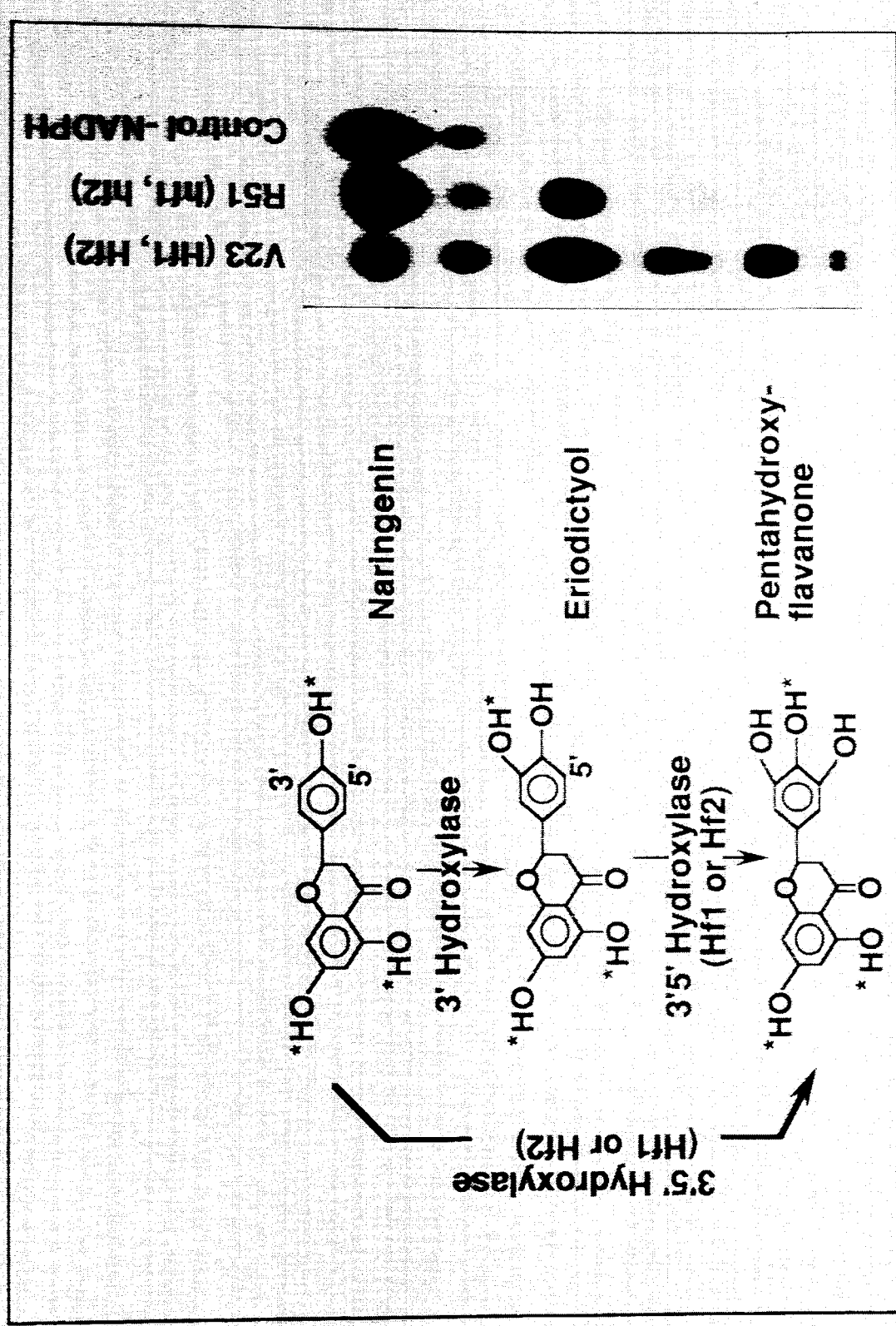

FIG. 2(A) shows 3′,5′-hydroxylase activity in petal extracts of P. hybrida cv V23 (Hf1/Hf1, Hf2/Hf2) and the lack of 3′,5′-hydroxylase activity in P. hybrida cv R51 (hf1/hf1, hf2/hf2). 3′,5′-hydroxylase activity was detected by conversion of 3H-naringenin to the 3 ′- and 3′,5 ′-hydroxylated derivatives eriodictyol and pentahydroxyfiavanone. On the left-hand side of the figure the biochemical structures of the substrate, naringenin and the product of the 3′-hydroxylase reaction, eriodictyol and the 3′,5′-hydroxylase reaction, pentahydroxyflavanone are shown. The location of the substrate and the hydroxylated products on the TLC plate is indicated on the right-hand side of the Figure which shows from left to right the autoradiographs of the reaction products produced by petal extracts of flowers from P. hybrida cv V23 and P. hybrida cv RS1 and the control showing no hydroxylation of naringenin when NADPH is omitted from the reaction mixture.

Figure 2B:
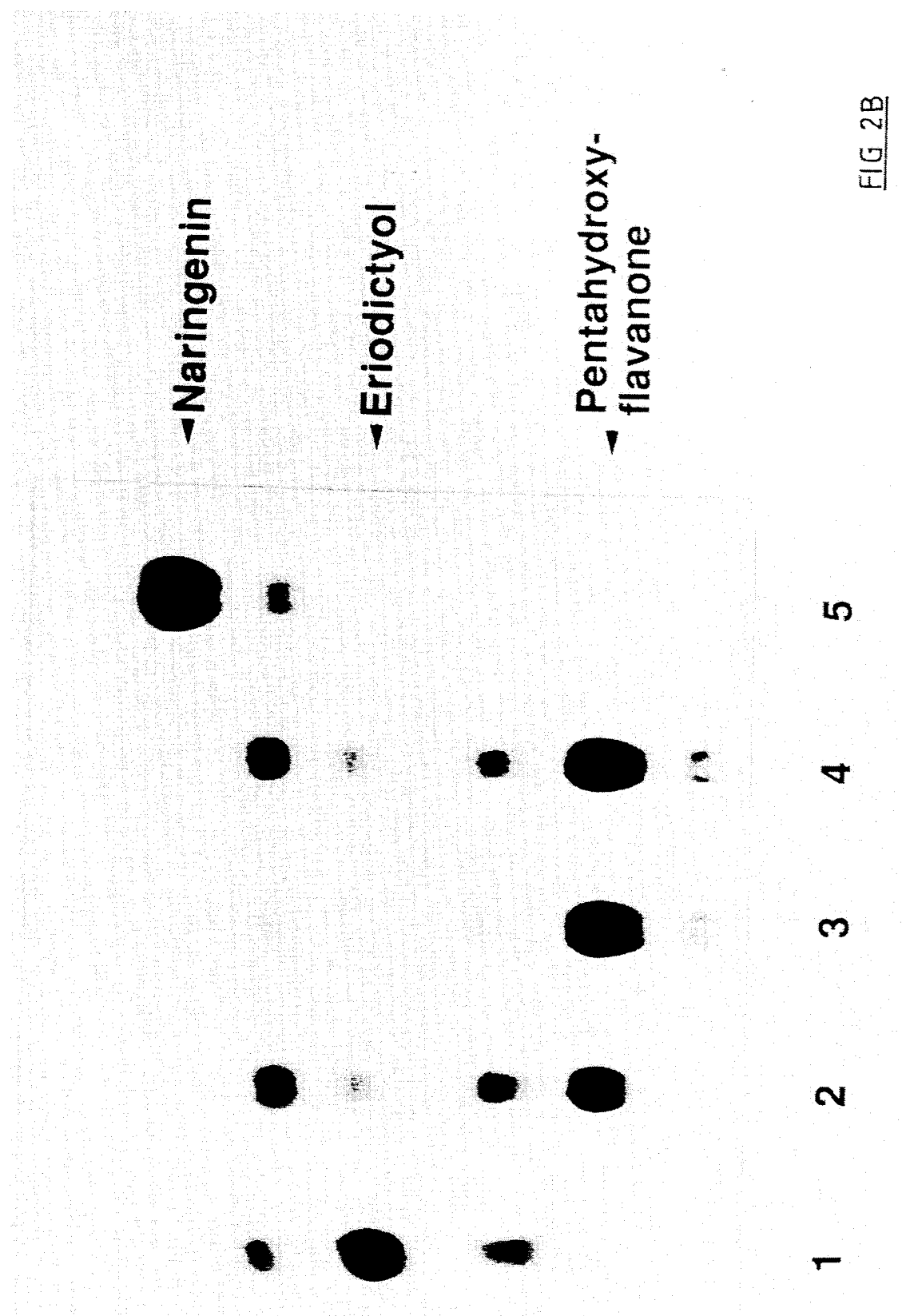

FIG. 2(B) shows 3′,5′-hydroxylase activity in petal extracts of P. hybrida cv Old Glory Blue (OGB) flowers at different developmental stages. From left to right the autoradiographs of the TLC plates show (1) Stage 1 flowers [Unpigmented, closed bud (<25 mm in length)]: limited conversion of naringenin to the 3′,5′-hydroxylareal derivative pentahydroxyflavanone, (2) Stage 2 flowers [Pigmented, closed bud (25–35 mm in length)]: increased conversion to pentahydroxyflavanone indicative of higher 3′,5′-hydroxylase levels, (3) Stage 3 flowers: [Dark purple bud with emerging corolla (>35 mm in length)]: maximal 3′5′-hydroxylase activity, (4) Stage 4 flowers [Dark purple opened flower pre-anther dehiscence (>50 mm in length)]: maximal 3′,5′-hydroxylase activity (5) Stage 5 flowers [Fully opened flower with all anthers dehisced]: no detectable 3′,5′-hydroxylase levels.

FIG. 3(A) is a schematic representation of a mRNA molecule encoding a cytochrome P450. The shaded region indicates the relative position of sequences encoding the haem binding domain. A consensus amino acid sequence for the most conserved region of this domain has been shown using single letter code. Amino acids that are present in 100% of cytochrome P450 sequences present in the SWISS-PROT database have been boxed and X indicates positions where there is a low level of sequence conservation.

FIG. 3(B) shows the position of oligos used for PCR amplification of cytochrome P450 molecules pCGP450 and pCGP454 from eDNA library #1. Oligos 1 and 3 covered sequences in the conserved haem binding domain while oligos 2 and 4 corresponded to the pBluescript (Stratagene) -20 and reverse primer sequences, respectively. Oligos 1 and 2 were used to synthesize the eDNA insert in pCGP450; oligos 3 and 4 were used the synthesize the eDNA insert in pCGP454. Representation of a generalized eDNA molecule is identical to that shown in FIG. 3A; vector sequences have been indicated by light shading.

Figure 4A:
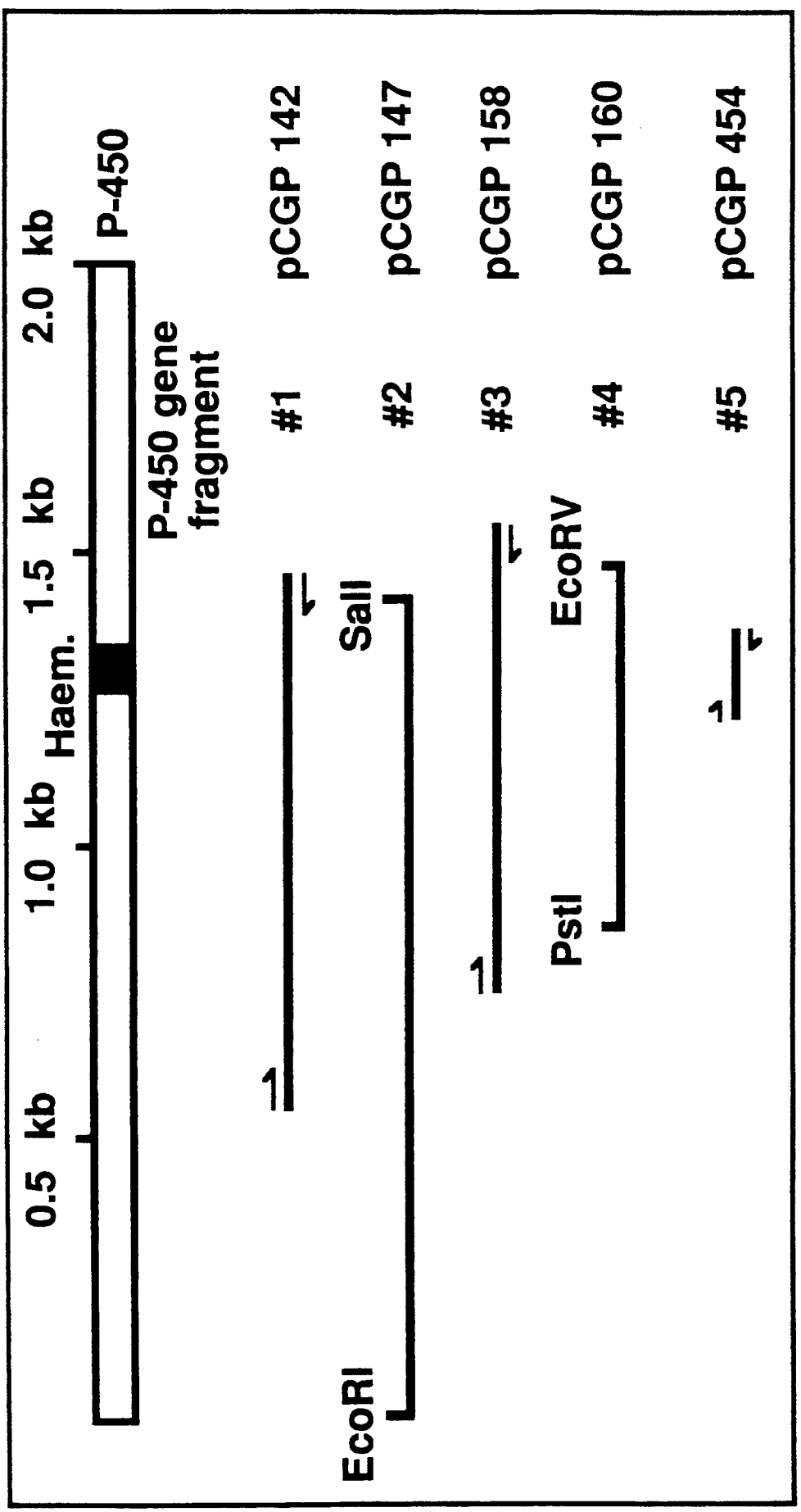
Figure 4C:

FIG. 4(A) is a schematic representation of DNA fragments used to probe cDNA library #1 to identify cytochrome P450 homologues, including pCGP174 and pCGP175. P450: generalized cytochrome P450 cDNA clone with the haem-binding domain (Haem) indicated by the shaded box; Fragment 1: a 900 bp fragment was obtained by PCR with oligos 5 and 6 using pCGP142 DNA as template; Fragment 2: a 1.3 kb fragment was isolated from a Sn. LI-F2.,oRI digest of pCGP147; Fragment 3: a 750 bp fragment was obtained by PCR with oligos 4 and 7 using pCGP158 DNA as template; Fragment 4: a 670 bp fragment was isolated from a PstI-EcoRV digest of pCGP160; Fragment 5: a 150 bp fragment was obtained by PCR with oligos 3 and 4 using pCGP454 DNA as template. All purified fragments were labelled with 32P-dCTP as described in the Materials and Methods.

FIGS. 4(B) to (H) show partial nucleotide sequences and the corresponding predicted amino acid translation products for the cDNA inserts from (i) pCGP142, (SEQ. ID No. 23), (ii) pCGP147 (SEQ. ID. No. 24), (iii) pCGP158 (SEQ. ID No. 25), (iv) pCGP160 (SEQ. No. 26) and (v) pCGP454 (SEQ. ID No. 2). The regions used to probe cDNA library #1 to isolate pCGP174 and pCGP175 have been delineated by arrowheads.

Figure 5A:
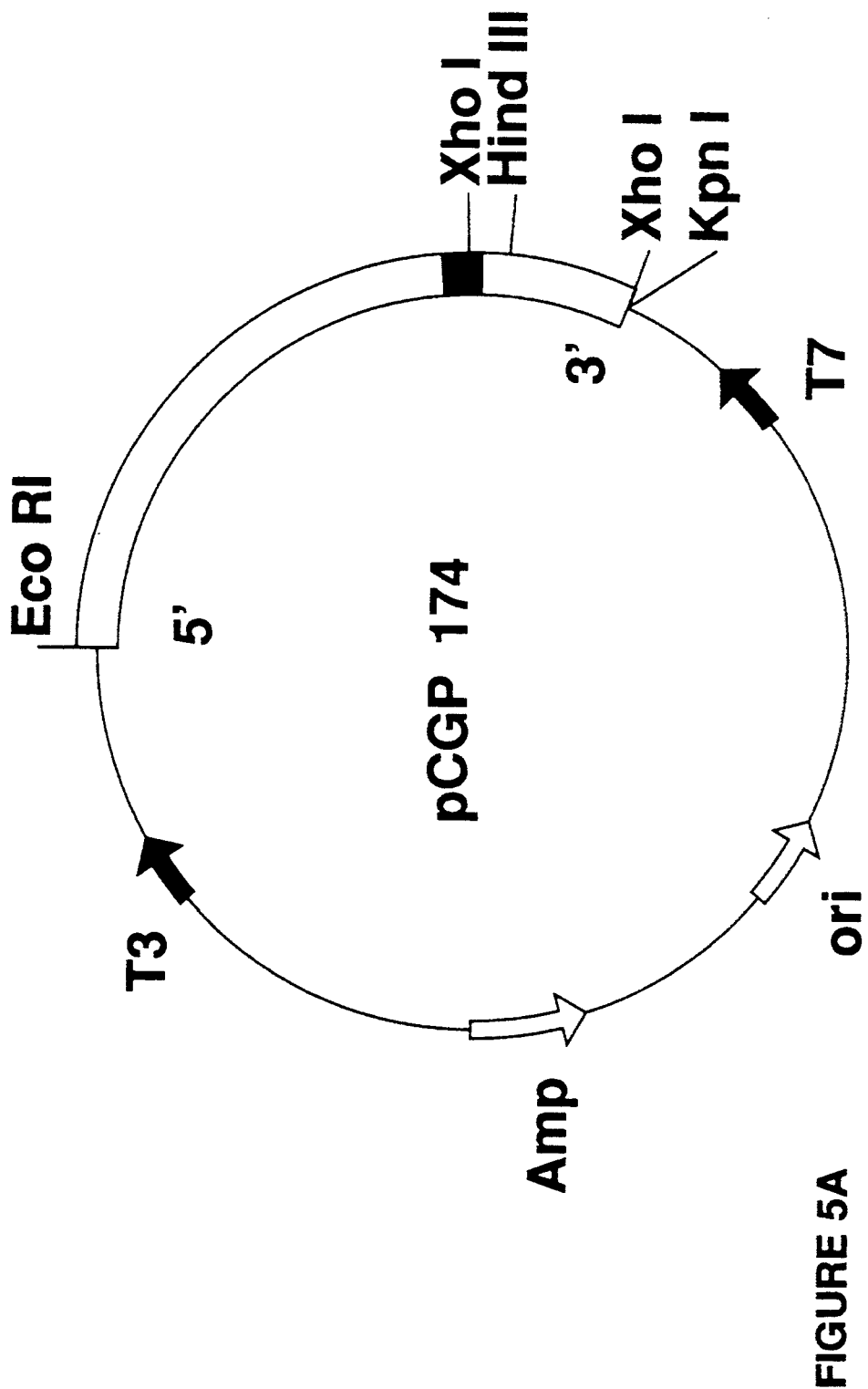
Figure 5B:
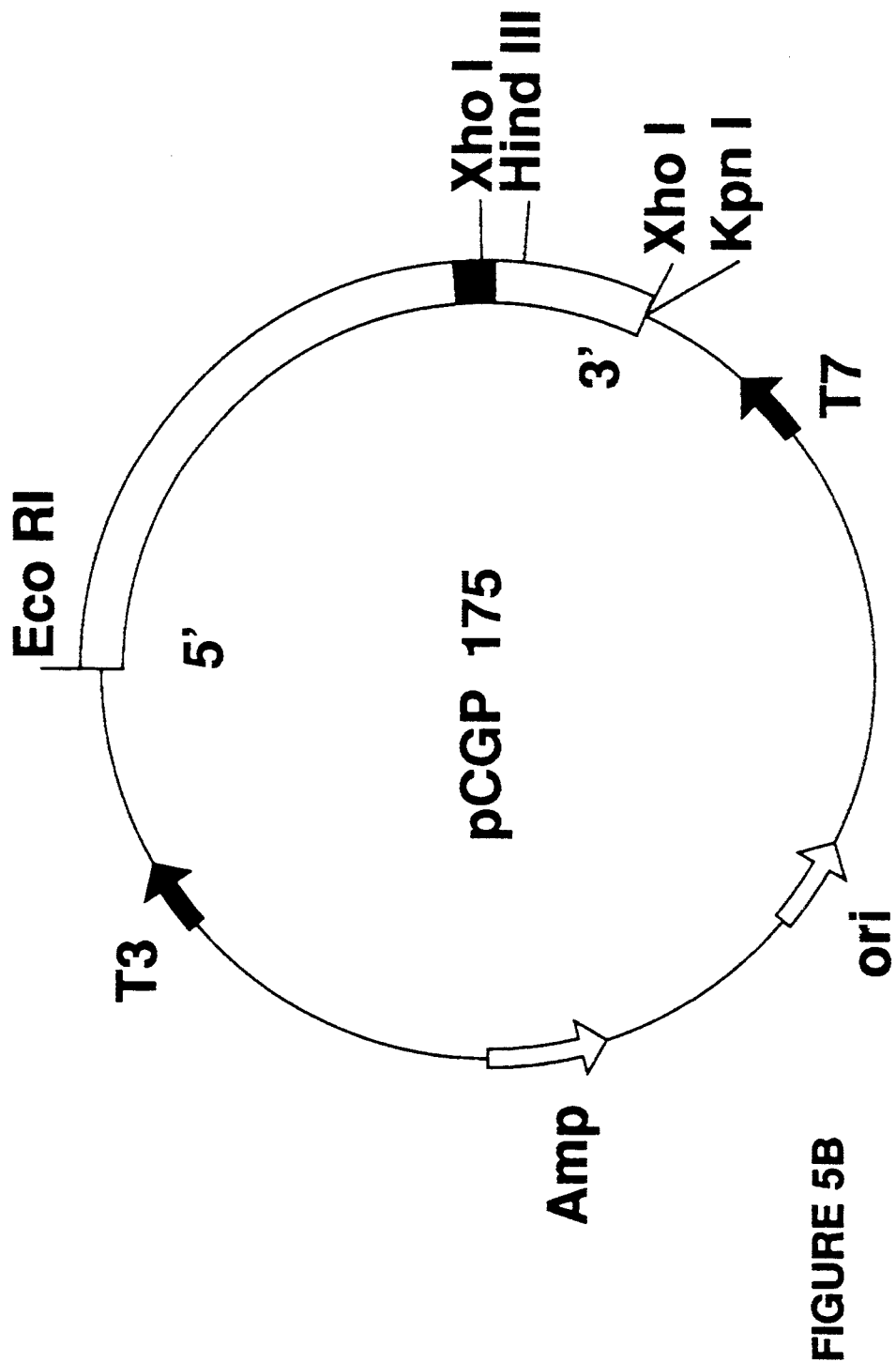

FIGS. 5 (A) and (B) are diagrammatic representations of plasmids pCGP174 and pCGP175, respectively. The eDNA inserts are indicated as open boxes with the region encoding the putative haem-binding domain shown as a shaded region. An EcoRI site is at the 5'-end and a XhoI site is at the 3'-end of both eDNA inserts.

Figure 6A:
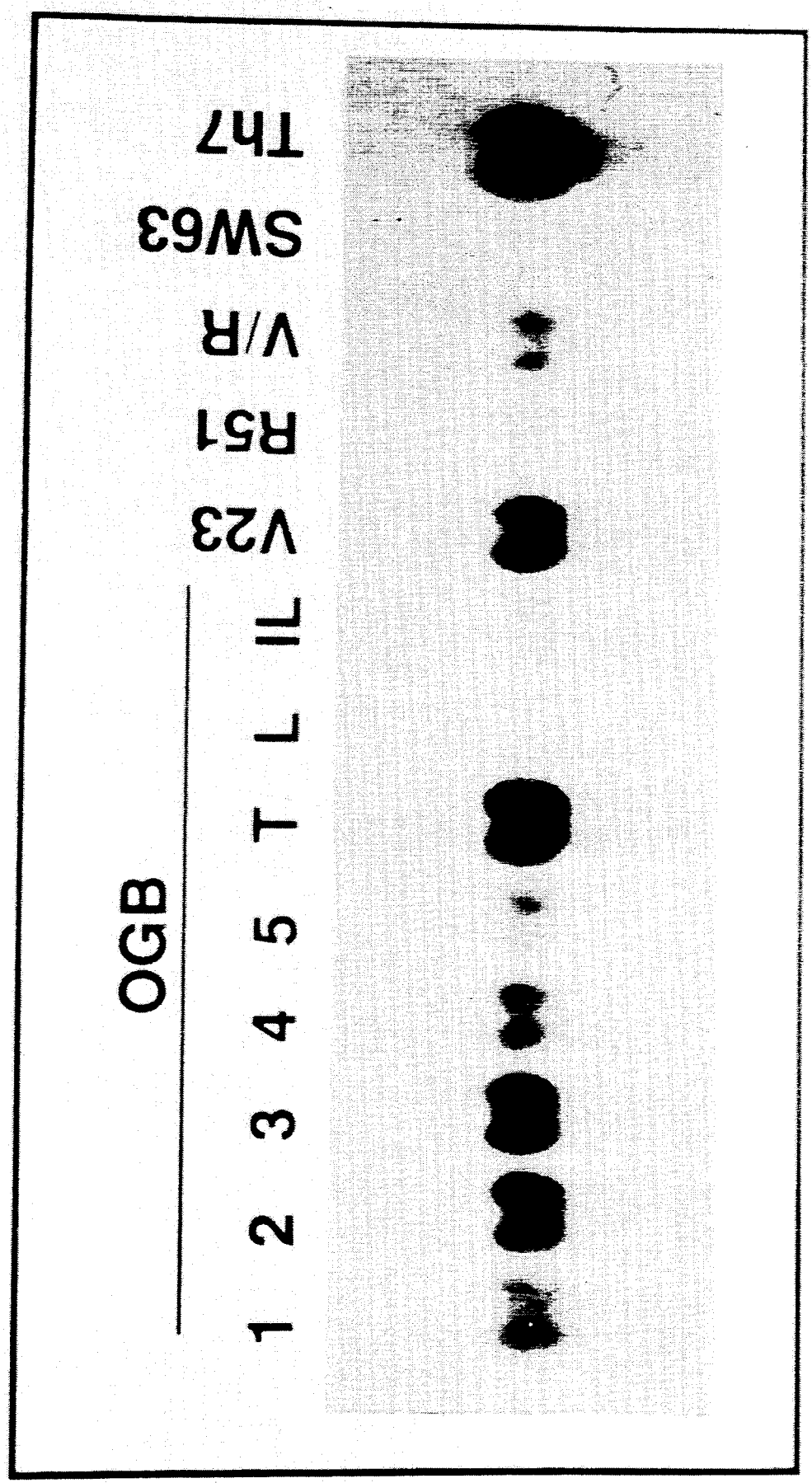

FIG. 6(A) is an autoradiograph of an RNA blot probed with the 3' region of the pCGP174 cDNA insert. Each lane contained a 20 μg sample of total RNA isolated from the following petunia tissues- 1-5: OGB limb tissue of flowers at the five (1-5) different stages of flower development described in the Materials and Methods; T: OGB tube tissue from stage 3-4 flowers; L: leaf tissue from 6 week old OGB seedlings; IL: glucose/high light treated leaf tissue from 6 week old OGB seedlings; V23:V23 limb tissue from stage 3-4 flowers; R51: R51 corolla tissue from stage 3-4 flowers; VR: petal limb tissue from stage 3-4 flowers of the V23xR51 F1 hybrid; Sw63: petal limb tissue from stage 3-4 flowers of Sw63; Th7: petal limb tissue from stage 3-4 flowers of Th7.

Figure 6B:
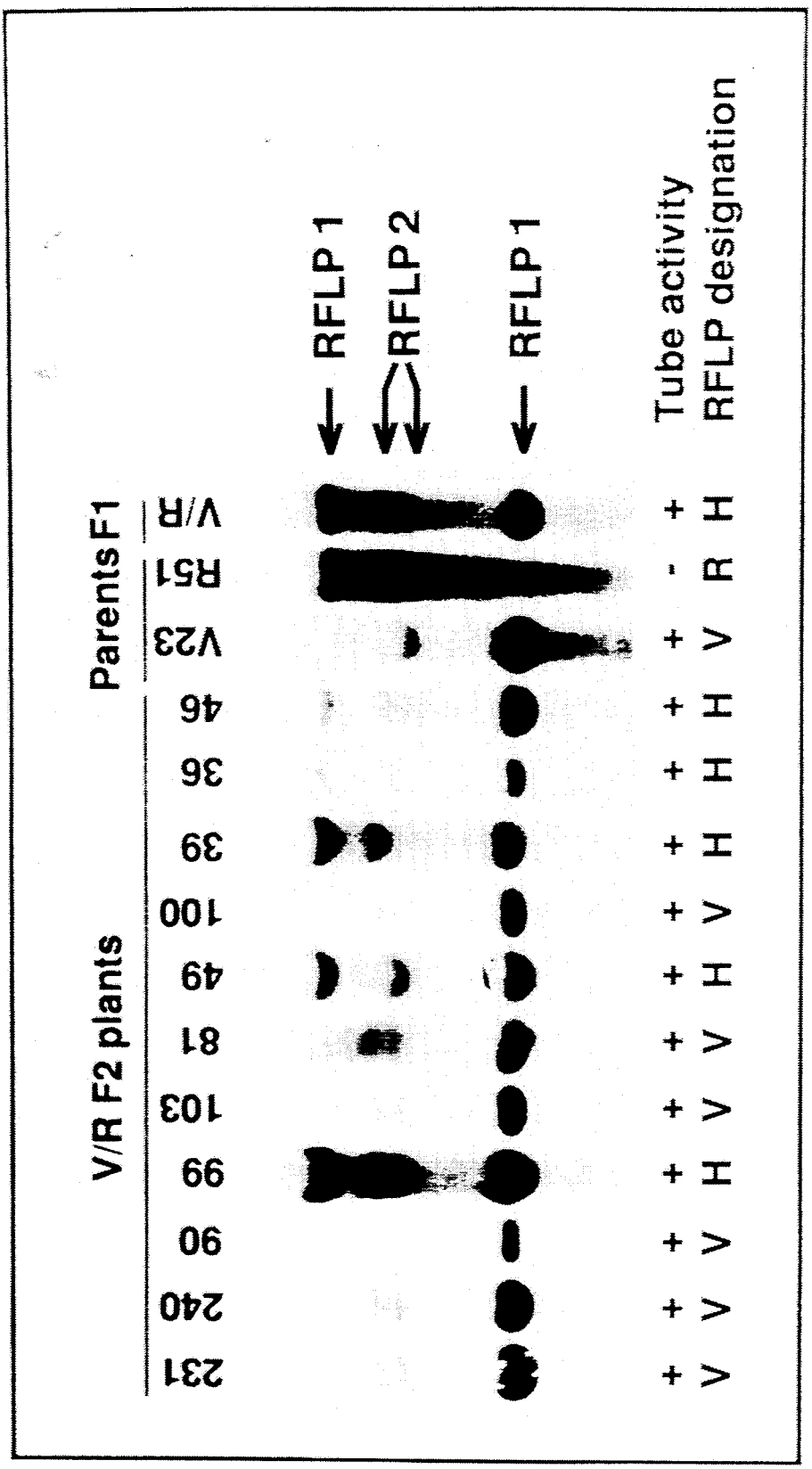

FIG. 6(B) is a representative autoradiograph from the RFLP analysis of the V23xR51 (V/R) F2 plants. Xbal digested genomic DNA was probed with the 3' region of pCGP174. The V23 fragment that hybridized strongly to the probe was detected in all F2 plants that had 3',5'-hydroxylase activity in tube tissue of the flowers (+). RFLP designation for the strongly hybridizing bands (RFLP#1) has been indicated for the various plants. V: V23-like RFLP, R: R51-like RFLP, H: heterozygotic (VR).

Figure 7A:
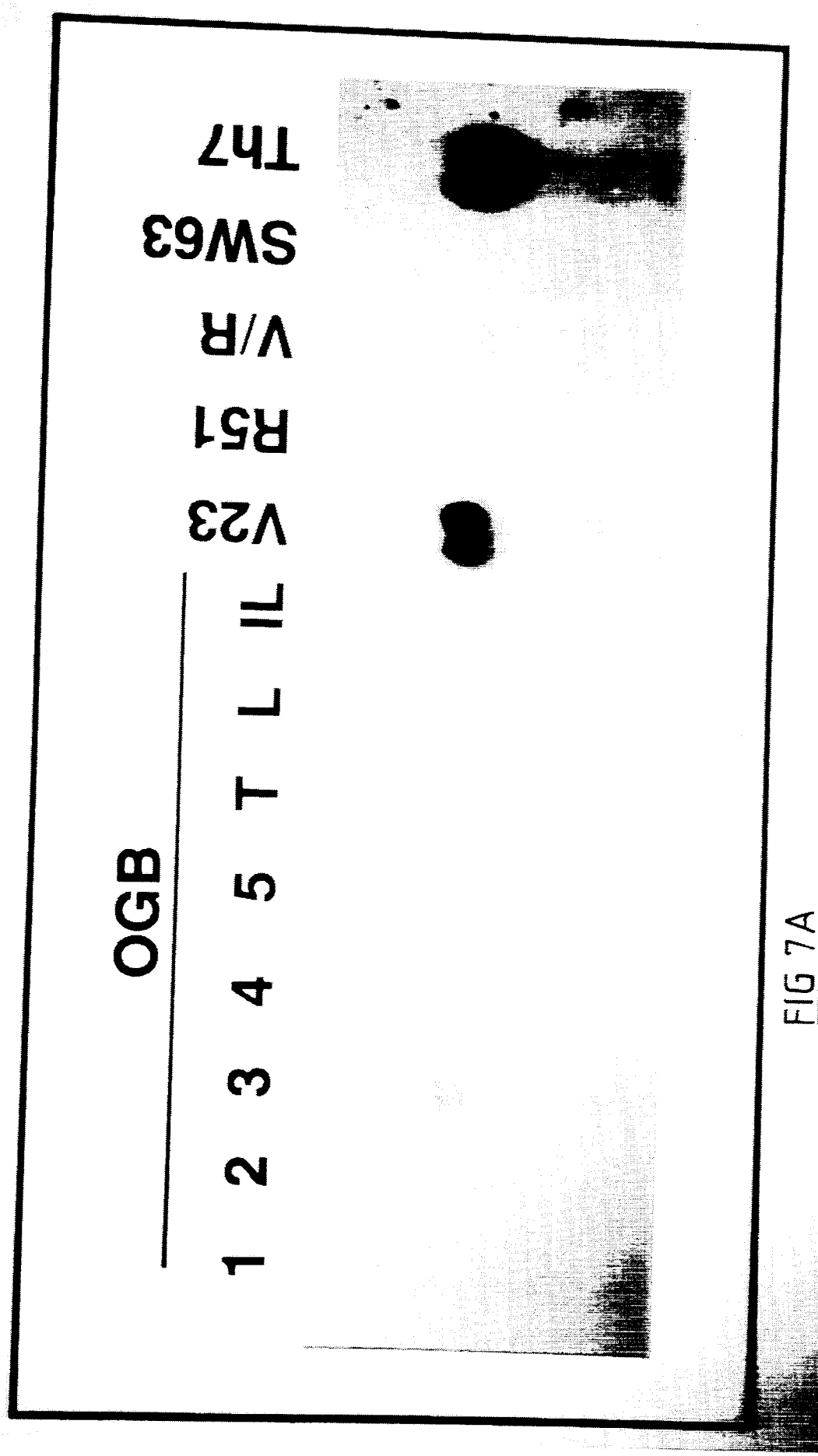

FIG. 7(A) is an autoradiograph of a RNA blot probed with the 3' region of the pCGP175 cDNA insert. Each lane contained a 20 lag sample of total RNA isolated from the following - 1-5: OGB limb tissue of flowers at the five (1-5) different stages of flower development described in the Materials and Methods; T: OGB tube tissue from stage 3-4 flowers; L: leaf tissue from 6 week old OGB seedlings; IL: glucose/high light treated leaf tissue from 6 week old OGB seedlings; V23:V23 limb tissue from stage 3-4 flowers; R51:RS1 corolla tissue from stage 3-4 flowers; VR: petal limb tissue from stage 3-4 flowers of the V23xR51 F1 hybrid; Sw63: petal limb tissue from stage 3-4 flowers of Sw63; Th7: petal limb tissue from stage 3-4 flowers of Th7.

Figure 7B:
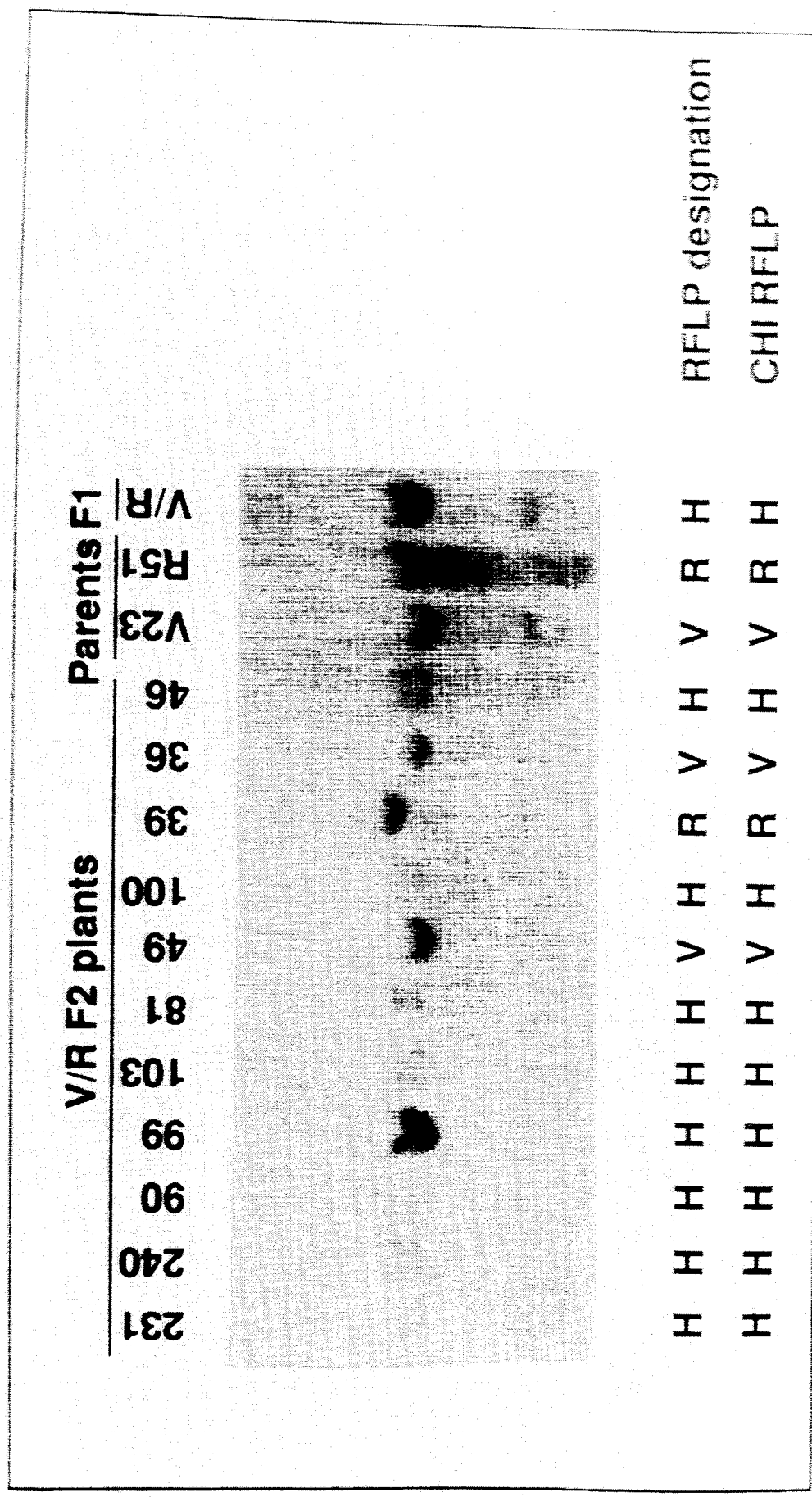

FIG. 7(B) is a representative autoradiograph from the RFLP analysis of the V23xR51 (V/R) F2 plants. Xbal digested genomic DNA was probed with the 3'region of pCGP175. The RFLP designation obtained using the pCGP175 probe was identical to the po-designation assigned using the chi-A probe. V: V23like RFLP; R: R51-like RFLP; H: heterozygotic (VR) RFLP.

Figure 8:
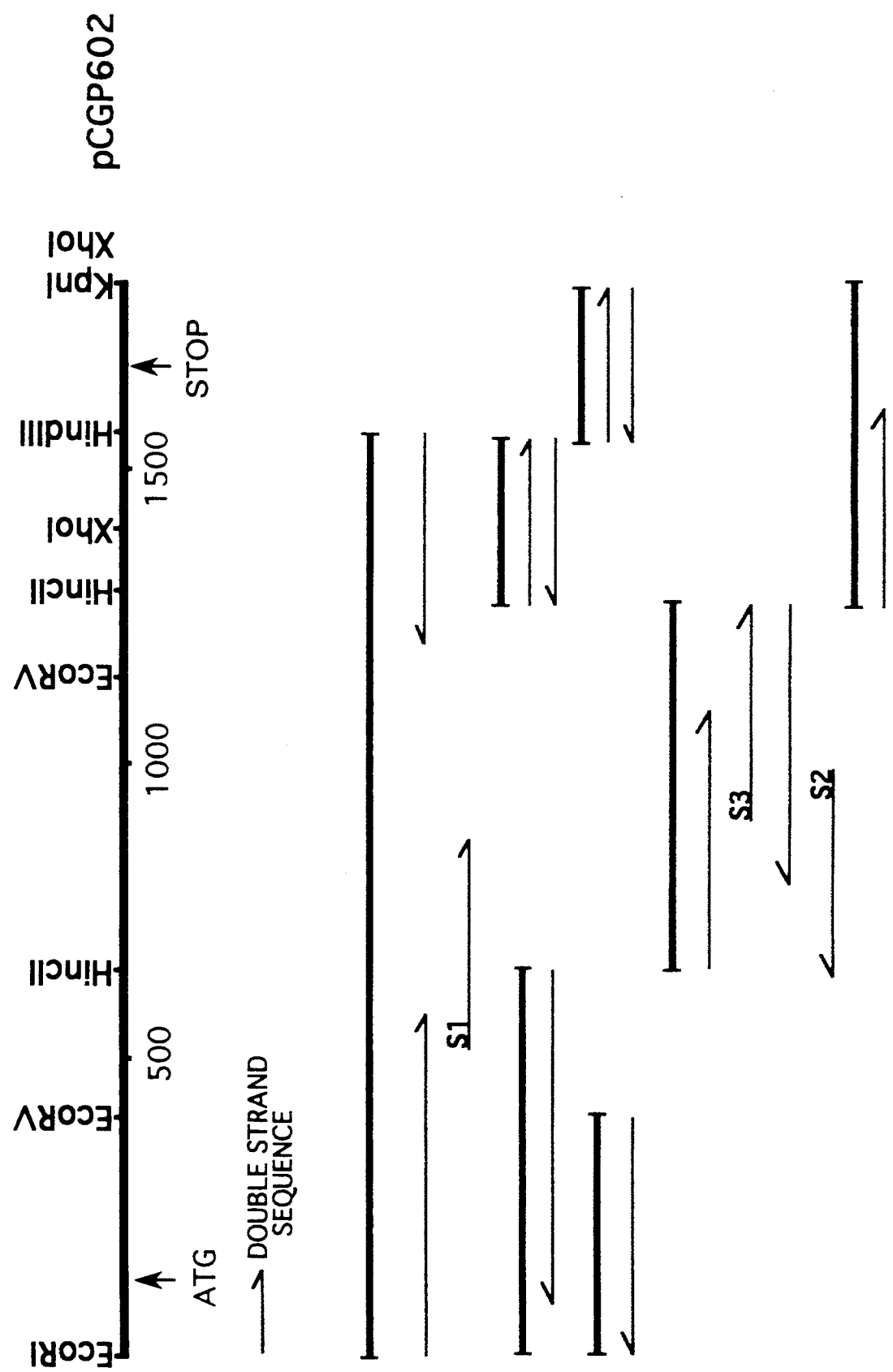

FIG. 8 shows a diagrammatic representation of a restriction enzyme map of pCGP602. Partial lengths of the eDNA insert are indicated by the bolder lines with solid ends (as opposed to arrows). These were subcloned into M13-rnp18 and mp19 and sequenced using oligonucleotide primer sequences, as indicated, to obtain overlapping sequence information. The extent and direction of sequence information obtained from each subcloned piece is shown by lines with half arrowheads. S1=primer sequence 1;S2=primer sequence 2; $3 =primer sequence 3; ATG indicates the methionine initiation codon and the total length of the clone in base pairs is also indicated.

FIGS. 9(A) to (D) are the nucleotide sequences and predicted amino acid sequences for the eDNA inserts from pCGP176 and pCGP602. The insert from pCGP602 includes the entire sequence shown. The 5'-end of the pCGP176 insert is indicated with an arrowhead.

FIGS. 10(A) to (C) represent the nucleotide sequence and predicted amino acid sequence for the eDNA insert from pCGP175.

Figure 11:
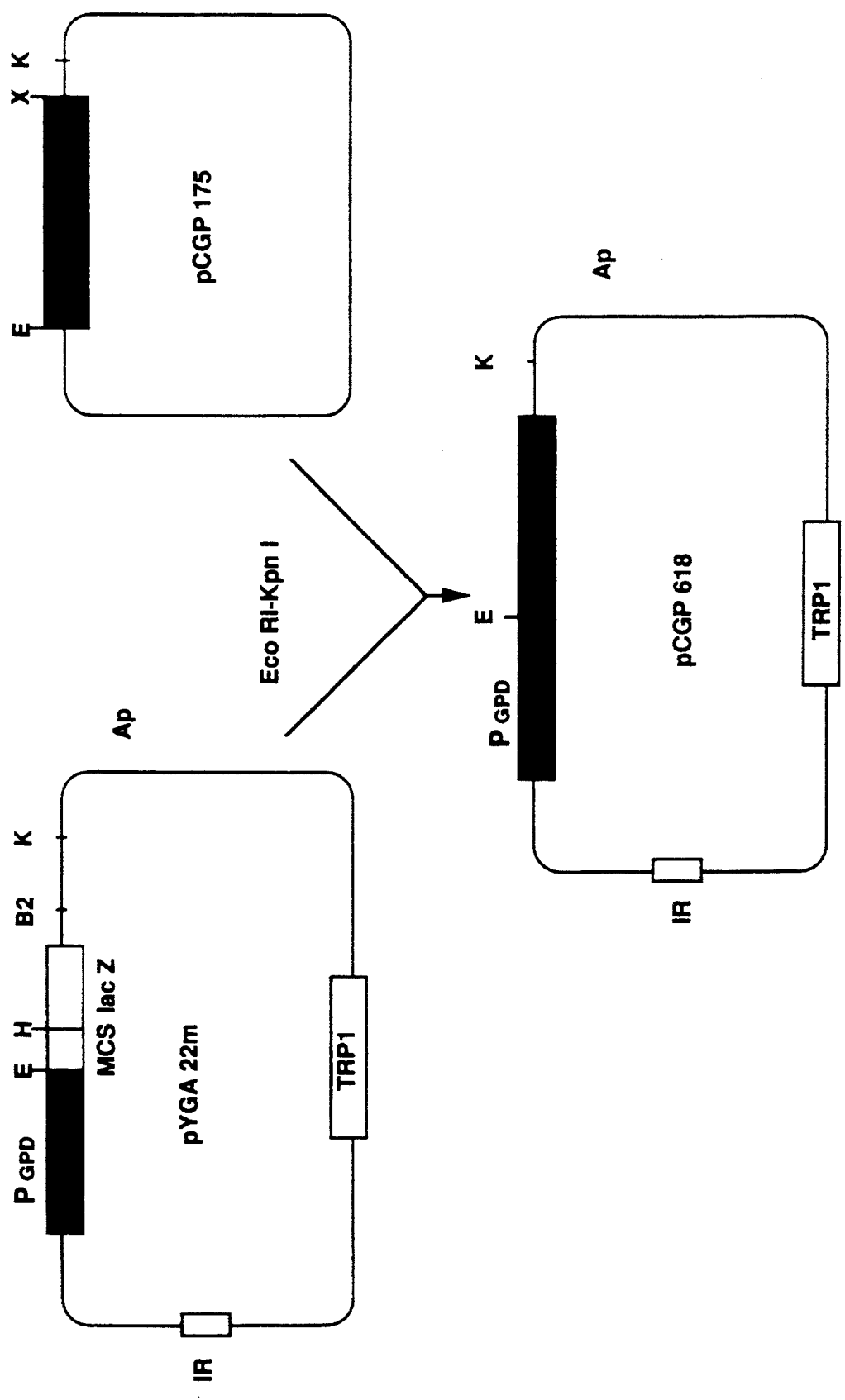

FIG. 11 is a diagrammatic representation of the construction of pCGP618. pCGP618 was constructed by cloning the pCGP175 eDNA insert in a sense orientation behind the yeast glyceraldehyde-3-phosphate dehydrogenase promoter (PGPD) in the expression vector pYGA22m. The eDNA insert from pCGP175 was ligated as an EcoRI-KpnI fragment with the large fragment that resulted from an EcoRI/KpnI digest of pYGA22m. E=EcoRI, H=HindIII, K=KpnI,X=XhoI,IR=Inverted repeat of 2 μm plasmid, Trpl=Trpl gene, Ap=Ampicillin resistance marker.

FIG. 12(A) shows a 3',5'-hydroxylase assay of yeast extracts using $^3$H-naringenin as substrate. The autoradiographs show conversion of $^3$H-naringenin to the 3',5'-hydroxylated derivative pentahydroxyflavanone by extracts of yeast transformed with the plasmid pCGP618 (1 and 2). No 3',5'-hydroxylase activity was detected in untransformed yeast (C). Conversion of naringenin to pentahydroxyflavanone by OGB 3',5'-hydroxylase is also shown (OGB C).

Figure 12:
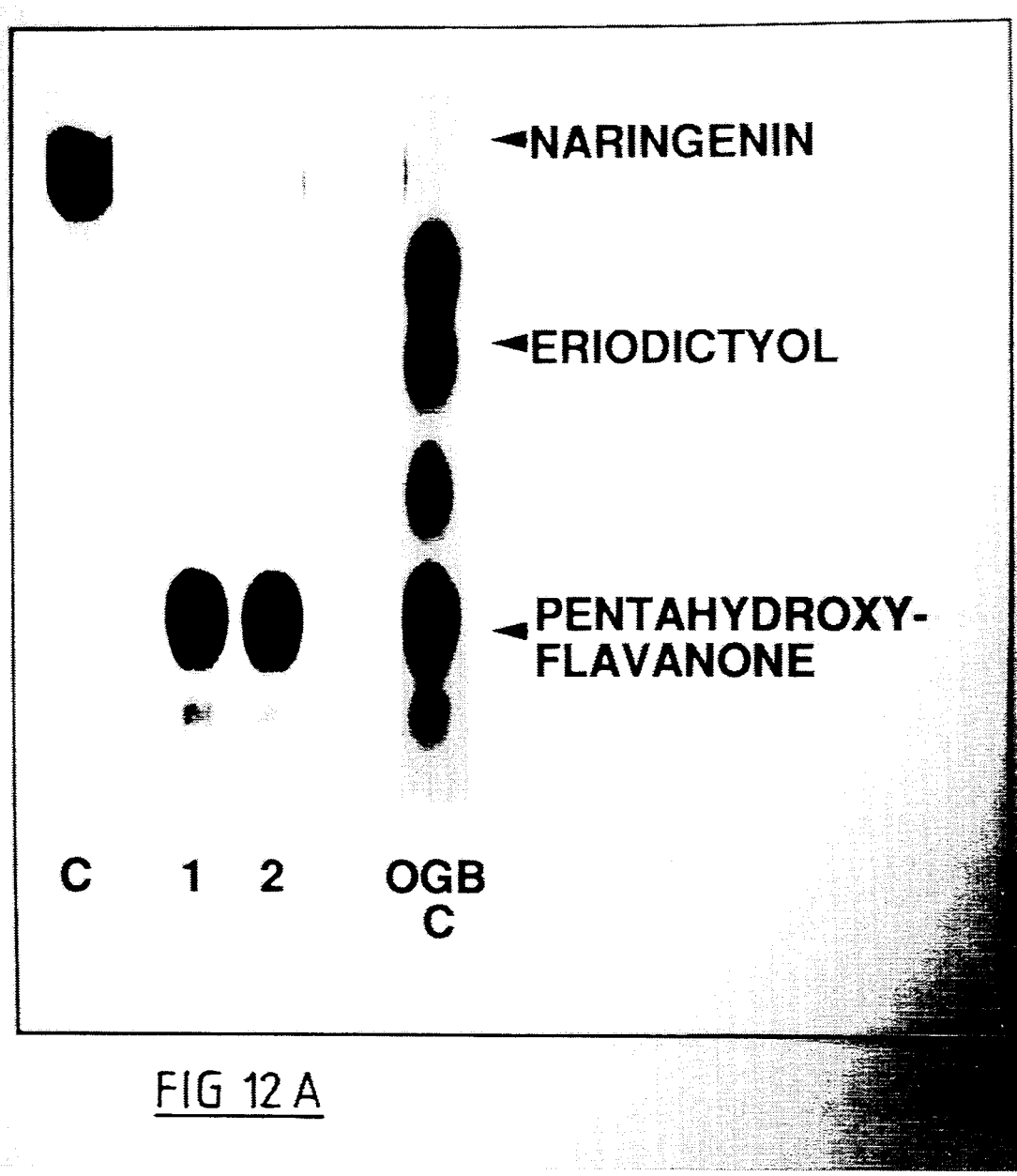
Figure 12B:
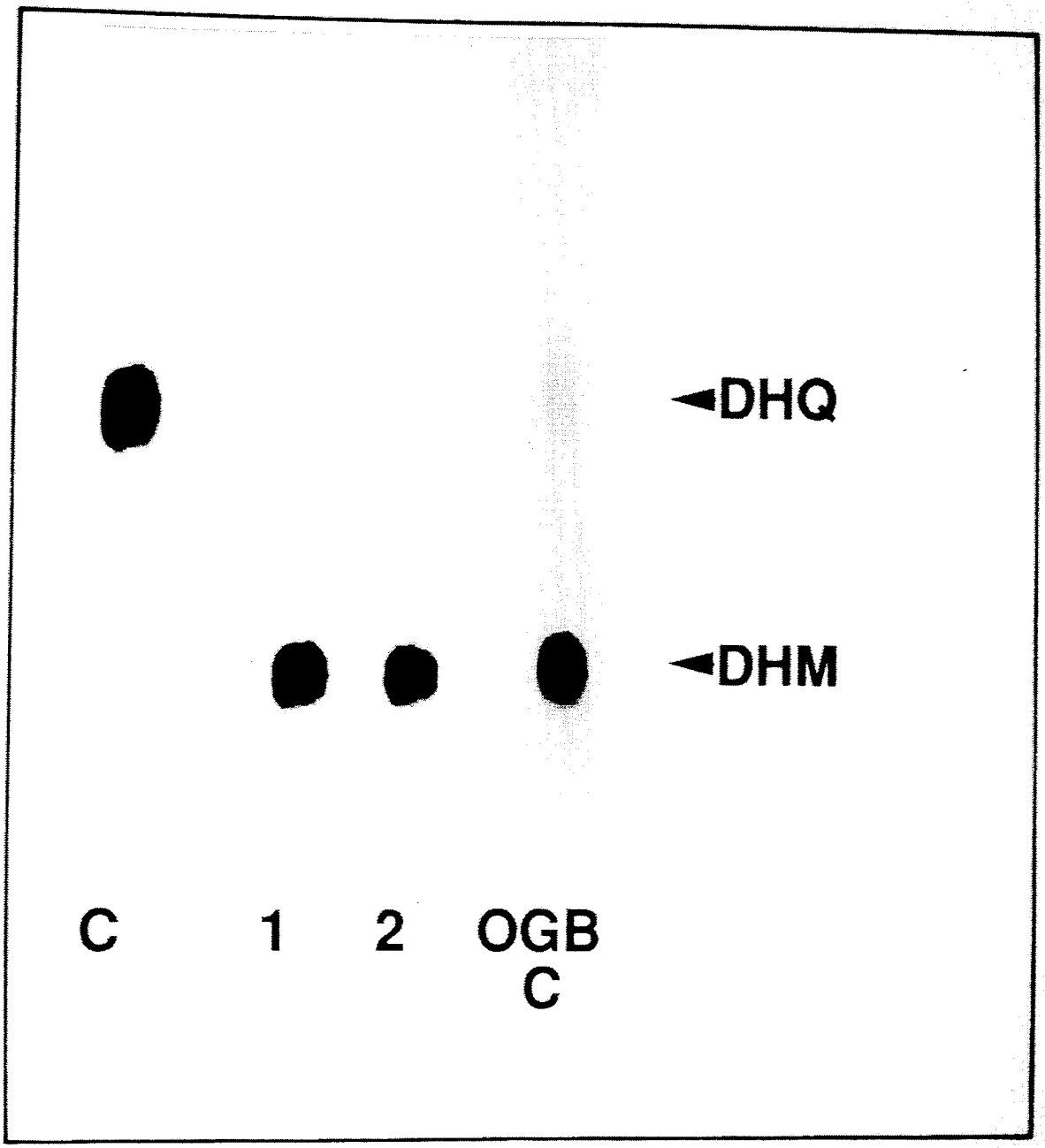

FIG. 12(B) shows a 3',5'-hyclroxylase assay of yeast extracts using 3H-dihydroquercetin as substrate. The autoradiographs show conversion of $^3$H-dihydroquercetin (DHQ) to $^3$H-dihydromyricetin (DHM) by extracts of yeast transformed with the plasmid pCGP618 (1 and 2). No 3,5'-hydroxylase activity was detected in untransformed yeast (C). Conversion of DHQ to DHM by OGB 3',5'-hydroxylase is also shown (OGB C).

Figure 13:
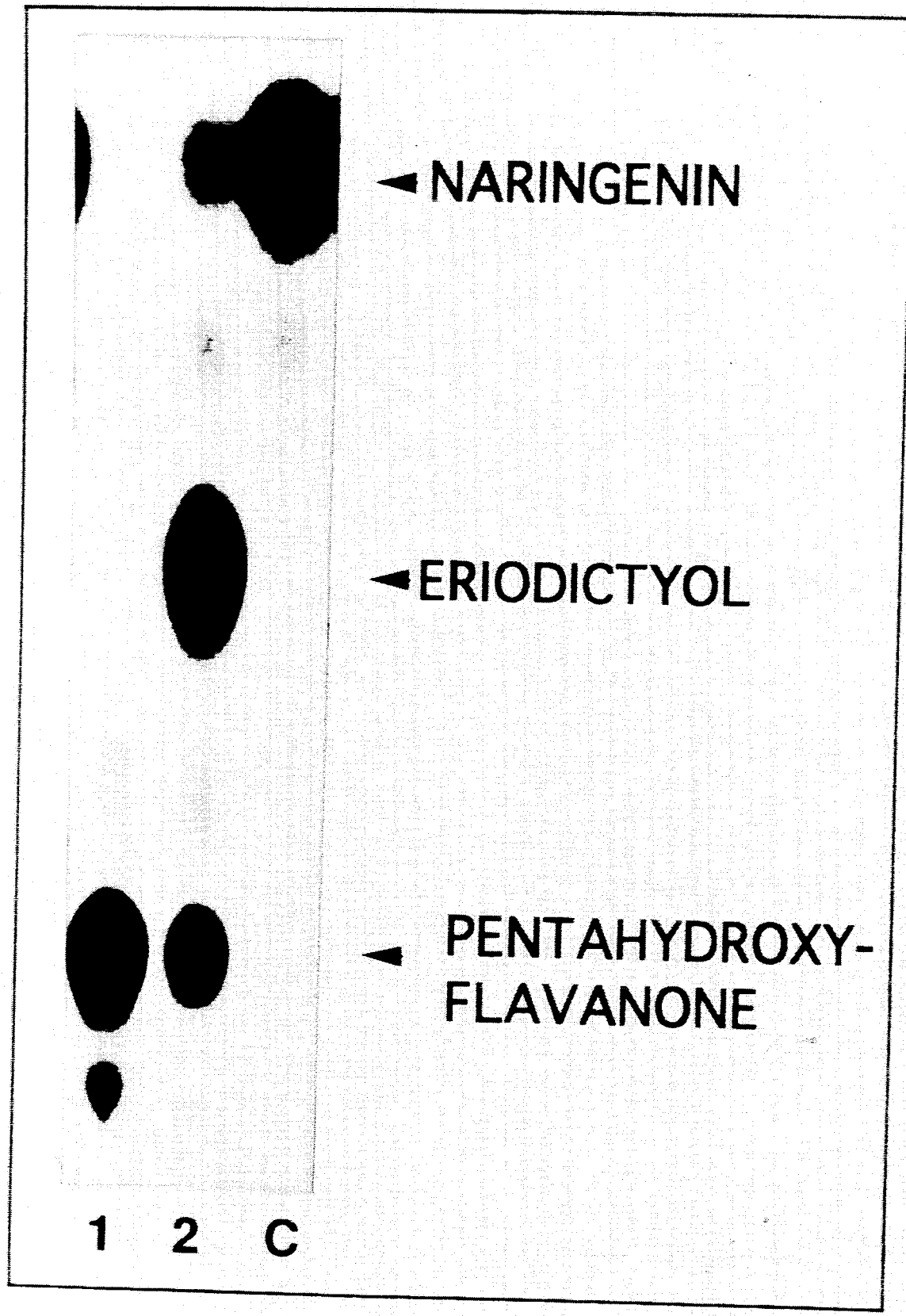

FIG. 13 shows a 3',5'-hydroxylase assay of yeast extracts using 3H-naringenin as substrate. The autoradiograph shows conversion of 3H-naringenin to the 3',5'-hydroxylareal derivative pentahydroxyflavanone by extracts of yeast transformed with plasmids pCGP618 and pCGP620 (1 and 2, respectively). The reaction products obtained from the pCGP620 extract also included the 3'-hydroxylareal eriodictyol as well as some of the original naringenin substrate indicating incomplete conversion to the 3',5'-hydroxylated end product. No 3',5'-hydroxylase activity was detected in untransformed yeast (C).

Figure 14:
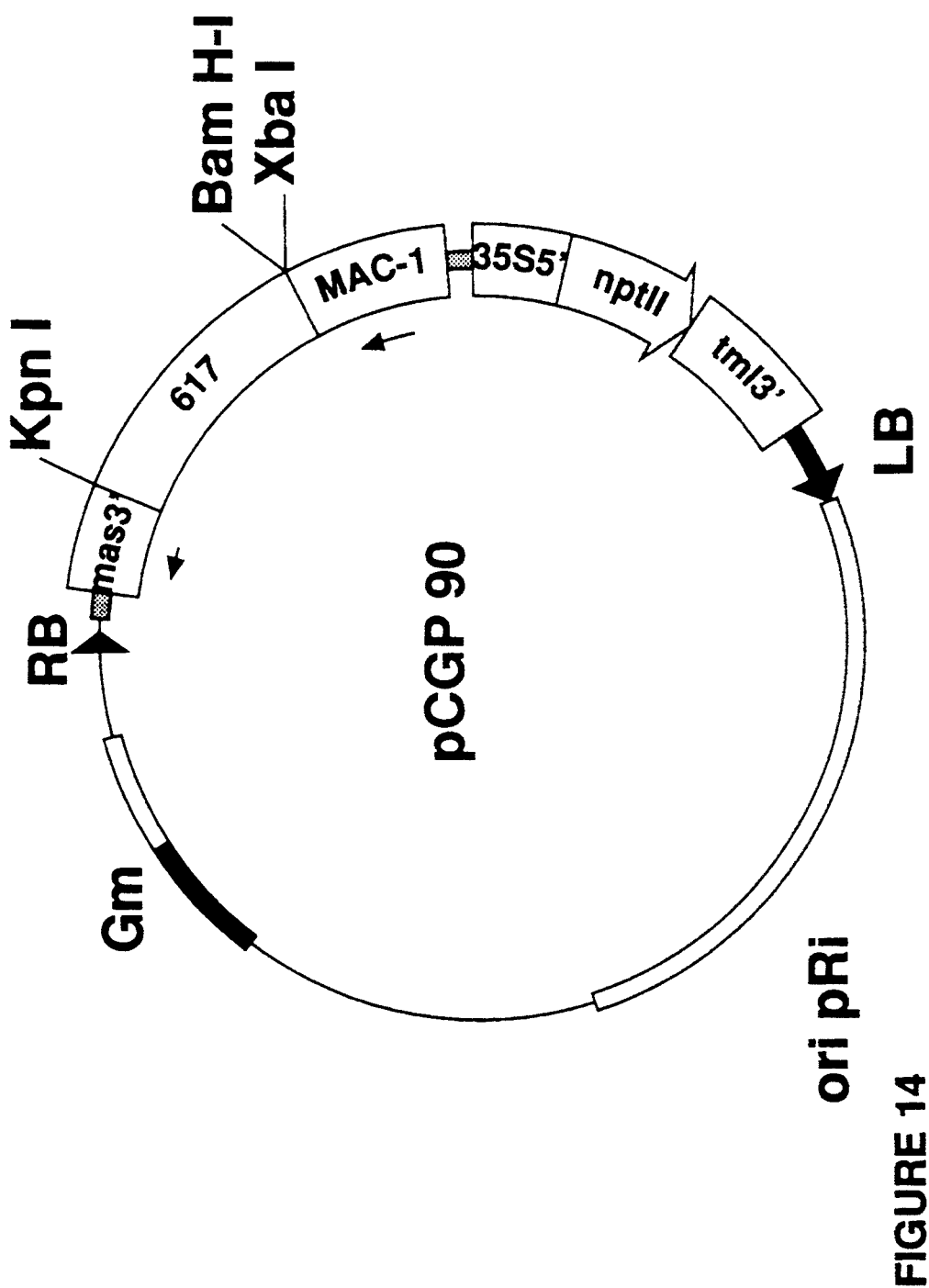

FIG. 14 is a diagrammatic representation of the plasmid pCGP90. The cDNA insert from pCGP602 was cloned in a sense orientation behind the Mac promoter of the expression vector pCGP293 as illustrated.

Figure 15:
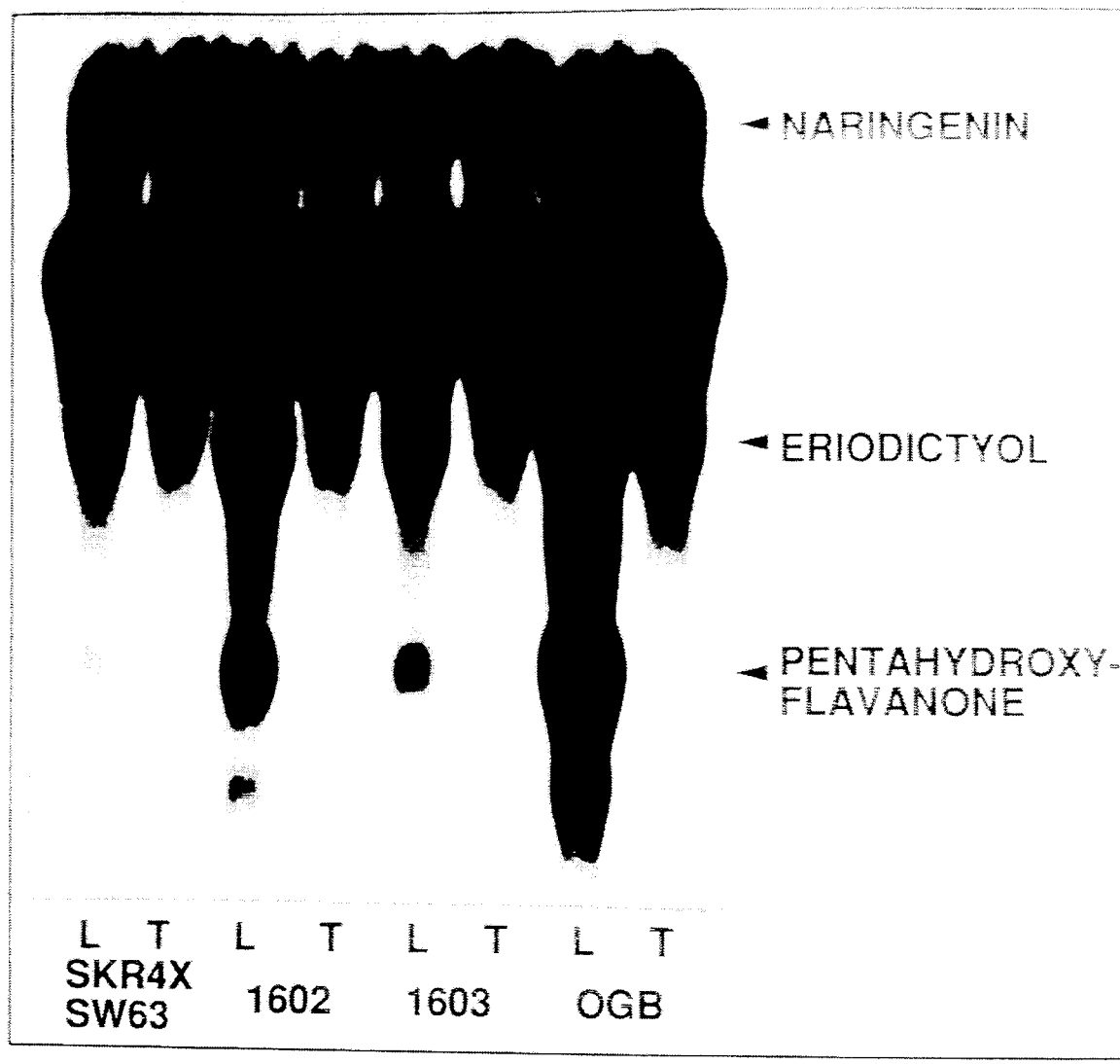

FIG. 15 shows a 3',5'-hydroxylase assay of petunia petal extracts. The autoradiograph shows the presence of low levels of 3',5'-hydroxylase activity (conversion of 3H-naringenin to 3H-pentahydroxyflavanone) in petal limb tissue (L) of Skr4×Sw63. Significantly higher levels of activity were detected in the limb tissue (L) of two Skr4×Sw63/pCGP90 transgenies (T/G 1602 and T/G 1603). No 3',5'-hydroxylase activity was detected in extracts of the petal tube (T) of either the non-transgenic Skr4×Sw63 hybrid or the two pCGP90 transgenics. Conversion of naringenin to pentahydroxyflavanone by extracts of limb (L) and tube (T) petal tissue of OGB is also shown.

Figures 16A, 16B, 16C:
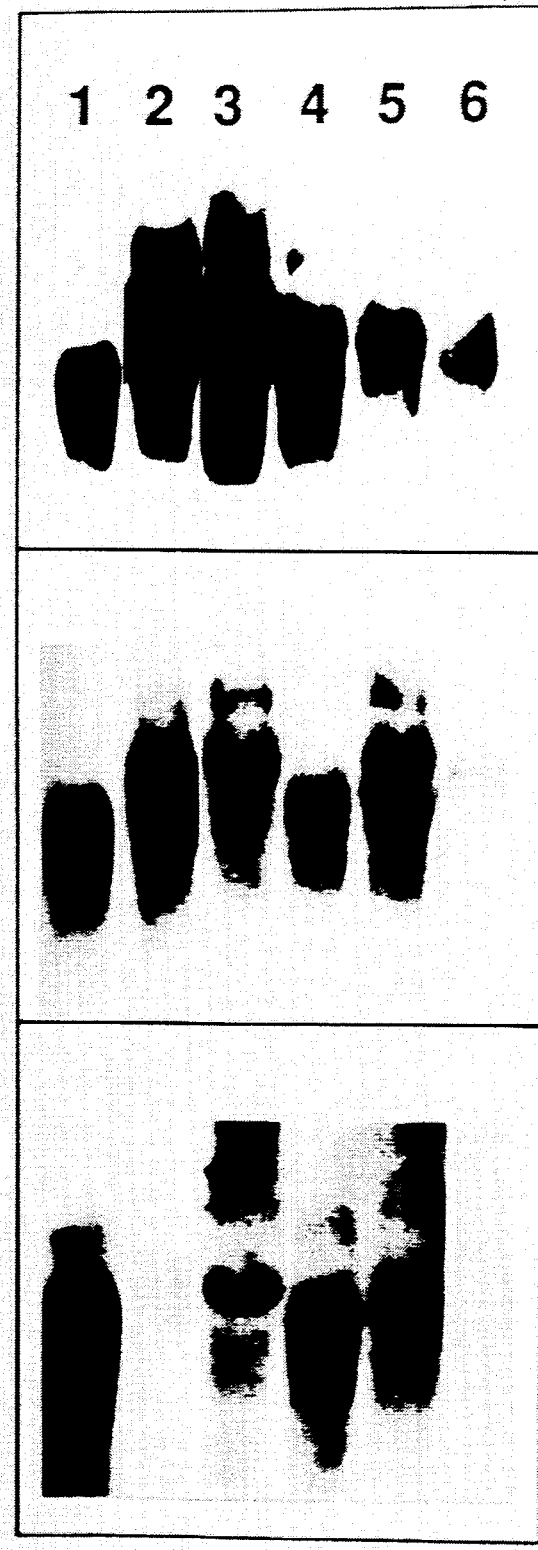

FIG. 16 is a photographic representation of an autoradiograph of an RNA blot probed with $^{32}$P-labelled Hfl cDNA. Each lane contained a 20µg sample of total RNA isolated from (1) P. hybrida cv. OGB petals; (2) pansy petals; (3) potato stems; (4) eggplant skins; (5) Nicotiana alata flowers; (6) Ageratum flowers. The probe used for A and B was derived from a 660 bO Ball DNA fragment; a 1.4 kb EcoRI/HindIII fragment was used for C. Washing conditions used were: (A) 6×SSC at 50° C.; (B) 2×SSC at 50° C.; (C) 0.2×SSC at 65° C.

Figures 17A, 17B:
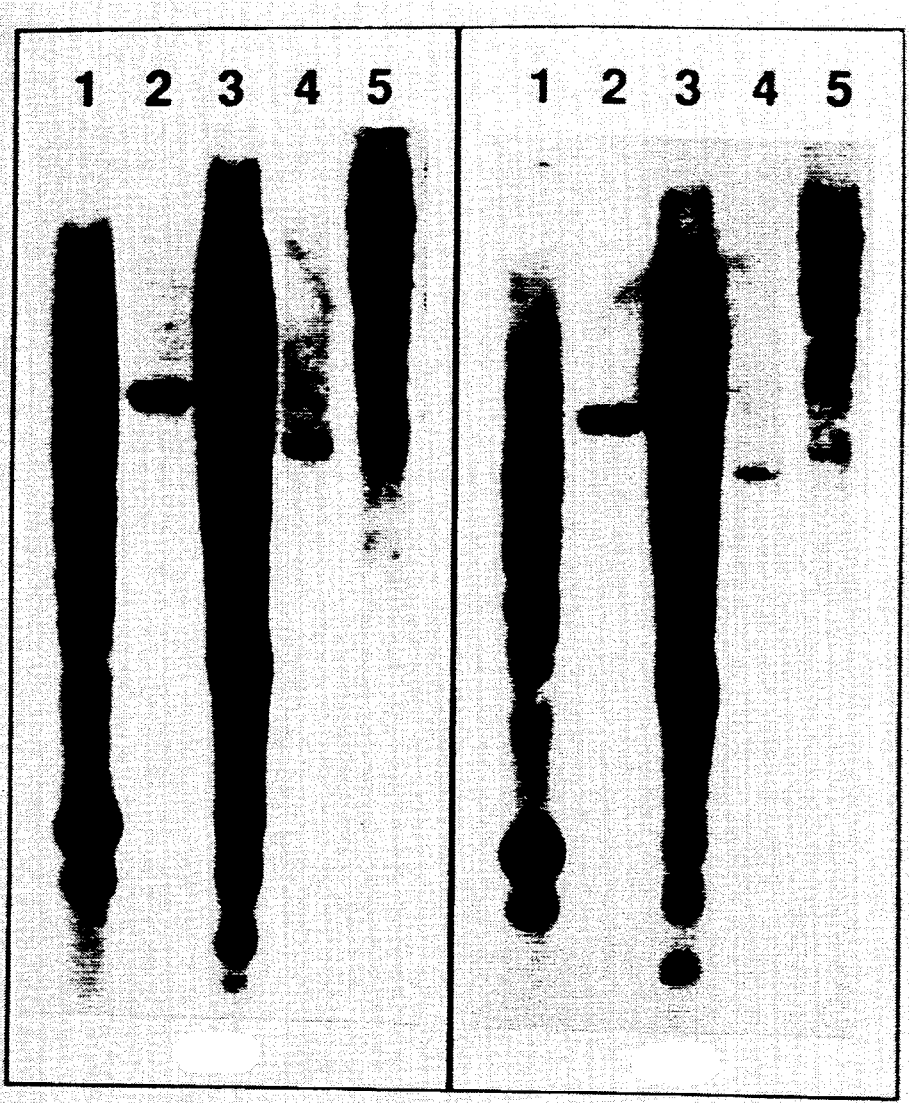

FIG. 17 is a photographic representation of autoradiographs of Southern blots probed with 32P-labelled Hfl eDNA. Each lane contained 10lag of DNA digested with EcooRI. The DNA samples were isolated from (1) eggplant, (2) dutch iris, (3) potato, (4) violets and (5) anemone. Washing conditions were: (A) 6×SSC at 50° C.; (B) 2×SSC at 65° C.

EXAMPLE

1. MATERIALS AND METHODS

Chemicals Enzymes and Radioisotopes

Eriodictyol and dihydroquercetin were obtained from Carl Roth KG and naringenin was obtained from Sigma. Dihydromyricetin was chemically synthesized from myricetin (Extra Synthese, France) by the method of Vercruysse et al. (1985). [$^3$H]-naringenin (5.7 Ci/mmole) and [$^3$H]-dihydroquercetin (12.4 Ci/mmole) were obtained from Amersham. All enzymes were obtained from commercial sources and used according to the manufacturer's recommendations.

Bacterial Strains

The Escherichia coli strains used were;
DH5αsupE44, A(lacZYA-ArggF)U169, λ80lacZΔM15, hsdR17 ($r_k^-$, $m_k^+$), recA1, endA1,-gyrA96, thi-1, relA1, deoR. (Hanahan, 1983 and BRL, 1986). p0 XL1-Blue supE44, hsdR17 ($r_k^-$, $m_k^+$), recA1, enctA1, gyrA96, thi-1, relA1, lac$^-$, [F'proAB, lacI$^q$, lacZΔM15, Tn10(tet$^r$)](Bullock et ad,1987).

PLK-F'recA, hsdR17($r_k^-$,$m_k^+$), mcrA', mcrB$^-$, lac$^-$, supE44, galK2, galT22, metBl, [F'proAB, lacI$^q$, lacZΔM15, Tn10(ter$^5$)](Stratagene).

The disarmed Agrobacterium tumefaciens strain AGL0 (Lazo et al, 1991) was obtained from R. Ludwig (Department of Biology, University of California, Santa Cruz).

The cloning vectors pBluescript and pBluescribe were obtained from Stratagene.

Transformation of E. coli and A. tumefaciens

Transformation of the E. coil strain DH5α cells was performed according to the method of Inoue et al. (1990).

The plasmid pCGP90 (FIG. 14) was introduced into the Agrobacterium tumefacierts strain AGL0 by adding 5lag of plasmid DNA to 100 µl of competent AGL0 cells prepared by inoculating a 50mL MG/L (Garfinkel and Nester, 1980) culture and growing for 16 hrs with shaking at 28° C. The cells were then pelleted and resuspended in 0.5 mL of 85% (v/v) 100 mM CACl$_2$/15% (v/v) glycerol. The DNA-Agrobacterium mixture was frozen by incubation in liquid N$_2$ for 2 minutes and then allowed to thaw by incubation at 37° C. for 5 minutes. The DNA/bacterial mix was then placed on ice for a further 10 minutes. The cells were then mixed with 1 mL of MG/L media and incubated with shaking for 16 hours at 28° C. Cells of A. turnefacienscarrying pCGP90 were selected on MG/L agar plates containing 100 µg/mL gentamycin. The presence of pCGP90 was confirmed by Southern analysis of DNA isolated from the gentamycin resistant transformants.

The Petunia hybrida varieties used are shown in Table 2.

TABLE 2

| Plant variety | Plant Material Properties | Source/Reference |
|---|---|---|
| Old Glory Blue (OGB) | F$_1$ Hybrid | Ball Seed, USA |
| V30 | An1, An2, An3, An4, An6, An8, An9, An10, An11, Ph1, Ph2, Ph3, Ph4, Ph5, Hfl1, Hf2, Ht1, Ht2, Rt, Mt1, Mt2, mfl, po, Gf | Koes et al. (1986) |
| V23 | An1, An2, An3, An4, An6, An8, An9, An10, ph1, Hfl, Hf2, ht1, Rt, Po, Bl, Fl | Wallroth et al. (1986) Doodeman et al. 1984 |
| R51 | An1, An2, An3, an4, An6, An8, An9, An10, An11, Ph1, hfl, hf2, Ht1, rt, po, bl, fl | Wallroth et al. (1986) van Tunen et al. (1990) Doodeman et al. (1984) |
| Sw63 | An1, An2, An3, an4, An6, An8, An9, An10, | I.N.R.A., Dijon, Cedex, France |

TABLE 2-continued

| Plant variety | Plant Material Properties | Source/Reference |
|---|---|---|
| | An11, Ph1, Ph2, Ph5, hf1, hf2, ht1, ht2, rt, po, mf1, fl, Gf | |
| Th7 | An1, An2, An3, An4, An6, An9, An10, An11, Hf1, Hf2, Ht1, Ht2, Ph1, Ph2, Ph5, Rt, po, mf1, mf2, Gf, fl | I.N.R.A., Dijon, Cedex, France |
| Skr4 | An1, An2, An3, An4, An6, An11, hf1, hf2, ht1, Ph1, Ph2, Ph5, rt, Po, Mf1, Mf2, fl | I.N.R.A., Dijon, Cedex, France |
| Sk4 × Sw63 | Skr4 × Sw63 F₁ Hybrid | |
| Rwl4 | An1, An2, An4, Ph1, ph2, Ph5, hf1, hf2, Ht1, Rt, Po, Bl, Lg1, Lu1, Vs1, Vs3, Vs5, la, Yg1, ws, Gf, Mt1, Mf2, fl | I.N.R.A., Dijon, Cedex, France |
| Rp57 | An1, An2, An4, Ph1, ph2, Ph5, hf1, hf2, Ht1, Rt, Po, Mt, Mf, fl, Gf, Bl, Lg1, Lu1, Vs1, Vs3, Vs5, Yg1, Ws. | I.N.R.A., Dijon, Cedex, France |
| Rp57 × Rwl4 | Rp57 × Rwl4 F₁ Hybrid | |

Plants were grown in specialised growth rooms with a 14 hr day length at a light intensity of 10,000 lux and a temperature of 22 to 26° C. OGB flowers were harvested at developmental stages defined as follows:

Stage 1: Unpigmented, closed bud (<25 mm in length)
Stage 2: Pigmented, closed bud (25-35 mm in length).
Stage 3: Dark purple bud with emerging corolla (>35 mm in length).
Stage 4: Dark purple opened flower pre-anther dehiscence (>50 mm in length).
Stage 5: Fully opened flower with all anthers dehisced.

Flowers of the other varieties, as described in Table 2, were harvested prior to anther dehiscence at the stage of maximum pigment accumulation.

Preparation of Plant Extracts for assay of 3',5'-Hydroxylase Activity Plant tissue was homogenised in a 2 to 5 times volume of ice-cold extraction buffer (100 mM potassium phosphate (pH 7.5), 1 mM EDTA, 0.25M sucrose. 0.25M mannitol, 0.1% (w/v) BSA, 100 nM Pepstalin, 100 nM Leupeptim 0.1 mg/mL PMSF, 20 mM 2-mercaptoethanol and 10 mg/mL polyclar AT). The homogenate was centrifuged at 10,000 rpm in a JA20 rotor (Beckman) for 10 rain at 4° C. and an aliquot of the supernatant was assayed for 3',5'hydroxylase activity.

3',5'-Hydroxylase Assay

3',5'-Hydroxylase enzyme activity was measured using a modified version of the method described by Storz and Forkmann (1982). The assay reaction mixture typically contained 100 μL of plant extract, 51L of 50 mM NADPH in assay buffer (100 mM potassium phosphate (pH8.0), 1 mM EDTA and 20 mM 2-mercaptoethanol), 10 μCi of [$^3$H] naringenin or 5 μCi of [$^3$H]-dihydroquercetin and was made up to a final volume of 210 μL with the assay buffer. Following incubation at 23° C. for 2-16 hours, the reaction mixture was extracted with 0.5 mL of ethylacetate. The ethyl acetate phase was dried under vacuum and then resuspended in 10 btL of ethyl acetate. The tritiatect flavonoid molecules were separated on cellulose thin layer plates (Merck 5577, Germany) using a chloroform: acetic acid: water (10:9:1, v/v) solvent system. At the completion of the chromatography, the TLC plates were sprayed with 7% (v/v) 2,5-diphenyloxazol in diethyl ether. The reaction products were localised by autoradiography and identified by comparison to non-radioactive naringenin, eriodictyol, dihydroquercetin and dihydromyricetin standards which were run alongside the reaction products and visualized under UV light.

Glucose/High Light Induction of Delphinidin Synthesis in Leaves Leaves were harvested from P. hybrida cv. OGB and cut into 1cm$^2$ sections in sterile water. The leaf sections were then floated on a 2% (w/v) glucose solution and exposed to a light intensity of 24,000 lux for 96 hours.

Construction of cDNA Library #1

Twenty grams of stage 3 to 40GB flower limbs were homogenised in 100 mL of PEB (200 mM Tris-HC1 (pH 8.6), 60 mM KC1, 30 mM MgCl$_2$, 25 mM EGTA) containing 10 mM vanadyl ribonucleoside complex. Cell debris was removed by filtering the homogenate through sterile Miracloth (Calbiochem). The flitrate was layered on top of a step gradient of 6 mL of PEB containing 25% (w/v) sucrose, 250 units InhibitAce (5-Prime 3-Prime), and 6 mL of PEB containing 50% (w/v) sucrose and 250 units InhibitAce in Ultra-Clear$^{TM}$ Quick-Seal$^{TM}$ (Beckman) centrifuge tubes. The tubes were centrifuged for hours at 26,000 rpm in a 70Ti rotor. Membrane-bound polysomes were collected from the 25% (w/v) sucrose/50% (w/v) sucrose interface and added to a 4M guanidium isothiocyanate solution. RNA was isolated from the denatured polysomes by pelleting through a 5.7M CsCl cushion, as described by Turpen and Griffith (1986).

A Uni-ZAP$^{TM}$ XR vector kit (Stratagene) was used to construct a directional cDNA library in ΔZAP using 25 lag of the polysomal RNA as template. The primary library, which contained 250,000 plaque forming units (pfu), was amplified by overnight growth on NZY plates (Sambrook et ad, 1989) and the amplified phage stock was eluted in PSB (10.0 mM NaCl, 8 mM MgSO$_4$,50 mM Tris-HC1 (pH 7.5), 0.01% (w/v) gelatin) as described by Sambrook et al, (1989).

Construction of cDNA Library #2

Total RNA was isolated from the petal tissue of P. hybrida cv. OGB stage 3 to 4 flowers using the method of Turpen and Griffith (1986). poly(A)+RNA was selected from the total RNA by three cycles of oligoodT cellulose chromatography (Aviv and Leder, 1972).

Two micrograms of poly(A)$^{30}$ RNA were reverse transcribed in a 20 laL volume containing 1×Superscript$^{TM}$ reaction buffer, 10 mM dithiothreitol, 500 μM dATP, 500 μM dGTP, 500 μM dTTP, 500 μM 5-methyl-dCTP, 0.75 lag oligonucleotide #8 and 2 μL Superscript$^{TM}$ reverse transcriptase (BRL). The reaction mix was incubated at 37° C. for 50 minutes, 44° C for 10 minutes, then placed on ice.

Second strand reaction mix (140 laL) was added to the first strand reaction. The second strand reaction mix consisted of 21 mM Tris-HC1, 104 mM KCl, 5.3 mM MgCl2, 171 μM β-NAD, 11.4 mM (NH$_4$)$_2$SO$_4$, 214 μM dATP, 642 μM dCTP, 214 μM dGTP, 214 μM dTTP, 4 mM DTT, 10 μCi $^{32}$P-dCTP (3000 Ci/mMole), 15 units E. coli DNA ligase, 40 units DNA polymerase (Boehringer) and 0.8 units RNAse H. The final mixture was incubated for 150 minutes at 16° C. To make the double-stranded eDNA blunt-ended, 10 units T4 DNA polymerase was added, and the reaction continued for a further 15 minutes at 16° C. The reaction was stopped and the eDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 minutes) and the DNA was purified by phenol/chloroform extraction and ethanol precipitation. The eDNA was digested with 50 units XhoI (Boehringer) in a reaction volume of 100 gL, using conditions recommended by the manufacturer. The enzyme was heat killed (70° C., 20 minutes) and the mixture passed through an S400 spun column (Pharmacia) which had been equilibrated in STE buffer (Sambrook et al, 1989). The eluate was phenol/chloroform extracted and ethanol precipitated. After microcentrifugation at 4° C. for 30 minutes the cDNA pellet was rinsed with 70% (v/v) ethanol, air dried and resuspended in 10 μL, of TIE buffer (10 mM Tris-HCI (pH7.5), 1 mM EDTA).

NA-45 membrane (Schleicher and Schuell) was used to isolate cDNA in the size range of 1.3 to 2.5kb from a 7.5 aL sample that had been electrophoresed through a 1% (w/v) agarose gel.

The size fractionated cDNA was ligated with 1 μg ΔZAPII EcoRI/XhoI/CIAP treated vector (Stratagene) in 5 μL reaction buffer consisting of 50 mM Tris-HCl (pH 7.0), 10 mM MgCl$_2$, 10 mM dithiothreitol, 1 mM ATP and 2 units T4 DNA ligase. The reaction was performed at 4° C. for 2 days.

After leaving at room temperature for two hours, the ligation reaction mixture was packaged using the Packagene system (Promega). The total number of recombinants was 270,000 pfu.

An amount of 150,000 pfu of the packaged cDNA was plated at 10,000 pfu per 15 cm diameter plate after transfeeling PLK-F' cells. The plates were incubated at 37° C. for eight hours, then stored overnight at 4° C. Duplicate lifts were taken onto Colony/Plaque Screen$^{TM}$ filters (Dupont) and treated as recommended by the manufacturer.

Synthesis of Oligonucleotides

Oligonucleotides were synthesized on an Applied Biosystems PCR-Mate DNA synthesizer using methods recommended by the manufacturer. The oligonucleotides synthesized were, 5'-3':

Oligo 1: (SEQ. ID. NO: 3) GGAAGCTTATIC-CITT(T/C)GGIGCIGG

Oligo 2: (SEQ. ID. NO: 4) GGATGACTCAG-TAAAACGACGGCCAGT

Oligo 3 (SEQ. ID. NO. 5) CCIGG(A/G)CAIATIC(G/T)(C/T)(C/T)TICCIG-CICC(A/G)AAIGG

Oligo 4:(SEQ. ID. NO. 6) GGATGACT-CAAACAGCTATGACCATG

Oligo 5:(SEQ. ID. NO. 7) GTTCAATTCGGAAT-GATG

Oligo 6:(SEQ. ID. NO. 8) GCTGCACTTAATC-CATAT

Oligo 7:(SEQ. ID. NO. 9) TGCATAGCTTTTGGG

Oligo 8:(SEQ. ID. NO. 10) GAGAGAGAGAGAGAGAGAGATCT-CGAGTTTTTTTTTTTTTT

Oligo 9:(SEQ. ID. NO. 11) ATGTCTCCTCCAGTG

Oligo 10:(SEQ. ID. NO. 12) CTAGACTCCAATCAC

Oligos 2 and 4 included a GCN4 binding site (indicated by underlining) which has been shown to facilitate the enrichment of double stranded PCR products (Lew and Kemp, 1989).

The basis for the design of oligo 3 was as follows: Amino acid sequences from the putative haem-binding domain of an avocado cytochrome P450 (Bozak et al. 1990) and the corresponding sequences encoded by the two petunia cytochrome P450 homologues pCGP142 and pCGP147 were aligned:

| | | | | | | | | | |
|---|---|---|---|---|---|---|---|---|---|
| avocado (SEQ ID NO:13) | P | F | G | A | G | R | R | G | C | P | G |
| pCGP142 (SEQ ID NO:14) | P | F | G | A | G | K | R | I | C | P | G |
| pCGP147 (SEQ ID NO:15) | P | F | G | S | G | R | R | I | C | P | G |

The consensus amino acid sequence of the haem-binding region for the three plant cytochromes P450 could thereby be seen to be: P F G A(S) G R(K) St t(G) C P G Possible permutations of nucleotide sequence that could encode the arnino acids found in the haem-binding domain of the three cytochrome P450 molecules could then be deduced:

```
5'- CCX TTT GGX GCX GGX AGX CGX ATX TGT CCX GGX -3'
        C       AG      CA   A   GG      C
                T
```

X indicates nucleotide positions where all four nucleotides (A,C,G and T) can be used. Oligo 3 was designed to complement a subset of the consensus sequence derived from the three plant cytochromes P450. Deoxyinosine (I) was used predominantly when base degeneracy was greater than three. The resulting oligonucleotide sequence was as shown above.

PCR Reactions

Helper phage R408 (Stratagene) was used to excise pBluescript phagemids containing petunia eDNA inserts from 200,000 pfu of the amplified A. ZAP cDNA library #1 using methods described by the manufacturer. *Escherichia coli* XL1- Blue were transferred with the phagemid mixture and 250,000 colonies were plated out on ampicillin-containing media. Cells were resuspended in LB (Sambrook et al, 1989) and plasmid DNA was isolated using an alkaline lysis procedure (Sambrook eta/, 1989). Plasmid DNA was further purified by banding on a CsCl gradient. This DNA was used as the template for PCR.

PCR reactions for amplification of petal cytochrome P450 homologues contained 5 to 100ng of excised DNA, 10 mM Tris-HCl (pH 8.3), 50 mM KCl, 1.5 mM MgCl$_2$, 0.01% (w/v) gelatin, 0.2 mM each dNTP, 0.4 μM each primer and 1.25 units Taq. polymerase (Cetus). Reaction mixes (50b×L) were cycled 30 times between 94° C., 48° C. and 72° C. for 1 minute at each temperature. The amplified products were gel-purified using Genec bean (Bio 101 Inc.), reamplified to obtain sufficient material for cloning and then end-repaired using T4 DNA polymerase. DNA amplified using oligos 1 and 2 was digested with HindIII and XhoI prior to cloning into pBluescript. The PCR product generated by amplification between oligos 3 and 4 was cloned directly into the ddT-tailed pBluescript vector described by Holton and Graham (1991).

Screening of cDNA Libraries

Duplicate plaque lifts were hybridised and washed as follows: High stringency conditions (hybridization: 50% (v/v) formamide, 6 x SSC, 1% (w/v) SDS at 42°

C. for 16 hrs and washing: 2 × SSC, 1% (w/v) SDS at 65° C. for 2×15 minutes followed by 0.2×SSC, 1% (w/v) SDS at 65° C. for 2×15 minutes) were used to detect sibling clones and low stringency conditions (hybridisation: 20% (v/v) formamide, 6×SSC, 1% (w/v) SDS at 42° C. for 16 hrs and washing: 6×SSC, 1% (w/v) SDS at 65° C. for 1 hour) were used to detect related sequences.

Northern Analysis

Total RNA was isolated from tissue that had been frozen in liquid $N_2$ and ground to a fine powder using a mortar and pestle. An extraction buffer of 4M guanidium isothiocyanate, 50 mM Tris-HCl (pH 8.0), 20 mM EDTA, 0.1% (v/v) Sarkosyl, was added to the tissue and the mixture was homogenized for 1 minute using a polytron at maximum speed. The suspension was filtered through Miracloth (Calbiochem) and centrifuged in a JA20 rotor for 10 minutes at 10,000 rpm. The supernatant was collected and made to 0.2 g/mL CsCl (w/v). Samples were then layered over a 10 mL cushion of 5.7 M CsCl, 50 mM EDTA (pH 7.0) in 38.5 mL Quick-seal centrifuge tubes (Beckman) and centrifuged at 42,000 rpm for 12–16 hours at 23° C. in a Ti-70 rotor. Pellets were resuspended in TE/SDS (10 mM Tris-HCl (pH 7.5), 1 mM EDTA, 0.1% (w/v) SDS) and extracted with phenol:chloroform:isoamyl alcohol (25:24:1) saturated in 10 mM EDTA (pH 7.5). Following ethanol precipitation the RNA pellets were resuspended in TE/SDS.

RNA samples were electrophoresed through 2.2M formaldehyde/1.2% (w/v) agarose gels using running buffer containing 40 mM morpholinopropanesulphonic acid (pH 7.0), 5 mM sodium acetate. 0.1 mM EDTA (pH 8.0). The RNA was transferred to Hybond-N filters (Amersham) as described by the manufacturer and probed with 32P-labelled cDNA fragment ($10^8$ cpm/µg, $2×10^6$ cpm/mL). Prehybridization (1 hr at 42° C.) and hybridization (16 hr at 42° C) was carried out in 50% (v/v) formamide, 1M NAGl, 1% (w/v) SDS, 10% (w/v) dextran sulphate. Degraded salmon sperm DNA (100 µg/mL) was added with the 32P-labelled probe for the hybridization step.

Filters were washed in 2×SSC/1% (w/v) SDS at 65° C. for 1 to 2 hours and then 0.2×SSC/1% (w/v) SDS at 65° C. for 0.5 to 1 hour. Filters were exposed to Kodak XAR film with an intensifying screen at −70° C. for 48 hours.

RFLP Analysis a. Isolation of Genomic DNA

DNA was isolated from leaf tissue essentially as described by Dellaporta et al, (1983). The DNA preparations were further purified by CsCl buoyant density centrifugation (Sambrook et al, 1989).

b. Southern blots

The genomic DNA (10 µg) was digested for 16 hours with 60 units of XbaI and electrophoresed through a 0.7% (w/v) agarose gel in a running buffer of TAlE (40 mM Tris-acetate, 50 mM EDTA). The DNA was then denatured in denaturing solution (1.5M NaCl/0.5 M NaOH) for 1 to 1.5 hours, neutralized in 0.5 M Tris-HCl (pH 7.5)/1.5 M NaCl for 2 to 3 hours and the DNA was then transferred to a Hybond N (Amersham) filter in 20×SSC.

c. Isolation of chi-A probe

A cDNA clone of chi-A (van Tunen et al., 1988) was synthesized by PCR using cDNA template made from OGB stage 3 petal RNA and two oligonucleotide primers: #9, which covered nucleotides 6–20 and #10, which was complementary to nucleotides 711–725 of the published chi-A cDNA sequence (van Tunen et al, 1988). The resulting PCR product was ligated into the Sinai site of pBluescribe M13'(Stratagene) and sequenced to confirm that the cloned fragment corresponded to the published sequence.

$^{31}$P-Labelling of DNA Probes

DNA fragments (50 to 100 ng) were radioactively labelled with 50 laCi of [$\alpha$-$^{32}$P]-dCTP using an oligolabellin kit (Bresatec). Unincorporated ($\alpha$-$^{32}$P]-dCTP was removed by chromatography on a Sephadex G-50 (Fine) column.

DNA Sequence Analysis

DNA sequencing was performed essentially by the method of Sanger et al. (1977) using the Sequenase enzyme (USB, version 2.1). The complete sequence of clones pCGP602, pCGP176 and pCGP175 was determined by compilation of sequence from different M13 -mp18 and -mp19 (Norrander et al, 1983; Yanisch-Perron, 1985) subclones obtained using standard cloning procedures (Sambrook et al, 1989). For some regions it was necessary to synthesize specific oligonucleotide primers to obtain overlapping sequence data. The following six primers were synthesized for that purpose:

5'CGTGCCAATGAGCTAGG 3'primer sequence 1 (SEQ. ID. NO. 17)

5'GATGTTGGTTGTACTGAG 3'primer sequence 2 (SEQ. ID. NO. 18)

5'GGAAACCAGATTTTCTTG 3'primer sequence 3 (SEQ. ID. NO. 19)

5'TTTTTTTTTTTTTTTTTT(AGC) 3'primer sequence 4 (SEQ. ID. NO. 20)

5'GTTTTCCCAGTCACGAC 3 'primer −40 (SEQ. ID. NO. 21)

5. AACAGCTATGACCATG 3'reverse primer (SEQ. ID. NO. 22)

A restriction map of pCGP602 showing the position of several of these sequences may be seen in FIG. 8.

Homology searches against Genbank, SWISS-PROT and EMBL databases were performed using the FASTA and TFASTA programs (Pearson and Lipman, 1988).

Construction of pCGP293

The expression binary vector pCGP293 was derived from the Ti binary vector pCGN1559 (McBride and Summerfelt, 1990). Plasmid pCGN1559 was digested with KpnI and the overhanging 3' ends were removed with T4 DNA polymerase according to standard protocols (Sambrook et a/,1989). The vector was then further digested with XbaI and the resulting 5' overhang was repaired using the Klenow fragment of DNA polymerase I. The vector was then re-ligated to give pCGP67. A 1.97 kb PstI fragment containing the Mac promoter, was terminator and various cloning sites (Comai et al, 1990) was isolated from pCGP40 and inserted into the PstI site of pCGP67 to give pCGP293.

Plasmid pCGP40 was constructed by removing the GUS gene (Jefferson et al, 1987) as a BamHI-SacI fragment from pCGN7334 and replacing it with the BamHI-SacI fragment from pBluescribe M13−that includes the multicloning site. Plasmid pCGN7334 (obtained from Calgene, Inc. CA, USA), was constructed by inserting the fragment containing the Mac-GUS-mas gene fusion into the XhoI site of pCGN7329 (Comai et al, 1990).

Construction of pCGP90

Plasmid pCGP90 was constructed by cloning the cDNA insert from pCGP602 in a sense orientation behind the Mac promoter (Comai et al, 1990) of pCGP293. The BamHI-KpnI fragment containing the cDNA insert was isolated from pCGP602 and ligated with a BamHI/KpnI digest of pCGP293.

Correct insertion of the insert in pCGP90 was established by restriction analysis of DNA isolated from gentamycin resistant transformants.

Construction of the Yeast Expression Vector pYGA22m

M13-mp18 was digested with EcoRI and BglII to produce a 700 bp fragment that contained a multicloning site. This fragment was ligated with the 9 kb EcoRI-BglII fragment from pYGA2269 (Ashikari et al, 1989). The resulting construct, designated pYGA22m, contained the multicloning site inserted downstream of the yeast glyceraldehyde-3-phosphate dehydrogenase promoter (FIG. 11).

Construction of pCGP618

A 1.8 kb EcoRI-KpnI fragment that included the entire cDNA insert from pCGP175 was ligated with the 9 kb EcoRI - KpnI fragment from pYGA22 m. The resulting plasmid, pCGP618, contained the pCGP175 eDNA fragment ligated in a sense orientation behind the glyceraldehyde-3-phosphate dehydrogenase promoter (FIG. 11).

Construction of pCGP620

A 1.8 kb EcoRI-KpnI fragment that included the entire eDNA insert from pCGP176 was ligated with the 9kb EcoRI-KpnI fragment from pYGA22 m (as described for the construction of pCGP618). The resulting plasmid, pCGP620, contained the pCGP176 cDNA fragment ligated in a sense orientation behind the yeast glyceraldehyde-3-phosphate dehydrogenase promoter.

Yeast Transformation

The yeast strain G-1315 (Mat α, trpl) (Ashikari et al, 1989) was transformed with pCGP618 and pCGP620 according to Ito et al, (1983). The transform ants were selected by their ability to restore G-1315 to tryptophan prototrophy.

Preparation of Yeast Extracts for Assay of 3',5'-Hydroxylase Activity a. G-1315/pCGP618

Single isolates of G-1315/pCGP618 and a G-1315 revertant that grew on media lacking tryptophan were used to inoculate 50 mL of YNBC [1.2% (w/v) yeast nitrogen base without amino acids (Difco), 2% (w/v) glucose and 0.3% (w/v) Casamino acid (Difco)]and incubated with shaking for 2 days at 30° C. Cells were pelleted by centrifugation and a microsoma] fraction was obtained according to Oeda et al. (1985) except that the spheroplasts were disrupted in 10 the extraction buffer used for the assay of 3',5'-hydroxylase activity in plant tissue. Microsomal pellets were resuspended in 400 μL of buffer A (10 mM Tris-HC1 (pH 7.5), 0.65M sorbitol, 0.1mM DTT, 0.1 mM EDTA) and a 100 μL sample was assayed for 3',5'-hydroxylase activity.

b. G-1315/pCGP620

A single isolate of G-1315/pCGP620 was used to inoculate 20 ml of YNBC which was subsequently incubated for 2 days at 30° C. Cells were collected by centrifugation, washed once with TIE, once with buffer A, and then resuspended in buffer B (10 mM Tris-HCl (pH7.5), 1.2M sorbitol, 0.1 mM DTT, 0.1 mM EDTA) containing zymolyase (0.1 mg/mL) (Seikagakukogyo, Japan). Following incubation for 1 hour at 30° C. the cells were pelleted by centrifugation and resuspended in 400 IL1 of buffer A. The cell suspension was then vortexed with glass beads (diameter=0.4 mm) for 2 minutes and a 100 μl sample was assayed for 3',5'-hydroxylase activity.

Petunia Transformation a. Plant Material

Petunia hybrida (Skr4×Sw63 and Rp57×Rw14) seeds were sterilized in 1.25% (w/v) sodium hypochlorite for 10 rain and rinsed three times in sterile water. Sterilized seeds were soaked in 100 mg/L gibberellic acid (CA$_3$) solution for 16 to 20 hours. They were then germinated for 2 weeks on 10% (w/v) MS (Murashige and Skoog, 1962) medium supplemented with 1% (v/v) sucrose and 0.8% (w/v) Difco Bacto agar. Young seedlings were transferred to MS medium supplemented with 3% (w/v) sucrose for 3 weeks before being transferred to Jiffy peat pellets (Jiffy Products Ltd, Norway), kept under mist and illuminated (135 μE. mercury halide light, 22° C.) for 2 to 3 weeks. These young plants were then transferred to a growth cabinet (68 μE. cool white fluorescent light, 25° C.). For co-cultivation, young leaves were harvested and sterilized in 1.35% (w/v) sodium hypochlorite for 2 rain followed by rinsing three times in sterile water. Leaf tissue was then cut into 25 mm$^2$ squares and precultured on MS media supplemented with 0.05 mg/L kinetin and 1.0 mg/L 2,4-dichlorophenoxyacetic acid (2,4-D) for 24 hours.

b. Co-cultivation of Agrobacterium and Petunia Tissue

Agobacterium turnefaciens strain AGL0 (Lazo et al, 1991) containing the binary vector pCGP90 (FIG. 14) was maintained at 4° C. on MG/L (Garfinkel and Nester, 1980) agar plates with 100mg/L gentamycin. A single colony was grown overnight in liquid medium containing 1% (w/v) Bacto-peptone, 0.5% (w/v) Bacto-yeast extract and 1% (w/v) NaCl. A final concentration of $5 \times 10^8$ cells/mL was prepared the next day by dilution in liquid MS medium containing 3% (w/v) sucrose (BPM). Leaf discs were dipped for 5 minutes into BPM containing AGL0/pCGP90. The leaf discs were then blotted dry and placed on co-cultivation media for 4 days. The co-cultivation medium consisted of SH medium (Schenk and Hildebrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

c. Recovery of transgenic petunia plants

After co-cultivation, the leaf discs were transferred to the following selection media: Skr4×Sw63 discs to fresh MS medium supplemented with 3% (w/v) sucrose, 2 mg/L et-benzylaminopurine (BAP), 100 mg/L kanamycin, 350 mg/L cefotaxime, 0.3% (w/v) Gelrite Gellan Gum (Schweizerhall); Rp57×Rw14 discs to the same medium, containing 0.5 mg/L BAP and a-naphthalene acetic acid (NAA) instead of 2 mg/L BAP. After 3 weeks, regenerating explants were transferred to fresh medium. Adventitious shoots which survived the kanamycin selection were isolated and transferred to BPM containing 100 mg/L kanamyein and 350 mg/L cefotaxime for root induction. All cultures were maintained under a 16 hr photoperiod (60 μE. cool white fluorescent light) at 23±2° C. When roots reached 2-3 cm in length the transgenie petunia plantlets were transferred to autoclaved Debco 51410/2 potting mix in 8 cm tubes. After 4 weeks plants were replanted into 15 cm pots using the same potting mix and maintained at 23° C. under a 14 hour photoperiod (300 lat. mercury halide light).

Tobacco Transformation a. Plant Material

*Nicotiana tabacum* (cv. Xanthi) stock plants were maintained on MS medium supplemented with 1 mg/L indolebutyric acid (IBA) and solidified with 0.25% (w/v) Gelrite. Leaf tissue was cut into 25 mm² squares and placed onto MS medium containing I mg/L BAP and 0.5 mg/L indoleacetic acid (IAA) for 24 hours.

b. Co-cultivation of *Agrobacterium* and tobacco tissue

Co-cultivation was carried out as previously described for petunia.

c. Recovery of transgenie tobacco plants

After co-cultivation, leaf discs were transferred to MS medium supplemented with 1 mg/L BAP, 0.5 mg/L I. AA, 100 mg/L kanamycin and 350 mg/L cefotaxime (selection medium). Regenerating explants were transferred to fresh selection medium after 2-3 weeks. Adventitious shoots which survived the kanamycin selection were isolated and transferred to MS medium containing 1 mg/L IBA, 100 mg/L kanamycin and 350 mg/L cefotaxime for root induction. x, When roots reached 2-3 cm in length the transgenic tobacco plantlets were transplanted to soil as described for petunia.

Anthocyanidin analysis

Prior to HPLC analysis the anthocyanin molecules present in petal extracts were acid hydrolysed to remove glycosyl moieties from the anthocyanidin core. The hydroxylation pattern on the B ring of the anthocyanin pigments was determined by HPLC analysis of the anthocyanidin core molecule. The HPLC system used in this analysis was a Hewlett-Packard 1050 equipped with a multiwavelength detector (MVvrD). Reversed phase chromatographic separations were performed on a Spherisorb S5 ODS2 cartridge column, 250 mm×4 mm ID.

a. Extraction of anthocyanins and flavonoicts

Flower pigments were extracted from petal segments (ca. 50 mg) with 5 ml of methanol containing 1% (v/v) of aqueous 6M hydrochloric acid. Extracts were diluted with water (1:9) and filtered (Millex HV, 0,451a) prior to injection into the HPLC system.

b. Hydrolysis of anthocyanins

Crude methanolic extracts (100 µL,) obtained in a. above were evaporated to dryness in Pierce Reacti-Vials using a stream of dry nitrogen at room temperature. The residues were dissolved in 200µL 2M HCl, vials were capped and then heated at 100° C. for thirty minutes. Hydrolysis mixtures were diluted with water (1:9) and filtered (Millex HV, 0.45µ) prior to HPLC analysis.

c. Chromatography

Separation of flower pigments was effected via gradient elution using the following system:

Solvent A: (triethylamine: conc. $H_3PO_4$: $H_2O$) (3:2.5:1000)
Solvent B: acetonitrile
Gradient Conditions: 5% B to 40% B over 20 minutes
Flow Rate: 1 ml/min
Temperature: 35° C.
Detection: MWD with simultaneous data acquisition at 280, 350 and 546nm.

The anthocyanidin peaks were identified by reference to known standards.

2. CLONING AND ANALYSIS OF 3',5'-HYDROXYLASE

Characterization of the 3',5'-Hydroxylase Enzyme
a. Developmental Regulation

Extracts of *P. hybrida* cv. OGB petals harvested from flowers at the different stages of development defined above were assayed for 3',5'-hydroxylase activity.

3',5'-Hydroxylase enzyme activity in OGB petals was found to be developmentally regulated during maturation of the corolla (FIG. 2B). This developmental profile paralleled the expression of other genes involved in flavonoid biosynthesis. Activity of the 3',5'-hydroxylase enzyme and expression of chalcone synthase (CHS), chalcone flavanone isomerase (CHI), dihydroflavonol reductase (DFR) genes peaked around stages 3 to 4 of flower development.

b. Induction of 3',5'-Hydroxylase Activity in Leaf Tissue

Genes of the flavonoid pigment biosynthetic pathway are not normally expressed in leaf tissue. However, synthesis of delphinidin pigments was induced in OGB leaves by incubation in a 2% (w/v) glucose solution in high light. Under these conditions, 3',5'-hydroxylase enzyme activity can be detected in OGB leaf tissue. Maximal induction of enzyme activity was shown to occur after 96 hours of the glucose/high light treatment. Under these conditions the expression of several other pigment biosynthesis genes was also induced to levels comparable to those observed in emerging petals. It was concluded from these results that the Ftfl and/or Hf2 genes are induced in glucose/high light treated leaf tissue.

c. Evidence that the 3',5'-Hydroxylase Belongs to the Cytochrome P450 Class of Enzymes 3',5'-Hydroxylase activity in OGB petals was shown to be associated with the microsomal fraction and dependent upon the presence of NADPH. Activity could be inhibited by treatment of the microsomes with carbon monoxide and by two inhibitors that specifically inactivate cytochrome P450 enzymes: tetcyclasis and 1-aminobenzotriazine (Talon et al, 1988; Matthews et al, 1985; Rademacher et al, 1987).

Construction of a cDNA Library Enriched for Cytochrome P450 Sequences

Translation of cytochrome P450 mRNAs occurs on membrane-bound polysomes (Takemori and Kominami, 1989). Therefore, in order to enrich for cytochrome P450 sequences (including 3',5'-hydroxylase sequences) a cDNA library was constructed using membrane-bound polysomal RNA isolated from OGB petals of stage 3 to 4 flowers. Isolation of the petal RNA from stage 3 to 4 flowers, ensured that 3',5'-hydroxylase sequences were maximally represented in the library since 3',5'-hydroxylase activity had been shown to be maximal at this stage of development (see above and FIG. 2B). The resultant library, designated eDNA library #1, contained 250,000 primary recombinants.

PCR Amplification of a Petunia Petal Cytochrome P450 cDNA

A large number of cytochromes P450 have been sequenced, from organisms as diverse as vertebrates, fungi, insects, bacteria and one plant (Nebert et al, 1991, Bozak et al, 1990). A characteristic of all these enzymes is the existence of a number of small regions of sequence conservation, especially around the cysteine residue involved in haem binding. The amino acid sequence F(G,S)XGXRXCXG is present in the haem-binding domain of nearly all microsomal cytochromes P450 sequenced to date, where X can be any amino acid (FIG. 3). This consensus sequence was compared with the NBRF protein database, using the FASTA program (Pearson and Lipman, 1988), to determine the frequency of occurrence of amino acids around this area for all of the microsomal cytochrome P450 sequences in the database. This analysis showed that the most common amino acid sequence for each position around the haem-binding domain was:

FMPEGAGXRXCLG

An oligonucleotide was designed to hybridize to a gene encoding the underlined sequence and similar sequences. This oligonucleotide, designated oligo 1, is shown below:

5'-GGAAGCTTATICCITT(T/C)GGIGCIGG-3'

The underlined portion is additional sequence which includes a HindIII recognition site to facilitate directional cloning of PCR products. The inclusion of deoxyinosine (I) covered the different possibilities for codon usage where more than two codohs could encode the same amino acid. Deoxyinosine base-pairs with similar efficiency to A, T, G and C (Martin et al, 1985; Ohtsuka et al, 1985).

Plasmid DNA obtained from eDNA library #1 as described in the Materials and Methods was used as a template for the amplification of a 360 bp cytochrome P450 related sequence using oligos 1 and 2 (FIG. 3). Oligo 2 corresponded to the −20 primer (Stratagene) plus a GCN4 binding site (Lew and Kemp, 1989) at the 5' end. The PCR fragment was cloned into pBluescript and the resulting plasmid was designated pCGP450. The 5'region of pCGP450 encoded a polypeptide sequence with significant homology to previously sequenced cytochrome P450 molecules.

Isolation of Cytochrome P450 Homologues from a Petunia Petal cDNA Library

Plasmid pCGP450 was used to screen cDNA library #1 (60,000 plaques) for related clones. Two consecutive hybridizations under conditions of high and low stringency were used to detect both sibling clones of pCGP450 and a second group of cytochrome P450 cDNAs. A representative cDNA clone of each of the sibling groups was selected for subsequent analyses. The pCGP450 sibling was designated pCGP142 and the representative of the second group was designated pCGP147. A SaLI - Er, mRI fragment that included only the coding sequences of pCGP147 was then used to re-probe 16,000 plaques from eDNA library #1 at low stringency. A total of 20 clones that hybridized to the probe were sequenced, allowing two further cytochrome P450 homologues to be identified: pCGP158 and pCGP160 (FIG. 4A).

Isolation of an Additional Petal Cytochrome P450 Homologue by PCR

Sequence information from around the putative haem-binding domain of the petunia clones pCGP142, pCGP147 and a previously sequenced avocado cytochrome P450 sequence (O'Keefe and Leto, 1989; Bozak et al, 1990) was used, as described in the Materials and Methods, to design a second degenerate oligonucleotide (oligo 3) which covered amino acid sequences encoded by at least two of the three cytochrome P450 clones. This oligonucleotide was used to amplify related sequences by PCR using eDNA library #1 as the template and oligo 4 as the second primer (FIG. 3B). Reaction products in the size range 250–500 bp were isolated as described in Materials and Methods and cloned into the ddT-tailed pBluescript vector described by Holton and Graham (1991). The cloned PCR fragments were sequenced and shown to encode a fifth cytochrome P450 homologue. One clone, designated pCGP454, was chosen for further analysis.

Isolation of Further Cytochrome P450 Homologues from cDNA Library #1

A mixed probe of $^{32}$P-labelled DNA fragments that included the coding regions of the cytochrome P450 homologues pCGP142, pCGP147, pCGP158 and pCGP160 and the eDNA insert from pCGP454 (FIGS. 4B to 4H) was used to screen 50,000 recombinants from eDNA library #1 for related sequences. A total of 152 hybridizing clones were detected under low stringency hybridization and washing conditions. A further 13 different cytochrome P450 homologues were identified by sequence analysis of DNA isolated from the hybridizing clones. Two closely related sibling groups were distinguished amongst these clones. The coding regions of each of the two groups showed 94% homology or similarity at the DNA level. Two representatives of one sibling group, pCGP174 (FIG. 5A) and pCGP176, and one representative of the other sibling group, pCGP175 (FIG. 5B), were chosen for further study.

Northern and RFLP Analysis of the Cytochrome P450 Homologues

Northern and RFLP analyses were used to distinguish which cytochrome P450 homologues had the molecular characteristics of a cDNA encoding a 3',5'hydroxylase. There are two genetic loci in P. hybrida, Hf1 and Hf2, that control 3',5'-hydroxylase activity (de Viaming eta/, 1984; Wiering, 1974). Hf1 is expressed in both the limb and the tube of P. hybrida flowers and gives rise to much higher levels of 3',5'-hydroxylase activity than does Hf2 which is only expressed in the limb. Petunia 3',5'-hydroxylase activity is also developmentally and spatially regulated. Under normal growth conditions, the enzyme can only be detected in petal tissues, increasing to maximal levels around stages 3–4 of flower development and then declining in the fully open flower (stage 5; see FIG. 2(B)). Activity can also be induced in leaf tissue under certain stress conditions such as the glucose/high light treatment described above. Accordingly, a eDNA clone encoding a 3',5'-hydroxylase was expected to have an expression profile on RNA blots that paralleled the enzyme activity profile. It was also expected that a eDNA clone encoding a P. hybrida 3',5'-hydroxylase would map to either the Hf1 or HF2 loci. Hf1 has been mapped to chromosome I of the P. hybrida genome and is linked to the Ph1 locus (Cornu, 1984; Cornu et al, 1990) while Hf2 is closely linked to Po on chromosome V (Wallroth et al, 1986). RFLP analysis of DNA isolated from a $F_2$ population of plants derived from a cross between the inbred lines V23 (Hf1/Hf1, Hf2/Hf2) and R51 (hf1/hf1, hL2/hf,2) was used to obtain linkage data for the various cytochrome P450 homologues. An Hf1/− genotype was assigned to $F_2$ plants that had 3',5'-hydroxylase activity in the flower tube. In addition, it was possible to assign an Hf1/Hf1 genotype to plants in the $F_2$ population based on linkage to the ph1 gene which influences the pH of the petal vacuole (Wiering and de Viaming, 1984).

The V23 parent line (F-If1/Hf1) also had a 1/ph1 genotype which results in a petal homogenate pH of approximately 6.2. Since Phi/− plants have a petal homogenate pH of 5.3 it was possible to distinguish phi/phl (Hf1/Hf1) plants within the R51×V23 $F_2$ population by assaying the pH of petal homogenates.

The linkage between the and Po loci was used to distinguish candidate Hf2 clones. The Po locus has been shown to correspond to the P. hybrida chiA gene which encodes the enzyme chatcone flavanone isomerase (van Tunen et al, 1991). A eDNA clone of chi-A could therefore be used in the RFLP analysis to assign a Po or po genotype to individuals in the $F_2$ population. Since V23 has an Hf2/Hf2, po/po genotype it was possible to determine linkage to the Hf2 locus by co-segregation of the V23-like and R51-like RFLP patterns with the po and Po patterns detected by the chi-A probe.

cDNA fragments that corresponded to the 3' untranslated region of the cytochrome P450 homologues were used to probe RNA blots and Southern blots of genomic DNA isolated from individual plants in V23×RS1 $F_2$ population. By this analysis it was shown that the genes corresponding to cDNA clones pCGP174 and pCGP175 were expressed in a manner that paralleled 3',5'-hydroxylase activity. Furthermore, the gene corresponding to pCGP174 was shown to be closely linked to the I-Il1 locus and pCGP175 was linked to the Hf2 locus.

a. pCGP 174

A 330bp HindIII-KpnI3'fragment from clone pCGP174 (FIG. 5A) gave a pattern of hybridization on both RNA and DNA blots that suggested that this clone corresponded to the Hfl locus (FIG. 6). The gene was expressed in both limb and tube tissues and had a developmental profile that paralleled 3',5'-hydroxylase activity, peaking in Stage 3 petal limbs. No expression was detected in leaf, but was induced in this tissue by the glucose/high light treatment. Furthermore, there was no detectable expression of the gene tn the petal tissue of the hf1/hf1 mutant lines R51 or Sw63. By contrast, relatively high levels of expression were detected in the Hf1/Hf1 lines V23 and Th7 and the V23×RS1 hybrid (FIG. 6A).

On Southern blots of genomic DNA digested with XbaI, the 330bp HindIII - KpnI 3'fragment from pCGP174 detected two RFLPs that segregated independently in the V23×RS1F=population. RFLP #1 corresponded to strongly hybridizing DNA bands while RFLP #2 corresponded to weakly hybridizing bands (see FIG. 6B). Eleven out of 12 plants that had been assigned a 12111/12111 genotype had a V23- like pattern for RFLP #1 and 49 out of 49 plants that had 3',5'-hydroxylase activity in the tube had either a V23 or VR - like pattern for RFLP #1. In addition, for a total of 32 plants, there was complete co-segregation of the V23, VR and R51 RFLP patterns for chi-A (po) with the corresponding patterns of RFLP #2.

These data provided strong evidence that pCGP174 encoded a 3',5'hydroxylase and corresponded to the Hfl locus (RFLP #1 ) and that the 3' probe cross-hybridized to the Hf2 locus (RFLP #2).

b. pCGP175

A 320 bp HindIII/XhoI 3' fragment from clone pCGP175 (FIG. 5B) gave a pattern of hybridization on both RNA and DNA blots that suggested that this clone corresponded to the Hf2 locus (FIG. 7). The Northern analysis showed that the gene was developmentally regulated in a similar way to pCGP174, with maximal expression in Stage 30GB petal limbs, however no expression was detected in OGB tube tissue. The gene was also expressed in the petal tissue of V23 (Hf2/Hf2), Th7 (Hf2/Hf2) and the V23×RS1 hybrid (FIG. 7A).

On Southern blots, the 320bp HindIII/XhoI fragment from pCGP175 hybridized to the same genomic fragments produced by digestion of V23 and RS1 genomic DNA that weakly hybridized to the pCGP174 3'probe (RFLP #2). There was complete co-segregation of the V23-, VR- and R51 -like RFLP patterns detected by the pCGP175 3' probe and the corresponding RFLP patterns for chi-A (Po) (FIG. 7B).

Yeast expression experiments (see below) subsequently confirmed that pCGP175 and a sibling of pCGP174 (pCGP176) both encoded a 3',5'hydroxylage. In addition, expression of a full-length version of pCGP174 in an hf1/hf1, hf2/hf2 Petunia mutant resulted in increased 3',5'-hydroxylage activity and production of 3',5'-hydroxylated anthocyanins above the low basal levels normally found in the non-transgenic plant. Taken together with the RFLP results, it was concluded from these data that pCGP174 correspond to the Hfl locus and pCGP175 correspond to the HI2 locus.

Isolation of Full-Length Hfl cDNA Clones and Sequence Analysis

From preliminary sequence analysis it wag shown that pCGP174 did not represent a full-length clone of the corresponding transcript while pCGPt75 included a putative initiation codon and wag presumed to be a full-length cDNA. Sequence analysis also showed that pCGP176 wag a longer version of pCGP174 and included an ATG codon 17bp from the 5'end. However, from this analysis alone it was not possible to confidently predict whether pCGP176 included the entire coding region of this gene. Accordingly, eDNA library #2 was screened for longer clones of the pCGP174/pCGP176 sibling group. Approximately $1.5 \times 10^5$ recombinants from cDNA library #2 were screened for clones that hybridized to the 0.33 kb HindIII - KpnI 3'fragment from pCGP174. Two hybridizing clones, designated pCGP601 and pCGP602 were chosen for further analysis. Both pCGP601 and pCGP602 included presumptive translation initiation codons, but pCGP602 encoded a longer 5' untranslated region.

A restriction enzyme map of pCGP602, indicating the methodology adopted for sequencing the clone and the oligonucleotide primer sequences used to obtain overlapping sequence information, is shown in FIG. 8.

The nucleotide sequence and deduced amino acid sequence of the sibling clones pCGP176 and pCGP602 are shown in FIG. 9. Similarly, FIG. 10 shows the nucleotide sequence and deduced translation product of pCGP175.

Using an alignment generated by the LFASTA program (Pearson and Lipman, 1988), the amino acid sequences encoded by the petunia 3',5'-hydroxylase genes were found to share 94% positional identity. The nucleotide sequences are 94% identical. Based on the classification scheme for cytochromes P450, this sequence similarily would place both genes in the same family/sub-family. Because the 3',5'-hydroxylase amino acid sequences share less than 40% identity with any previously characterized member of the cytochrome P450 superfamily, the corresponding genes belong to a new P450 family separate from all other P450 genes.

Expression of pCGP175 cDNA in Yeast

The eDNA insert from pCGP175 was ligated in a sense orientation behind the glyceraldehyde-3-phosphate dehydrogenase promoter in the yeast vector pYG/22m. The resulting construct, designated pCGP618 (FIG. 11), was transformed into the yeast strain G-1315 (Ashikari et al, 1989). A single transformant was grown in 50 mL of YNBC at 30° C. for 2 days. A microsomal fraction prepared from this culture was shown to have 3′,5′-hydroxylase activity while an equivalent fraction prepared from non-transformed yeast had no activity (FIG. 12). From this it was concluded that the eDNA insert from pCGP175 encoded a 3′,5′-hydroxylase.

Expression of pCGP176 cDNA in Yeast

The cDNA insert from pCGP176 was ligated in a sense orientation behind the glyceraldehyde-3-phosphate dehydrogenase promoter in the yeast vector pYGA22m. The resulting construct, designated pCGP620 was transformed into the yeast strain G-1315. An extract prepared from the transformed yeast was shown to have 3′,5′-hydroxylase activity while an equivalent fraction prepared from non-transformed yeast had no activity (FIG. 13). From this it was concluded that the eDNA insert from pCGP176 encoded a 3′,5′-hydroxylase.

Expression of an Hf1 cDNA a. Expression in the hf1/hf1, hf2/hf2 *P. hybrida* F₁ hybrid Skr4×Sw63 The pCGP602 cDNA insert was ligated behind the Mac promoter of the Ti-binary vector pCGP293. The resulting construct, designated pCGP90 (FIG. 14), was introduced into the F₁ *Petunia* hybrid Skr4×Sw63 using *Agrobacterium* mediated gene transfer. Leaf discs of Skr4×Sw63 were co-cultivated with AGL0/pCGP90 and integration of the pCGP602 cDNA insert in the Skr4×Sw63 genome was confirmed by Southern analysis of plants obtained after kanamycin selection.

The transgenic plants had significantly higher levels of both 3′,5′-hydroxylase enzyme activity (FIG. 15) and 3′,5′-hydroxylated anthocyanins (Table 3A) than the non-transgenic Skr4×Sw63 hybrid. Although Skr4×Sw63 is homozygous recessive for both the Hf1 and Hf2 genes these mutations do not completely block enzyme production as low levels of 3′,5′-hydroxylase activity were detected in Skr4×Sw63 petal extracts (FIG. 15). In addition, low levels (100 μg/gm) of malvidin were detected in acid hydrolysed Skr4×Sw63 petal extracts (Table 3A). Introduction of the Hf1 cDNA significantly increased the level of 3′,5′-hydroxylase activity in petal limb tissue (FIG. 15) and acid hydrolysed extracts of petals from the transgenic plants had four times the level of malvidin detected in the non-transgenic control (Table 3A).

b. Expression in Nicotiana tabacurn cultivar Xanthi

Tobacco (*N. tabacura* cv Xanthi) flowers produce cyanidin as the sole anthocyanidin. Transformation of tobacco with pCGP90 led to the accumulation of significant amounts of delphinidin in the flowers, in addition to cyanidin (shown in Table 3A).

TABLE 3A

| | Pigment Analysis | | |
|---|---|---|---|
| | Anthocyanidin levels found in acid hydrolysed petal extracts | | |
| Plant | Malvidin (μg/gm petal) | Cyanidin (μg/gm petal) | Delphinidin (μg/gm petal) |
| Petunia Skr4 × Sw63 | 100 | nd¹ | nd |
| Skr4 × Sw63/pCGP90 | 410 | nd | nd |
| Tobacco non-co-cultivated control | nd | 272 | nd |
| Transgenic tobacco | nd | 229 | 36 |

¹not detected c. Expression in the hf1/hf1, hf2/hf2 *P. hybrida* F₁ hybrid Rp57×Rw14 The petunia line Rp57×Rw14 was transformed using pCGP90 and a procedure similar to that used for Skr4×Sw63. Transgenie flowers produced considerable mounts of petunidin and malvidin which were not detectable in the non-transformed plants (Table 3B). Petunidin and malvidin are both methylareal derivatives of delphinidin.

TABLE 3B

| Pigment Analysis of high pH line Rp57 × Rw14. | | | | |
|---|---|---|---|---|
| | Percentages of anthocyanidins found in acid hydrolysed petal extracts | | | |
| Plant | Cyanidin (%) | Peonidin (%) | Petunidin (%) | Malvidin (%) |
| Petunia Rp57 × Rw14 | 5.0 | 95.0 | 0 | 0 |
| Rp57 × Rw14/ pCGP90 | 0 | 45.2 | 7.8 | 47.0 |

The expression of the introduced Hf1 cDNA in the Skr4×Sw63 hybrid had a marked effect on flower colour. The carpel and stamen tissue of the nontransgenie flowers are white whereas these same tissues in the transgenie plants were a blue/purple colour. In addition, expression of the Hf1 cDNA in the Skr4×Sw63 hybrid conferred a deep pig/violet hue to the corolla which is normally very pale pink. In the case of tobacco, the production of delphinidin derivatives led to a minor blueing of sensing flowers. Expression of the Hf1 eDNA in the Rp57×Rw14 hybrid again had a marked effect on flower colour. Non-transgenic Rp57×Rw14 flowers are pink, with penicillin being the major anthocyanidin present (see Table 3B). Transformation with Hf1 cDNA led to a marked blueing of flower colour.

The colour changes observed may also be described in terms of numbers from the Royal Horticultural Society's Colour Chart. In general, the changes can be described as moving the colour from the pale-to-mid pink hues of 60C/D 65C/D, to the darker bluer/purpler hues represented by many, but not all, of the colour squares between 70 and 85. Although not wishing to limit the possible colour changes which may be achieved, some of the colours observed in the Skr4×Sw63 hybrid could be described, approximately, as having changed from 65B (untransformed) to 70B and to 74B (both transformed). Likewise, several in the Rp57×Rw14 hybrid might be described as moving from 64C to 72B to 77B and to 82B. It should be remembered that other biochemical and physiological conditions will affect the individual outcome and the citing of specific colours achieved should not be interpreted as defining the possible range.

Detection of Putative 3′,5′-hydroxylase Gene Sequences in Other Plant Species The presence of 3′,4′,5′-hydroxylated flavonoids is correlated with the presence of 3′,5′-hydroxylase activity and therefore the 3′,5′-hydroxylase gene. It would be expected that these genes from other species would hybridize with the petunia 3',5'-hydroxylase gene under conditions of low stringency. RNA (FIG. 16) and/or DNA (FIG. 17) was isolated from a number of delphinidin-producing plants, probed with 32P-labelled Hfl eDNA and washed under 5 different conditions of stringency. Hybridizing bands were detected in every example. Therefore, the isolation of 3',5'-hydroxylase genes from other delphinidin-producing plants should be possible using a petunia 3',5'-hydroxylase gene as a probe.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES:

Asen, S., Stewart, R. N. and Norris, K. H. *Phytochemistry* 14: 2677–2682, 1975.

Asen, S., Criesbach, R. J., Norris, K. H. and Leonhardt, B. A. *Phytochemistry* 25: 2509–2513, 1986.

Ashikari, T., Kiuchi-Goto, N., Tanaka, Y., Shibano, Y., Amachi, T., and Yoshizumi, H. *Appl. Microbiol. Biotechnol.* 30:515–520, 1989.

Aviv, H. and Leder, P., *Proc. Natl. Acad. Sci. USA* 69:1408–1412, 1972.

Beale, G. H. *Journal of Genetics* 40(3): 337–358, 1940.

Bethesda Research Laboratories. BRL pUG host: *E. coli*DHα™ competent cells. *Bethesda Res. Lab. Focus.* 8(2): 9, 1986.

Bozak, K. R., Yu, H., Sirevag, R. and Christoffersen, R. E., *Proc. Natl. Acad. Sci. USA* 87: 3904–3908, 1990.

Bullock, W. O., Fernandez, J. M. and Short, J. M. *Biotechniques* 5: 376, 1987.

Comai, L., Moran, P. and Maslyar, D., *Plant Molecular Biology* 15: 373–381, 1990.

Cornu, A., Genetics. In: *Petunia* Sink, K. C. (Ed). Springer-Verlag, Berlin, Germany pp 35–47, 1984.

Cornu, A., Farcy, E., Maizonnier, D., Haring, M., Veerman, W. and Gerats, A.G.M. In *Genetic maps - Locus maps of complex genomes* 5th edition, Stephen J. O'Brien (Ed), Cold Spring Harbor Laboratory Press, USA, 1990.

Dellaporta, S. J., Wood, J. and Hick, J. B. Plant Mol. Biol. Rep. 1: 19–21, 1983.

De Viaming, P., Gerats, A.G.M., Wiering, H. and Wijsman, H. J. W. *Plant Mol. Biol. Rep.* 2(2): 21–42, 1984.

Doodeman, M., Gerats, A.G.M., Schram, A. W., de Viaming, P. and Bianchi, F. Theor. Appl. Genet. 67: 357–366, 1984.

Ebel, J. and Hahlbrock, K., In *The Flavonoids: Advances in Research Since 1980*. Harborne, J. B. (Ed.), Academic Press, New York, USA, 641–679, 1988.

Forkmann, G. Plant Breeding 106: 1–26, 1991.

Formann, G. and Stotz, G. Z. Naturforsch 36c: 411–416, 1981.

Garfinkel, D. J. and Nester, E. W. *J. Bacteriol.* 144:732–743, 1980.

Hagmann, M., Heller, W. and Grisebach, H. *Eur. J. Biochem.* 134: 547–554, 1983.

Hahlbrock, K. and Grisebach, H. *Annu. Rev. Plant Physiol.* 30: 105–130, 1979.

Hanahan, D. *J. Mol. Biol.* 166: 557, 1983.

Harborne, J. B. and Simmonds, N. W. *Annu. Rep. John Innes Inst.* 53: 29–30, 1962.

Heller, W. and Forkmann, G. In: *The Flavonoids, Advances in Research Since 1980*. Harborne, J. B. (Ed.), Academic Press, N.Y., 1988.

Holton, T. A. and Graham, M. W. *Nucleic Acids Research* 19: 1156, 1991.

Inoue, H., Nojima, H. and Okayarea, H. Gene 96: 23–28, 1990.

Ito, H., Fukuda, Y., Murata, K. and Kimura, A. *J. Bacteriol.*, 153: 163–168, 1983.

Jefferson, R. A., Kavanagh, T. A. and Bevan, M. W. *EMBO J.* 6(13): 3901–3907, 1987.

Koes, R. E., Spelt, C. E., Reif, H. J., van den Elzen, P. J. M., Veltkamp, E. and Mol, J. N. M. *Nucl. Acids Res.* 14(13):. 5229–5239, 1986.

Larson, R. L. and Bussard, J. B. *Plant Physiol.* 80: 483–486, 1986.

Lazo, G. R., Pascal, A. S. and Ludwig, R. A. *Bio/technology* 9: 963–967, 1991.

Lew, A. M. and Kemp, D. J. *Nucl. Acids Res.* 17(14):. 5859–5860, 1989.

McBride, K. E. and Summerfelt, K. R. *Plant Molecular Biology* 14:269–276 1990.

Martin, F. M., Castro, N. M., Aboula-ela, F., Tinoco, I. *Nucl. Acids Res.* 13: 927–8938, 1985.

Matthews, J. M., Dostat, L. A. and Bend, J. R. J. *Pharmacology and Experimental Therapeutics* 235(186–190, 1985.

Merrifield, J. *Am. Chem. Soc.* 85:2149, 1964.

Murashige, T. and Skoog, F. *Physiol. Plant* 15: 73–97, 1962.

Nebert, D. W., Nelson, D. R., Coon, M. J., Estabrook, R. W., Feyereisen, R., Fujii-Kuriyama, Y., Gonzalez, F. J., Guengerich, F. P., Gunsalus, I. C. Johnson, E. F., Loper, J. C., Sato, R., Waterman, M. R., Waxman, D. J. *DNA and Cell Biology* 10: 1–14, 1991.

Norrander, J., Kemp, T. and Messing, J. Gene 26: 101, 1983.

Oeda, K., Sakaki, T., and Ohkawa, H. DNA 4: 203–210, 1985.

O'Keefe, D. P. and Leto, K. J. Plant Physiol. 89: 1141–1149, 1989.

Ohtsuka, E., Matsuki, S., Ikehara, M., Takahashi, Y. and Matsubara, K. *J. Biol. Chem.* 260(5): 2605–2608, 1985.

Pearson, W. R. and Lipman, D. J. *Proc. Natl. Acad. Sci.* USA 85: 2444–2448, 1988.

Rademacher, W., Fritsch, H., Graebe, J. E., Sauter, H. and Jung, J. *Pesticide Science* 21: 241–252, 1987.

Sambrook, J., Fritsch, E. F. and Maniatis, T. *Molecular Cloning: A Laboratory Manual* (2nd edition). Cold Spring Harbor Laboratory Press, USA, 1989.

Sanger, F., Nicklen, S. and Coalson, A. *Proc. Natl. Acad.* Sci. USA 74: 5463–5467, 1977.

Schenk, R. U. and Hilderbrandt, A. C. Can. J. Bot. 50: 199–204, 1972.

Schram, A. W., Jonsson, L. M. V. and Bennink, G. J. H. Biochemistry of flavonoid synthesis in *Petunia hybrida*. In: *Petunia* Sink, K.C. (ed.) Springer-Verlag, Berlin, Germany pp 68–75, 1984.

Stafford, H. A. *Flavonoid Metabolism* CRC Press, Inc. Boca Raton, Fla., USA, 1990.

Stotz, G. and Forkmann, G. Z. Naturforsch 37c: 19–23, 1982.

Stotz, G., de Viaming, P., Wiering, H. and Forkmann, G. *Theor. Apppl. Genet.* 70: 300, 1985.

Takeda, K., Kubota, R. and Yagioka, C. *Phytochemistry* 24: 1207, 1985.

Takemori, S. and Kominami, S. *Cytochrome P450.* Tokyo University Press, Japan, 1989.

Taton, M., Ullman, P., Beneveniste, P. and Rahier, A. *Pesticide Biochemistry and Physiology* 30:. 178–189, 1988.

Turpen, T. H. and Griffith, O. M. *BioTechniques* 4: 11–15, 1986.

van Tunen, A. J., Gerats, A. G. M. and Mol, J. N. M. *Plant Mol. Biol. Rep.* 8: 50–59, 1990.

van Tunen, A. J., Koes, R. E., Spelt, C. E. van der Krol, A. R., Stuitje, A. R. and Mol., J. N. M. *EMBO J.* 7(5): 1257–1263, 1988.

van Tunen, A. J., Mur, L. A., Recourt, K., Gerats, A. G. M. and Mol., J. N. M. *The Plant Cell* 3: 39–48, 1991.

von Wettstein-Knowles, P. *Hereditas* 60: 317–346, 1968.

Vercruysse, S. A. R., Delcour, J. A. and Dondeyne, P. J. *Chromatography* 324: 495–497, 1985.

Wallroth, M., Gerats, A. G. M., Rogers, S. C., Fraley, R. T. and Horsch, R. B. *Mol. Gen. Genet.* 202: 6–15, 1986.

Wiering, H. and De Viaming, P. Inheritance and Biochemistry of Pigments. In: *Petunia Sink,* K.C. (Ed.), Springer-Verlag, Berlin, Germany pp 49–65, 1984.

Wiering, H. *Genen Phaenen* 17(1-2): 117–134, 1974

Yanisch-Perron, C., Vieira, J. and Messing, J. *Gene* 33: 103, 1985.

---

We claim:

1. An isolated nucleic acid encoding a 3',5'-hydroxylase capable of hydroxylating dihydrokaempferol (DHK).

2. The isolated nucleic acid according to claim 1 wherein said nucleic acid is DNA or cDNA.

3. The nucleic acid according to claim 1 wherein said 3'5'-hydroxylase petunia, verbena, delphinium, grape, iris, freesia, hydrangea, cyclamen, potato, pansy or eggplant origin.

4. The isolated nucleic acid according to claim 3 wherein said 3'5-hydroxylase is of petunia origin.

5. The isolated nucleic acid isolate according to claim 4 comprising the nucleotide sequence set forth in SEQ. ID. NO.: 28 or ID NO: 24.

6. A vector comprising the isolated nucleic acid according to any one of claims 1, 2 and 3-5.

7. The vector according to claim 6 wherein said vector is a plant transformation vector.

8. The vector according to claim 7 wherein said vector is pCGP90, shown in FIG. 11.

9. A method for producing a transgenic plant capable of expressing a recombinant 3',5'-hydroxylase wherein said hydroxylase is capable of hydroxylating dihydrokaempferol (DHK) said method comprising introducing into a cell of a plant that does not endogenously product 3',5'-hydroxylase the nucleic acid according to, any one of claims 1, 2 and 3-5 regenerating a transgenic plant from said cell and growing said transgenic plant for a time and under conditions sufficient to permit the expression of said nucleic acid.

10. The method according to claim 9 wherein said transgenic plant is a rose, petunia, chrysanthemum, carnation, gerbera or tobacco.

11. The method according to claim 10 wherein said transgenic plant is a rose or petunia.

12. A method for producing a transgenic petunia plant with reduced levels of 3',5'-hydroxylase relative to endogenous levels, said method comprising introducing the nucleic acid of any one of claims 1, 2 and 3-5 in the antisense orientation into the cell of a *petunia* plant that endogenously products a 3',5'-hydroxylase wherein said hydroxylase is capable of hydroxylating dihydrokaempferol, regenerating a transgenic plant from said cell and growing said transgenic plant for a time and under conditions to permit the expression of said isolated nucleic acid.

13. A transgenic *petunia* plant comprising the nucleic acid of any one of claims 1, 2 and 3–5 in the antisense orientation wherein said plant exhibits reduced levels of 3′,5′-hydroxylase relative to native levels.

14. A transgenic petunia plant comprising the isolated nucleic acid of any one of claims 1, 2, and 4–6 wherein said transgenic plant is capable of expressing said isolated nucleic acid.

15. A transgenic tobacco plant comprising the isolated nucleic acid of any one of claims 1, 2, and 4–6 wherein said transgenic plant is capable of expressing said isolated nucleic acid.

16. A transgenic carnation plant comprising the isolated nucleic acid of any one of claims 1, 2, and 4–6 wherein said transgenic plant is capable of expressing said isolated nucleic acid.

* * * * *

UNITED STATES PATENT AND TRADEMARK OFFICE
CERTIFICATE OF CORRECTION

PATENT NO. : 5,349,125

DATED : September 20, 1994

INVENTOR(S) : Timothy A. Holton, et al.

Page 1 of 18

It is certified that error appears in the above-indentified patent and that said Letters Patent is hereby corrected as shown below:

Title page, item [57], line 6: "transgenie" should read --transgenic--

Column 1, line 21: "nongst" should read --Amongst--

Column 1, line 38: "Iocalised" should read --localised--

Column 1, line 41: "cornplexation" should read --complexation--

Column 1, lines 55: "tiaranone" should read --flavanone--

Column 1, line 64: "3-hydroxylase)" should read --(3'-hydroxylase)--

Column 2, lines 18-19: "vertebrates." should read --vertebrates,--

Column 3, lines 11, 31-32, 33, 38 & 67: "arnino" should read --amino--

Column 4, line 19: "routants" should read --mutants--

Column 4, lines 52-53: "hornology" should read --homology--

UNITED STATES PATENT AND TRADEMARK OFFICE
CERTIFICATE OF CORRECTION

PATENT NO.    : 5,349,125
DATED         : September 20, 1994
INVENTOR(S)   : Timothy A. Holton, et al.

It is certified that error appears in the above-indentified patent and that said Letters Patent is hereby corrected as shown below:

```
      Column 4, line 53:   "father"  should read  --further--
      Column 5, line 14:   "Storz"   should read  --Stotz--
      Column 5, line 27:   "3 ',"    should read  --3',--
      Column 5, lines 27-28:  "tiaranones"  should read
--flavanones--
      Column 5, line 36:   "hf1, HF2"  should read --(Hf1, Hf2--
      Column 5, line 38:   "routants"  should read --mutants--
      Column 5, line 56:   "3,5'"   should read  --3',5'--
      Column 6, lines 6, 16, 24, 25, 28 & 34-35: "transgenie"
should read --transgenic--
      Column 6, lines 18 & 52:  "routants"  should read
--mutants--
      Column 6, line 38:  "hydroxytating"  should read
--hydroxylating--
      Column 7, line 2:  "ribozyrnes"  should read
--ribozymes--
```

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 7, lines 5, 14, 15, 21, 28, 31 & 32: "transgenie" should read --transgenic--

Column 7, line 40: "trarmgenic" should read --transgenic--

Column 7, line 65: "eDNA" should read --cDNA--

Column 7, line 68: after "molecules" insert --.--

Column 8, line 4: "arnino" should read --amino--

Column 8, line 5: "No. 1" should read --NO:2--

Column 8, line 16: delete "/"

Column 8, line 31: "3glucoside" should read --3-glucoside--

Column 8, line 32: before "acylation" insert --2 = --

Column 8, line 38: "3H" should read --$^3$H--

Column 8, lines 39-40: "pentahydroxyfiavanone" should read --pentahydroxyflavanone--

Column 8, line 49: "RS1" should read --R51--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 8, line 58: "hydroxylareal" should read --hydroxylated--

Column 9, line 4: "arnino" should read --amino--

Column 9, lines 13, 18, 19, 20, 50 & 53: "eDNA" should read --cDNA--

Column 9, line 31: "sn. LI-F2.,oRI" should read --SalI-EcoRI--

Column 9, line 38: "32P" should read --$^{32}$P--

Column 9, line 44: "(SEQ> No. should read --(SEQ. ID NO.--

Column 9, line 45: "No. 2" should read --NO: 27

Column 10, line 2 & 26: "Xbal" should read --XbaI--

Column 10, line 13: "20 lag" should read --20 µg--

Column 10, line 20: "RS1" should read --R51--

Column 10, line 30: "V23like" should read --V23-like--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 10, lines 34, 46, 52, 56 & 59: "eDNA" should read --cDNA--

Column 10, line 36: "M13-rnp18" should read --M13-mp18--

Column 10, line 42: "$3" should read --S3--

Column 11, line 6: "hyclroxylase" should read --Hydroxylase--

Column 11, lines 7, 16, 17 & 34: "3H" should read --$^3$H--

Column 11, line 11: "3,5'" should read --3',5'--

Column 11, lines 18 & 22: "hydroxylareal" should read --hydroxylated--

Column 11, line 37: "transgenies" should read --transgenic--

Column 11, line 50: "bO Ball" should read --bp BalI--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 11, line 55: "eDNA" should read --cDNA--
Column 11, line 55: "101ag" should read --10 µg--
Column 11, line 56: "EcooRI" should read --EcoRI--
Column 12, line 8: "A(" should read -- (--
Column 12, line 8: "Argg" should read --Arg--
Column 12, line 9: "$\lambda$ 80" should read -- $\phi$ 80 --
Column 12, line 11: delete "p0"
Column 12, line 12: "enctA1" should read --endA1--
Column 12, line 14: "ad" should read --a1--
Column 12, line 15: "mcrA'" should read --$\underline{mcrA}^-$--
Column 12, line 17: "(ter$^5$)" should read --(tet$^r$)--
Column 12, line 31: "tumefacierts" should read --tumefaciens--
Column 12, line 32: "51ag" should read --5 µg--
Column 12, line 43: "turnefacienscarrying" should read --tumefaciens carrying--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 13, line 44: "sucrose." should read --sucrose,--
Column 13, line 45: "Pepstalin" should read --Pepstatin--
Column 13, line 45: "Leupeptim" should read --Leupeptin--
Column 13, line 48: "rain" should read --min--
Column 13, line 49: "after "5'" insert -- - --
Column 13, line 54: "Storz" should read --Stotz--
Column 13, line 55: "51L" should read --5 µg--
Column 13, line 64: "btL" should read --µL--
Column 13, line 64: "tritiatect" should read --tritiated--
Column 13, lines 65-66: after "Merck" insert --Art--
Column 14, line 8: "Leaves were harvested..." should begin on line 9

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 14, line 20: "flitrate" should read --filtrate--
Column 14, line 26: after "for" insert --3.5--
Column 14, line 34: "$\Delta$ ZAP" should read --$\lambda$ ZAP--
Column 14, line 35: "25 lag" should read --25 µg--
Column 14, line 38: "ad" should read --al--
Column 14, line 39: "(10.0" should read --(100--
Column 14, line 46: "oligoodT" should read --oligo-dT--
Column 14, line 48: "poly(A)$^{30}$" should read --poly(A)$^{+}$--
Column 14, line 49: "20 laL" should read --20 µL--
Column 14, line 52: "lag" should read --µg--
Column 14, line 56: "laL" should read --µL--
Column 14, line 59: "MgC12" should read --MgCl$_2$--
Column 14, lines 62 & 66: "polyrnerase" should read --polymerase--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

```
        Column 14, lines 65 & 68:  "eDNA"  should read
--cDNA--
        Column 15, line 8:   "eDNA"  should read --cDNA--
        Column 15, line 9:   "100 gL" should read --100 µL--
        Column 15, line 18:  "TIE"   should read --TE--
        Column 15, line 18:  "HCI"   should read --HC1--
        Column 15, line 22:  "7.5 aL" should read --7.5 µL--
        Column 15, line 30:  " △ ZAPII"  should read
-- λ ZAPII--
        Column 15, line 41:  "transfeeling"  should read
--transfecting--
        Column 15, line 67:  "CGAGTTTTTTTTTTTTTT"  should read
--CGAGTTTTTTTTTTTTTTTTTT--
        Column 16, line 18:  "(K) St t(G)"  should read
--(K) R I(G)--
        Column 16, line 38:  "arnino"  should read --amino--
        Column 16, line 38:  "eDNA"   should read --cDNA--
```

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

It is certified that error appears in the above-indentified patent and that said Letters Patent is hereby corrected as shown below:

Column 16, line 39: "A.ZAP" should read --$\lambda$ ZAP--
Column 16, line 41: "transferred" should read --transfected--
Column 16, line 46: "eta/" should read --et al--
Column 16, line 51: "KCI," should read --KCl,--
Column 16, line 54: "50bXL" should read --50 µL--
Column 16, line 57: "Genec bean" should read --Geneclean--
Column 17, line 20: "CsCI" should read --CsCl--
Column 17, line 36: "eDNA" should read --cDNA--
Column 17, line 39: "NAG1" should read --NaCl--
Column 17, line 57: "TA1E" should read --TAE--
Column 17, line 61: "NaCI" should read --NaCl--
Column 18, line 2: "eDNA" should read --cDNA--
Column 18, line 4: "Sinai" should read --<u>Sma</u>I--
Column 18, line 4: "M13'" should read --M13--
Column 18, line 7: "$^{31}$P" should read --$^{32}$P--

UNITED STATES PATENT AND TRADEMARK OFFICE
CERTIFICATE OF CORRECTION

PATENT NO. : 5,349,125
DATED : September 20, 1995
INVENTOR(S) : Timothy A. Holton, et al.

It is certified that error appears in the above-indentified patent and that said Letters Patent is hereby corrected as shown below:

```
Column 18, line  9:  "laCi"  should read -- µCi--
Column 18, line 10:  "(α"    should read --[α--
Column 18, line 39:  "Hornology"  should read
--Homology--
Column 18, line 49:  "a/"  should read --al--
Column 18, line 54:  "was" should read --mas--
Column 19, lines 23 & 28:  "eDNA"  should read --cDNA--
Column 19, line 37:  "transform ants"  should read
--transformants--
Column 19, line 46:  "arnino"  should read --amino--
Column 19, line 49:  after "microsomal" delete --]--
Column 19, line 51:  delete --10--
Column 19, line 61:  "TIE"  should read --TE--
Column 19, line 67:  "IL1"  should read --µl--
Column 20, lines 7 & 21:  "rain"  should read --min--
Column 20, line  9:  "CA"  should read --GA--
```

UNITED STATES PATENT AND TRADEMARK OFFICE
CERTIFICATE OF CORRECTION

PATENT NO. : 5,349,125
DATED : September 20, 1995
INVENTOR(S) : Timothy A. Holton, et al.

It is certified that error appears in the above-indentified patent and that said Letters Patent is hereby corrected as shown below:

Column 20, line 28: "Agobacterium turnefaciens" should read --Agrobacterium tumefaciens--
Column 20, line 50: "et" should read --α--
Column 20, line 53: "a-" should read --α- --
Column 20, line 62: "transgenie" should read --transgenic--
Column 20, line 66: "lat." should read --µE.--
Column 21, line 2: "tabacurn" should read --tabacum--
Column 21, line 6: "I mg" should read --1 mg--
Column 21, line 11: "transgenie" should read --transgenic--
Column 21, line 14: "L I.AA" should read --L IAA--
Column 21, line 20: delete --x,--
Column 21, line 31: "MVvrD" should read --MWD--
Column 21, line 36: "flavonoicts" should read --flavonoids--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holton, et al.

Page 13 of 18

It is certified that error appears in the above-indentified patent and that said Letters Patent is hereby corrected as shown below:

Column 21, line 40: "0,451a" should read --0.45µ--
Column 21, line 54: "cone." should read --conc.--
Column 22, line 26: "Ftf1" should read --Hf1--
Column 22, line 38: "Talon" should read --Taton--
Column 22, line 53: "eDNA" should read --cDNA--
Column 23, line 7: "FMPEGAGXRXCLG" should read --FMPFGAGXRXCLG--
Column 23, line 16: "Hind1II" should read --HindIII--
Column 23, line 19: "codohs" should read --codons--
Column 23, lines 23, 47 & 63: "eDNA" should read --cDNA--
Column 23, line 32: "hornology" should read --homology--
Column 24, line 9, 11, 42 & 47: "eDNA" should read --cDNA--

UNITED STATES PATENT AND TRADEMARK OFFICE
CERTIFICATE OF CORRECTION

PATENT NO. : 5,349,125  
DATED : September 20, 1994  
INVENTOR(S) : Timothy A. Hölton, et al.

It is certified that error appears in the above-indentified patent and that said Letters Patent is hereby corrected as shown below:

Column 24, line 18: "hornology" should read --homology--

Column 24, line 28: after "5'" insert -- - --

Column 24, line 30: "Viaming eta/" should read --Vlaming et al--

Column 24, line 55: "hL2/hf,2" should read --hf2/hf2--

Column 24, line 62: "Viaming" should read --Vlaming--

Column 24, line 63: "(F-If1/Hf1)" should read --(Hf1/Hf1)--

Column 24, line 63: "1/ph1" should read --ph1/ph1--

Column 24, line 65: "Phi/" should read --Ph1

Column 24, line 67: "phi/ph1" should read --ph1/ph1--

Column 25, line 1: "the and" should read --the Hf2 and--

Column 25, line 5: "eDNA" should read --cDNA--

UNITED STATES PATENT AND TRADEMARK OFFICE
CERTIFICATE OF CORRECTION

PATENT NO. : 5,349,125
DATED : September 20, 1995
INVENTOR(S) : Timothy A. Holton, et al.

It is certified that error appears in the above-indentified patent and that said Letters Patent is hereby corrected as shown below:

Column 25, line 15: "RS1" should read --R51--
Column 25, line 21: "I-I11" should read --Hf1--
Column 25, lines 24 & 57: "Hind1II" should read --HindIII--
Column 25, line 33: "tn" should read --in--
Column 25, line 36: "RS1" should read --R51--
Column 25, line 39: "HindI11" should read --HindIII--
Column 25, line 41: "RS1F=" should read --R51 F$_2$--
Column 25, line 45: "1211/1211" should read --ph1/ph1--
Column 26, line 1: after "by" insert --XbaI--
Column 26, line 1: "RS1" should read --R51--
Column 26, line 9 & 12: "hydroxylage" should read --hydroxylase--
Column 26, line 17: --HI2--and produce--.
Column 26, lines 21, 24 & 27: "wag" should read --was--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holten, et al.

It is certified that error appears in the above-indentified patent and that said Letters Patent is hereby corrected as shown below:

```
Column 26, line 23:    "pCGPt75"      should read --PCGP175--
Column 26, lines 30 & 63: "eDNA"      should read --cDNA--
Column 26, line 66:    "pYG/22m"      should read --pYGA22m--
Column 27, lines 6 & 19:  "eDNA"      should read --cDNA--
Column 28, lines 14 & 35: "transgenie" should read
--transgenic--
Column 28, line 15:    "mounts"       should read --amounts--
Column 28, line 19:    "methylareal"  should read
--methylated--
Column 28, line 33:    "nontransgenie" should read
--non-transgenic--
Column 28, line 41:    "eDNA"         should read --cDNA--
Column 29, line 5:     "32P"          should read --$^{32}$P--
Column 29, line 5:     "eDNA"         should read --cDNA--
Column 29, line 31:    "pUG"          should read --pUC--
Column 30, line 28:    "927"          should read --8927--
```

UNITED STATES PATENT AND TRADEMARK OFFICE
CERTIFICATE OF CORRECTION

PATENT NO. : 5,349,125
DATED : September 20, 1994
INVENTOR(S) : Timothy A. Holten, et al.

It is certified that error appears in the above-indentified patent and that said Letters Patent is hereby corrected as shown below:

Column 30, line 31: "235(186" should read --235(1): 186--

Column 32, line 8: "S.C." should read --S.G.--

Column 47, line 51, Claim 3: after "The" insert --isolated--

Column 47, line 52, Claim 3: before "petunia" insert --is of--

Column 47, line 52, Claim 3: "3'5'-" should read --3',5'- --

Column 47, line 56, Claim 4: "3'5-" should read --3'5'- --

Column 47, line 57, Claim 5: after "acid" delete --isolate--

Column 47, line 59, Claim 5: "NO: 24" should read --NO: 29--

UNITED STATES PATENT AND TRADEMARK OFFICE
CERTIFICATE OF CORRECTION

PATENT NO. : 5,349,125
DATED : September 20, 1994
INVENTOR(S) : Timothy A. Holten, eet al.

It is certified that error appears in the above-indentified patent and that said Letters Patent is hereby corrected as shown below:

Column 48, line 48, Claim 9: "products" should read --HI2--and produce--.

Column 48, line 62, Claim 12: "petunia" should read --petunia--

Column 48, line 63, Claim 12: "products" should read --produces--

Column 49, line 1, Claim 13: "petunia" should read --petunia--

Signed and Sealed this

Third Day of September, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Phe  Xaa  Xaa  Gly  Xaa  Arg  Xaa  Cys  Xaa  Gly
 1              5                        10
```

( 2 ) INFORMATION FOR SEQ ID NO:2:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Pro  Gly  Phe  Ala  Gly  Arg  Arg  Ile  Cys  Pro  Gly
 1              5                        10
```

( 2 ) INFORMATION FOR SEQ ID NO:3:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

```
GGAAGCTTAT NCCNTTYGGN GCNGG                                25
```

( 2 ) INFORMATION FOR SEQ ID NO:4:

( i ) SEQUENCE CHARACTERISTICS:
      ( A ) LENGTH: 27 base pairs
      ( B ) TYPE: nucleic acid
      ( C ) STRANDEDNESS: single (D) TOPOLOGY: linear (ii) MOLECULE TYPE: DNA (genomic)

(xi) SEQUENCE DESCRIPTION: SEQ ID NO:4:

GGATGACTCA GTAAAACGAC GGCCAGT                                    27

(2) INFORMATION FOR SEQ ID NO:5:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:5:

CCNGGRCANA TNCKYYTNCC NGCNCCRAAN GG                              32

(2) INFORMATION FOR SEQ ID NO:6:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:6:

GGATGACTCA AACAGCTATG ACCATG                                    26

(2) INFORMATION FOR SEQ ID NO:7:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:7:

GTTCAATTCG GAATGATG                                             18

(2) INFORMATION FOR SEQ ID NO:8:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:8:

GCTGCACTTA ATCCATAT                                             18

(2) INFORMATION FOR SEQ ID NO:9:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:9:

TGCATAGCTT TTGGG                                                15

( 2 ) INFORMATION FOR SEQ ID NO:10:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:10:

GAGAGAGAGA GAGAGAGAGA TCTCGAGTTT TTTTTTTTT TTTTT      45

( 2 ) INFORMATION FOR SEQ ID NO:11:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

ATGTCTCCTC CAGTG      15

( 2 ) INFORMATION FOR SEQ ID NO:12:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:12:

CTAGACTCCA ATCAC      15

( 2 ) INFORMATION FOR SEQ ID NO:13:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:13:

Pro Phe Gly Ala Gly Arg Arg Gly Cys Pro Gly
 1      5        10

( 2 ) INFORMATION FOR SEQ ID NO:14:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:14:

Pro Phe Gly Ala Gly Lys Arg Ile Cys Pro Gly
 1      5        10

( 2 ) INFORMATION FOR SEQ ID NO:15:

( i ) SEQUENCE CHARACTERISTICS:

(A) LENGTH: 11 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:15:

Pro Phe Gly Ser Gly Arg Arg Ile Cys Pro Gly
1               5                   10

(2) INFORMATION FOR SEQ ID NO:16:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

CCNTTYGGND SNGGNMRNMG NRKNTGYCCN GGN        33

(2) INFORMATION FOR SEQ ID NO:17:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

CGTGCCAATG AGCTAGG        17

(2) INFORMATION FOR SEQ ID NO:18:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

GATGTTGGTT GTACTGAG        18

(2) INFORMATION FOR SEQ ID NO:19:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

GGAAACCAGA TTTTCTTG        18

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:20:

TTTTTTTTT TTTTTTTAGC 20

( 2 ) INFORMATION FOR SEQ ID NO:21:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

GTTTTCCCAG TCACGAC 17

( 2 ) INFORMATION FOR SEQ ID NO:22:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

AACAGCTATG ACCATG 16

( 2 ) INFORMATION FOR SEQ ID NO:23:

( i ) SEQUENCE CHARACTERISTICS:
    ( A ) LENGTH: 733 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

| | | | | | | |
|---|---|---|---|---|---|---|
| TTTAGTTCAA | TTCGGAATGA | TGAGATTTCG | AGTCTCATTT | CATCAATTCA | TTCCATGAAC | 60 |
| GGTTCTGTTG | TCAACATGAC | ACAAAGATT | CTTTGTTTTA | CAAACTCTGT | GACTTGTAGA | 120 |
| ACAGCTTTCG | GGAAAGTATA | CAAAAATCAA | AATGAATTGA | TAAACTTGAT | GAGGGAAGTA | 180 |
| CTGGAATTAG | TAGGAGGATT | TGATTTTGAA | AATTCTCCGG | TTGAGTTTAT | TGGAAATCAC | 240 |
| TTTGAGCTTG | TTCCGTTTGG | TGCAGGAAAA | AGGATTTGTC | CAGGAATGCA | ATTTGGTTTA | 300 |
| GCTAATATTA | GACATCCTTT | GGCTCGATTC | CTCTACCATT | TTAACTGGGC | GCTTCCATAT | 360 |
| GAAACTAATC | CTGAAGATTT | AGATAGTCTG | AAAAATATGG | ATTAAGTGCA | GCAAAAGAGA | 420 |
| AAGATCTATA | CTTAATTGCC | GTAGATCACA | AAGAAGGTGA | TATATAAATT | CTGATGTTCT | 480 |
| GCTTAAATG | GTGAAAGTCA | TACTCTACAC | AATGCTTCAT | CTCCTTAATT | TGAGTTTGGT | 540 |
| GTACATTTGT | GTCTCCCTTT | TAGCTTTGAA | TTTCACCTTG | AAAAATGATC | ACATTTTCTT | 600 |
| TTTCTGTTAC | TCCAATTAAG | ATATATGTTG | TGGTTGGTCA | ATTATGCCAT | ATTTATCAAA | 660 |
| AGATCAAATC | AATTCCCTCG | TTGATAAGTA | TAGATTATAA | AACTGATTAA | TGAATCAAAA | 720 |
| AAAAAAAAAA | AAA | | | | | 733 |

( 2 ) INFORMATION FOR SEQ ID NO:24:

( i ) SEQUENCE CHARACTERISTICS:
    ( A ) LENGTH: 1666 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:24:

| | | | | | |
|---|---|---|---|---|---|
| TGCAATTTTT | CAACTTGGTT | TCCTTTCTCC | TTATTGTATT | TTCCCTCATT | TTCATTAAGA | 60 |
| AAATGGAAGA | AATCCAATTG | TCAAACCAAA | AAATTGCCTC | CAGGCCCATG | GAAAGTACCT | 120 |
| TTTCTTGGAA | GCTTGCTTCA | TATGGTAGGT | GGACTTCCAC | ACCATGTCCT | TAGAGATTTA | 180 |
| GCCAAAAAAT | ATGGACCAAT | TATGCACCTT | CAACTAGGTA | AATTTCTGC | CGTTGTAGTT | 240 |
| ACTTCTCCTG | AGATGGCAAG | AAAAGTACTA | AAAACTCATG | ACCTTGCATT | TGCATATAGG | 300 |
| CCTAAACTTC | TAGGCATTGA | GATTGTCTGC | TATAATAGTT | CAGACATTGC | CTTTTCCCCG | 360 |
| TATGGTGATT | ACTGGAGGCA | AATGCGTAAA | ATTTGTGTAT | GGAAGTGCT | TAGTGCCAAA | 420 |
| AATGTCCGGT | CATTTAACTC | GATTAGACGA | GATGAAATAC | TTCTTATGAT | CGATTTTTG | 480 |
| CGATCATCTC | TCGGTAAGCC | AGTTAATATA | ACAGAAAGGA | TCTTTTCATT | CACAAGCTCT | 540 |
| ATGATTTGTA | GATCAGTATT | TGGGAAAAGA | ATAAAGGAGA | AAGACGAATG | TATACGACAT | 600 |
| GTGAAAAAAA | TGACAGGCTT | AATAGATGGG | TTCGATGTGG | CTGACATATT | CCCTTCGTTG | 660 |
| AGGTTTCTTC | ATGTACTAAT | CGGTATGAAG | GGTAAAATTA | TGGATGTTCA | TCGTAAGGTA | 720 |
| GATGCTATTG | TTGAGGAAGC | TATGAATGAG | CACAAAGAAA | CTCTTCGAAC | TGGCAAGACC | 780 |
| AATGGTGAAG | TGGGAGGAGA | AGATTTAATT | GATGTATTGC | TAAGACTTAA | GGAAGAGGGA | 840 |
| GACCTTCAAC | TTCCAATCAC | AAATGACAAC | ACTAAAGCCA | TTTTAATGA | CATGTTTGCT | 900 |
| GCGGGAACAG | AAACTTCATC | AACAACAATT | AACTGGGCCA | TGGTAGAACT | GATGAAAAAT | 960 |
| CCACGTGTAT | TCGCGAAAGC | TCAAGCAGAG | GTAAGAGAAG | TCTTCAAAGG | GAAAGAAACT | 1020 |
| TTCGATGAAG | ATGATATCGA | GGAGCTGAAT | TACCTTAAGT | TAGTCATTAG | AGAAACTTTA | 1080 |
| AGATCTCACC | CTCCACTTCC | ACTTTTGCTT | CCAAGAGAAT | GTCGGAGAGA | AACAGAAATA | 1140 |
| AATGGCTACA | CTATTCCTTT | AAATACCAAA | GTCATAGTTA | ATGTTTGGGC | TATTGGAAGA | 1200 |
| GATCCAAAAT | ATTGGGATGA | TGCAGAAAGC | TTTAAGCCTG | AGAGATTTGA | ACATAACTCT | 1260 |
| TTGAATTTTG | CTGGCAATAA | TTTTGAATAT | CTTCCTTTTG | GTAGTGGAAG | GAGGATTTGC | 1320 |
| CCCGGAATAT | CATTTGGTTT | AGCTAATGTG | TATCATCCAT | GGCTCAATT | GTTGTATCAT | 1380 |
| TTCGATTGGA | GACTTCCTAC | TGGGGTCGAC | CCAAATGACT | TTGAATTGAC | TAGTTAGCTG | 1440 |
| GAGTAACTAC | TGGTAGGAAA | AGAGACCTTT | ACTTGATTTT | CACTCCTTAT | TCACCTTCTC | 1500 |
| TAAAGTGATT | AAATGGGCAA | ATTTTAATTT | GAATAATAC | TTTTTCTTGT | TTACATTTCT | 1560 |
| CTCCCATTGT | TGTATTTCAT | TTACCTATTG | TTGTACTTCT | TTCTTTTGTT | GATGTCTTAG | 1620 |
| GTTTTACCTA | TTTCTATGCA | TTTGTATTTA | AAAAAAAAAA | AAAAAA | | 1666 |

( 2 ) INFORMATION FOR SEQ ID NO:25:

( i ) SEQUENCE CHARACTERISTICS:
( A ) LENGTH: 543 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

| | | | | | |
|---|---|---|---|---|---|
| GGGATGATGA | AGCAAGGAGA | TTTCTTGGAT | GTACTTCTTG | ATCAATGTGA | TGAAGAAGGG | 60 |
| TCTGGATTTG | ATCGCCAAAC | TATCAAGCCT | CTCATCCTGG | ATTTATTCAT | TGCTGGAAGT | 120 |
| GATACATCTG | CCATAACAAC | AGAATGGGCA | ATGGCAGAAC | TACTTCGAAA | ACCTCAAGAA | 180 |
| TTTGTGAATG | CATGGGCAAT | TGGAAGAGAT | CCAAAATACT | GGGAAAAACC | ACTGGAGTTT | 240 |

```
ATGCCTGAAA  GATTCTTGAA  GTGTAGTTTG  GATTACAAAG  GTAGGGTTTG  AGTATATACC    300

ATTTGGCGCA  GGTCGAAGAA  TTTGTCCTGG  AATGCCACAT  TGCAATAAGG  ATGGTGAATT    360

TGATGCTGGC  TTCGATTATT  CACCATTTAG  TTGGGAATTA  CCTAAGGAAT  GGCACCAAAG    420

ATTTGAACAT  GGAGGAACAG  TTTGGAGTTA  CCTTGAGGAA  GGCTATTCCC  CTTATTGCCA    480

TTCCCAGTAT  GGAAGAAAAG  GTCATATTTT  AGCCCAAAAG  CTATGCATTT  TGTGTGTATG    540

TTT                                                                      543
```

(2) INFORMATION FOR SEQ ID NO:26:

(i) SEQUENCE CHARACTERISTICS:
        (A) LENGTH: 618 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
AAACAGATCA  ATGCATTGCT  TGTGGAAATA  TTTGGAGCTG  GTACAGAATC  TACAACTGCT    60

ACAAGCCAAT  GGATGCTTGT  AGAACTCCTT  AGAAATCGAC  AAGCCTTGCC  CAAAGACACT   120

CAAGTTATGG  TAAACGAGTG  GGCGATTGCG  TATGATCCTA  AGATTTGGGG  CAGCTTCAAA   180

CCCGAAAGGT  TTATCGATTC  AAAAATAGAT  CCTTTGGACC  ACAAAGGGCA  AAATTTTGAA   240

TATTTTCCTT  TTGGTTCTGG  AAGGAGAATT  TGTGCTGGAG  AACCTTGGC   TTCTAGGGTT   300

ATTCCCTTAG  CTGTTGCTTC  TATGATCCAT  AAGTTTGATA  TCACTATGTT  AGAAGATCCA   360

CTCTCATCAT  TCCTAAGTTG  AGAAGAGTGA  GGAAATTAAA  AGAAGCAGAA  GATATGTTAC   420

TATAAAAACT  CGTTATATAT  ATATATATTG  CTGTATCTAT  ATATGTGTGA  ATGATCTGCT   480

GCTCATGTTG  TGTTTTGTTG  TTTGTGTACT  ATAGGTCATA  CCTAAGTTGA  TGAAATGTCT   540

CTGAGAATAT  ATACTCCTTA  TATAATAGGA  GTAATTTACC  GATAATTAAT  ATTCCTGCGA   600

CAAAAAAAAA  AAAAAAAA                                                    618
```

(2) INFORMATION FOR SEQ ID NO:27:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
CTCGAGAATC  AATGGAAGAT  GTAAGATTAC  TAGGCTATCA  CATACCTGCT  AAAACGAGAC    60

TCTTTATCAA  TGCTTGGACA  ATGGGGAGAG  ACCCACTAAC  ATGGGAAAAT  CCAGAAGAGT   120

ATCAGCCAGA  GAGATTCTTG  AATAGAGATA  CTGATGTCAA  AGGAGTAAAC  TTTGAGTTCA   180

TTCCCTTTGG  CGCCGGCAGA  AGC                                              203
```

(2) INFORMATION FOR SEQ ID NO:28:

(i) SEQUENCE CHARACTERISTICS:
        (A) LENGTH: 1812 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
CTTTCTACTA  GCTACTTCGT  TATATATATG  TAAAATTGTG  ACTTTGAAAA  TCATTTAAAT    60
```

-continued

```
TATCATAAGG TTCATTTTAT CTTGATCAAA ATATTTACTT CGGCCATATA CGTTTTCCTT      120
TAGTCATGAT GCTACTTACT GAGCTTGGTG CAGCAACTTC AATCTTTCTA ATAGCACACA      180
TAATCATTTC AACTCTTATT TCAAAAACTA CCGGCCGGCA TCTACCGCCG GGGCCAAGAG      240
GGTGGCCGGT GATCGGAGCA CTTCCACTTT TAGGAGCCAT GCCACATGTT TCCTTAGCTA      300
AAATGGCAAA AAAATATGGA GCAATCATGT ATCTCAAAGT TGGAACATGT GGCATGGCAG      360
TTGCTTCTAC CCCTGATGCT GCTAAAGCAT TCTTGAAAAC ACTTGAGATC AACTTCTCCA      420
ATCGTCCACC TAATGCAGGT GCCACTCACT AGCTTATAAT GCTCAAGACA TGGTTTTTGC      480
ACATTATGGA CCACGATGGA AGTTGCTAAG GAAATTAAGC AACTTGCATA TGCTAGGGGG      540
AAAAGCCTTA GAGAATTGGG CAAATGTTCG TGCCAATGAG CTAGGGCACA TGCTAAAATC      600
AATGTCCGAT ATGAGTCGAG AGGGCCAGAG GGTTGTGGTG GCGGAGATGT TGACATTTGC      660
CATGGCCAAT ATGATCGGAC AAGTGATGCT AAGCAAAAGA GTATTTGTAG ATAAAGGTGT      720
TGAGGTAAAT GAATTTAAGG ACATGGTTGT AGAGTTAATG ACAATAGCAG GGTATTTCAA      780
CATTGGTGAT TTTATTCCTT GTTTAGCTTG GATGGATTTA CAAGGGATAG AAAAACGAAT      840
GAAACGTTTA CATAAGAAGT TTGATGCTTT ATTGACAAAG ATGTTTGATG AACACAAAGC      900
AACTACCTAT GAACGTAAGG GGAAACCAGA TTTTCTTGAT GTTGTTATGG AAAATGGGGA      960
CAATTCTGAA GGAGAAAGAC TCAGTACAAC CAACATCAAA GCACTTTTGC TGAATTTGTT     1020
CACAGCTGGT ACGGACACTT CTTCTAGTGC AATAGAATGG GCACTTGCAG AAATGATGAA     1080
GAACCCTGCC ATTTTGAAAA AAGCACAAGC AGAAATGGAT CAAGGTCATT GGAAGAAATA     1140
GGCGTTTACT CGAATCCGAT ATCCCAAATC TCCCTTACCT CCGAGCAATT GCAAAGAAA      1200
CATTTCGAAA ACACCCTTCT ACACCATTAA ATCTTCCTAG GATCTCGAAC GAACCATGCA     1260
TAGTCGATGG TTATTACATA CCAAAAAACA CTAGGCTTAG TGTTAACATA TGGGCAATTG     1320
GAAGAGATCC CCAAGTTTGG GAAAATCCAC TAGAGTTTAA TCCCGAAAGA TTCTTGAGTG     1380
GAAGAAACTC CAAGATTGAT CCTCGAGGGA ACGATTTTGA ATTGATACCA TTTGGTGCTG     1440
GACGAAGAAT TTGTGCAGGA ACAAGAATGG GAATTGTAAT GGTGGAATAT ATATTAGGAA     1500
CTTTGGTTCA TTCATTTGAT TGGAAATTAC CAAGTGAAGT TATTGAGTTG AATATGGAAG     1560
AAGCTTTTGG CTTAGCTTTG CAGAAAGCTG TCCCTCTTGA AGCTATGGTT ACTCCAAGGT     1620
TACAATTGGA TGTTTATGTA CCATAGCTAT AGATGTGTAT TGTGCTATAA TTGCGCATGT     1680
TGTTGGTTGT AGCATGAGAT ATTAAAAGGA GTACATGAAG CGCATTGCAT GAGTTTAACT     1740
TGTAGCTCCT TAATATTTTA GGTATTTTTC AATTAATAAG TTCTTGTTGG TTGGGTAAAA     1800
AAAAAAAAAA AA                                                        1812
```

( 2 ) INFORMATION FOR SEQ ID NO:29:

( i ) SEQUENCE CHARACTERISTICS:
        ( A ) LENGTH: 1755 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
TTGAATCCAG CTCTATCTGG CTTTAGACAA TGGTGCTACT TAGTGAGCTT GCTGCAGCAA       60
CCTTAATCTT TCTAACAACA CATATCTTCA TTTCAACTCT TCTTTCTATA ACTAACGGCC      120
GGCGTCTCCC GCCAGGGCCA AGAGGGTGGC CGGTGATCGG AGCACTTCCA CTTTTAGGAG      180
CCATGCCACA TGTTTCCTTA GCTAAAATGG CAAAAAAATA TGGAGCAATC ATGTATCTCA      240
```

-continued

| | | | | | | |
|---|---|---|---|---|---|---|
| AAGTTGGAAC | GTGTGGCATG | GTAGTTGCTT | CTACCCCTGA | TGCTGCTAAA | GCGTTCTTGA | 300 |
| AAACACTTGA | TCTCAACTTC | TCCAATCGTC | CACCTAATGC | AGGTGCCACC | CACTTAGCCT | 360 |
| ATGGTGCTCA | AGACATGGTT | TTTGCACATT | ATGGACCAAG | ATGGAAGTTG | CTAAGGAAAT | 420 |
| TAAGCAACTT | ACATATGCTA | GGGGGGAAAG | CCTTAGAAAA | TTGGGCAAAT | GTTCGTGCCA | 480 |
| ATGAGCTAGG | ACACATGCTA | AAATCGATGT | TTGATATGAG | CAGAGAAGGG | GAGAGAGTTG | 540 |
| TGGTGGCGGA | GATGTTGACA | TTTGCCATGG | CGAATATGAT | CGGACAGGTG | ATACTTAGCA | 600 |
| AAAGAGTATT | TGTAAATAAA | GGTGTTGAGG | TAAATGAATT | TAAGGACATG | GTGGTAGAGT | 660 |
| TAATGACAAC | AGCAGGGTAT | TTTAACATTG | GTGATTTTAT | TCCTTGTTTA | GCTTGGATGG | 720 |
| ATTTACAAGG | GATAGAAAAA | GGAATGAAAC | GTTTACATAA | GAAGTTTGAT | GCTTTATTGA | 780 |
| CAAAGATGTT | TGATGAACAC | AAAGCAACTA | GCTATGAACG | TAAGGGGAAA | CCAGATTTTC | 840 |
| TTGATTGTGT | TATGGAAAAT | AGGGACAATT | CTGAAGGAGA | AAGGCTCAGT | ACAACCAACA | 900 |
| TCAAAGCACT | CTTGCTGAAT | TTGTTCACAG | CTGGTACAGA | CACTTCTTCT | AGTGCAATAG | 960 |
| AATGGGCACT | TGCAGAGATG | ATGAAGAACC | CTGCCATTTT | AAAGAAAGCA | CAAGGAGAAA | 1020 |
| TGGATCAAGT | CATTGGAAAC | AATAGGCGTC | TGCTCGAATC | GGATATCCCA | AATCTCCCTT | 1080 |
| ACCTCCGAGC | AATTTGCAAA | GAAACATTTC | GAAAGCACCC | TTCTACACCA | TTAAATCTCC | 1140 |
| CTAGGATCTC | GAACGAACCA | TGCATTGTCG | ATGGTTATTA | CATACCAAAA | AACACTAGGC | 1200 |
| TTAGTGTTAA | CATATGGGCA | ATTGGAAGAG | ATCCCGAAGT | TTGGGAGAAC | CCACTAGAGT | 1260 |
| TTTATCCTGA | AAGGTTCTTG | AGTGGAAGAA | ACTCGAAGAT | TGATCCTCGA | GGAACGACT | 1320 |
| TTGAATTGAT | ACCATTTGGT | GCTGGACGAA | GAATTTGTGC | AGGGACAAGA | ATGGGAATCG | 1380 |
| TAATGGTGGA | ATATATATTA | GGAACTTTGG | TCCATTCATT | TGATTGGAAA | TTACCAAGTG | 1440 |
| AAGTTATTGA | GCTAAATATG | GAAGAAGCTT | TTGGATTAGC | TTTGCAGAAA | GCTGTCCCTC | 1500 |
| TTGAAGCTAT | GGTTACTCCA | AGGCTGCCTA | TTGATGTTTA | TGCACCTTTA | GCTTGAAACA | 1560 |
| TGCCTTTACG | TTGGTTTCAG | TTTTGGGTAG | TATAATGTTG | TGGTGTTTGG | CTATAGAAAT | 1620 |
| ATTAATAAAT | GCTAGTATCT | TGAAGGCGCG | TGCAGGGGGA | GGGGGTTGTC | TTAGATAGTA | 1680 |
| GTAATATGTT | AGCCTTCCTT | TTATTTCTTG | TGATTGTGAG | AATCTTGATA | TGTTTTCTTG | 1740 |
| AAAAAAAAAA | AAAAA | | | | | 1755 |